(12) United States Patent
Walsh et al.

(10) Patent No.: US 9,732,088 B2
(45) Date of Patent: Aug. 15, 2017

(54) C2-CARBOCYCLIC IMINOTHIAZINE DIOXIDES AS BACE INHIBITORS, COMPOSITIONS, AND THEIR USE

(71) Applicant: Merck Sharp & Dohme Corp., Rahway, NJ (US)

(72) Inventors: Shawn P. Walsh, Bridgewater, NJ (US); Jared N. Cumming, Garwood, NJ (US); Shuwen He, Fanwood, NJ (US); Brandon M. Taoka, Hoboken, NJ (US); Quang T. Truong, Morganville, NJ (US); Wen-Lian Wu, Green Brook, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/315,082

(22) PCT Filed: May 28, 2015

(86) PCT No.: PCT/US2015/032782
§ 371 (c)(1),
(2) Date: Nov. 30, 2016

(87) PCT Pub. No.: WO2015/187437
PCT Pub. Date: Dec. 10, 2015

(65) Prior Publication Data
US 2017/0114065 A1  Apr. 27, 2017

Related U.S. Application Data

(60) Provisional application No. 62/006,665, filed on Jun. 2, 2014.

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC .. C07D 417/12; C07D 417/14; C07D 513/04; C07D 513/10
USPC ................ 544/58.2; 514/227.8, 228.2, 228.5
See application file for complete search history.

(56) References Cited

FOREIGN PATENT DOCUMENTS

| WO | 2012139425 | | 10/2012 |
|---|---|---|---|
| WO | 2013028670 | | 2/2013 |
| WO | 2014059185 | A1 | 4/2014 |
| WO | 2014062553 | A1 | 4/2014 |

*Primary Examiner* — Kahsay Habte
(74) *Attorney, Agent, or Firm* — Keith D. MacMillan; John C. Todaro

(57) ABSTRACT

In its many embodiments, the present invention provides certain C2-carbocyclic iminothiazine dioxide compounds, including compounds Formula (I); or a tautomers thereof, and pharmaceutically acceptable salts of said compounds and said tautomers, wherein $R^1$, $R^2$, ring A, $R^A$, m, ring B, RB, n, ring C, $R^C$ and p are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

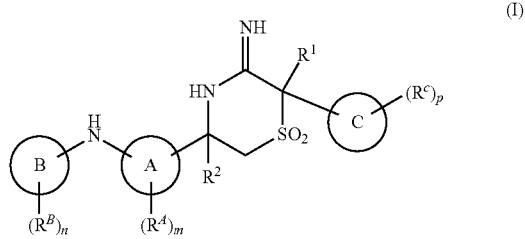

9 Claims, No Drawings

C2-CARBOCYCLIC IMINOTHIAZINE DIOXIDES AS BACE INHIBITORS, COMPOSITIONS, AND THEIR USE

FIELD OF THE INVENTION

This invention provides certain C2-carbocyclic iminothiazine dioxide compounds, and compositions comprising these compounds, as inhibitors of BACE, which may be useful for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE-1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

SUMMARY OF THE INVENTION

The present invention provides certain C2-carbocyclic iminothiazine dioxide compounds, which are collectively or individually referred to herein as "compound(s) of the invention", as described herein. The compounds of the invention are potent inhibitors of BACE-1 and BACE-2, and may be useful for treating or preventing diseases or conditions mediated by BACE-1 and/or BACE-2. Moreover, certain compounds of the invention, as shown in tables below, not only are highly potent inhibitors of the BACE-1 enzyme BACE-1 and BACE-2, but also show:

(1) Highly potent inhibitory activity in a cellular Aβ assay, (2) Ability to lower Aβ levels in vivo, (3) Improved ability to enter the Central Nervous System as evidenced by a reduced susceptibility to efflux by p-glycoprotein, (4) Low propensity to cause phospholipidosis (an undesirable side-effect) in a cellular phospholipidosis assay, and/or (5) High selectivity for BACE-1 over Cathepsin-D, or a combination of two or more of these properties.

In one embodiment, the compounds of the invention have the structural Formula (I):

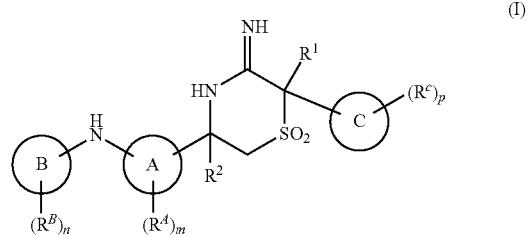

or a tautomer thereof having the structural Formula (I'):

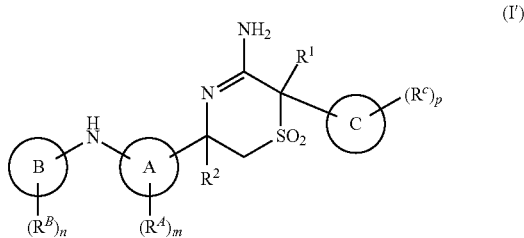

(I')

or pharmaceutically acceptable salt thereof, wherein:

$R^1$ is selected from the group consisting of H, halogen, lower alkyl, and lower heteroalkyl, wherein said lower alkyl and said lower heteroalkyl is optionally substituted with one or more halogen;

$R^2$ is selected from the group consisting of H, lower alkyl, lower cycloalkyl, and lower heteroalkyl, wherein said lower alkyl, lower cycloalkyl, and said lower heteroalkyl are optionally substituted with one or more halogen;

ring A is selected from the group consisting of phenyl, pyridinyl, pyridazinyl, pyrimidinyl, and pyrazinyl;

m is 0, 1, 2, or 3;

each $R^A$ (when present) is independently selected from the group consisting of halogen, —CN, —CH$_3$, —CH$_2$CH$_3$, —CH(CH$_3$)$_2$, cyclopropyl, —CH$_2$OCH$_3$, —CF$_3$, —CHF$_2$, —CH$_2$F, —OCH$_3$, —O-cyclopropyl, —O—CH$_2$-cyclopropyl, —OCF$_3$, —OCHF$_2$, and —OCH$_2$F;

ring B is heteroaryl;

n is 0, 1, 2, or 3;

each $R^B$ (when present) is independently selected from the group consisting of halogen, —CN, —OH, —CH$_3$, —CH$_2$CH$_3$, —CH(CH$_3$)$_2$, cyclopropyl, —CH$_2$-cyclopropyl, —CH$_2$OCH$_3$, —C≡CH, —C≡C—CH$_3$, —CF$_3$, —CHF$_2$, —CH$_2$F, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, —OCF$_3$, —OCHF$_2$, —OCH$_2$F, and —OCH$_2$CH$_2$F;

ring C is selected from the group consisting of cyclopropyl and cyclobutyl;

p is 0, 1, or 2; and each $R^C$ (when present) is independently selected from the group consisting of: halogen, —OH, —CN, lower alkyl, and lower alkoxy, where said lower alkyl and said lower alkoxy are each optionally substituted with 1 to 3 fluorine.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA). In each of the embodiments described herein, each variable is selected independently of the other unless otherwise noted.

In another embodiment, the compounds of the invention have the structural Formula (IA):

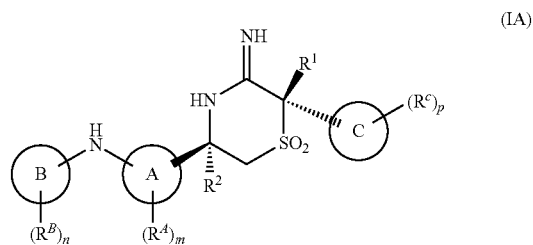

(IA)

or a tautomer thereof having the structural Formula (IA'):

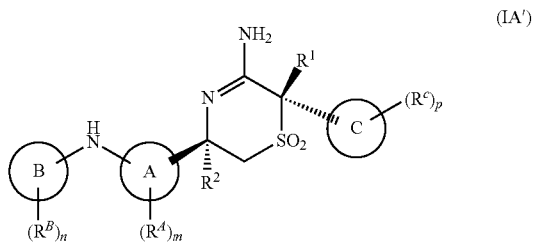

(IA')

or pharmaceutically acceptable salt thereof, wherein each variable is as described in Formula (I).

In another embodiment, in each of Formulas (I), (I'), (IA), and (IA'):

$R^1$ is selected from the group consisting of H, F, —CH$_3$, —CH$_2$F, —CHF$_2$, —CF$_3$, —CH$_2$OCH$_3$, —CH$_2$OCH$_2$CH$_3$, —CH$_2$OCH$_2$F, —CH$_2$OCHF$_2$, and —CH$_2$OCF$_3$.

In another embodiment, in each of Formulas (I), (I'), (IA), and (IA'):

$R^1$ is selected from the group consisting of —CH$_3$, —CH$_2$F, —CHF$_2$, and —CF$_3$.

In another embodiment, in each of Formulas (I), (I'), (IA), and (IA'):

$R^1$ is selected from the group consisting of —CH$_3$ and —CH$_2$F.

In another embodiment, in each of Formulas (I), (I'), (IA), and (IA'):

$R^1$ is —CH$_3$.

In another embodiment, in each of Formulas (I), (I'), (IA), and (IA'):

$R^2$ is selected from the group consisting of —CH$_3$, cyclopropyl, —CH$_2$F, —CHF$_2$, and —CH$_2$OCH$_3$;

In another embodiment, in each of Formulas (I), (I'), (IA), and (IA'):

$R^2$ is —CH$_3$.

In another embodiment, in each of Formulas (I), (I'), (IA), and (IA'):

each $R^C$ (when present) is independently selected from the group consisting of fluoro, —OH, —CN, —CH$_3$, —OCH$_3$.

In another embodiment, in each of Formulas (I), (I'), (IA), and (IA'):

ring C is cyclopropyl; and each $R^C$ (when present) is independently selected from the group consisting of: fluoro, —OH, —CN, —CH$_3$, —OCH$_3$.

In an alternative of the immediately preceding embodiment, p is 0, 1, or 2.

In another alternative of the immediately preceding embodiment, p is 0 or 1.

In another alternative of the immediately preceding embodiment, p is 0.

In another embodiment, in each of Formulas (I), (I'), (IA), and (IA'):

$R^1$ is selected from the group consisting of —CH$_3$ and —CH$_2$F;

ring C is cyclopropyl;

p is 0;

$R^2$ is —CH$_3$; and ring A, m, $R^A$, ring B, n, and $R^B$ are as defined in Formula I, or as in any of the following embodiments.

The following alternative embodiments of ring A, $R^A$, and m are applicable to and in combination with any of the embodiments described hereinabove.

In another embodiment, in each of Formulas (I), (I'), (IA), and (IA'):

ring A is selected from the group consisting of phenyl, pyridinyl, and pyrimidinyl.

In another embodiment, in each of Formulas (I), (I'), (IA), and (IA'):

each $R^A$ (when present) is independently selected from the group consisting of fluoro, chloro, —CN, —OCH$_3$, —CH$_3$, —CH$_2$OCH$_3$, —CF$_3$, —CHF$_2$, —CH$_2$F.

In another embodiment, in each of Formulas (I), (I'), (IA), and (IA'):

each $R^A$ (when present) is independently selected from the group consisting of fluoro, chloro, —CN, —OCH$_3$, —CH$_3$, —CH$_2$F.

In another embodiment, in each of Formulas (I), (I'), (IA), and (IA'):

each $R^A$ (when present) is independently selected from the group consisting of fluoro.

In another embodiment, in each of Formulas (I), (I'), (IA), and (IA'):

ring A is selected from the group consisting of phenyl, pyridinyl, pyridazinyl, pyrimidinyl, and pyrazinyl;

m is 1 or 2; and each $R^A$ is independently selected from the group consisting of fluoro, chloro, —CN, —OCH$_3$, —CH$_3$, —CH$_2$F.

In another embodiment, in each of Formulas (I), (I'), (IA), and (IA'):

ring A is selected from the group consisting of phenyl, pyridinyl, and pyrimidinyl;

m is 1 or 2; and each $R^A$ is fluoro.

In an alternative of the immediately preceding embodiment, m is 1.

In another embodiment, in each of Formulas (I), (I'), (IA), and (IA'):

ring A, $R^A$, and m form a moiety selected from the group consisting of

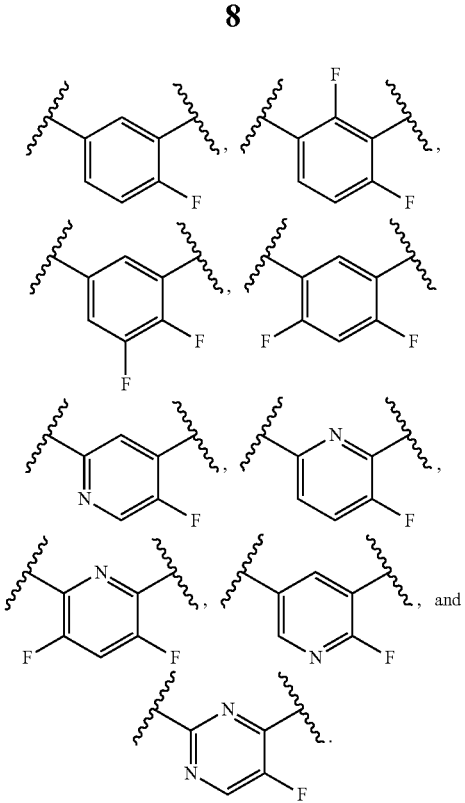

In another embodiment, in each of Formulas (I), (I'), (IA), and (IA'):

ring A, $R^A$, and m form a moiety selected from the group consisting of

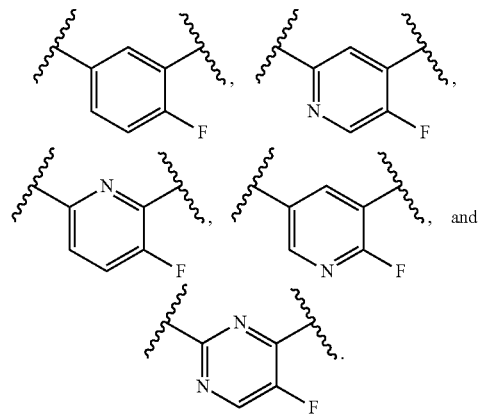

The following alternative embodiments of ring B, $R^B$, and n are applicable to and in combination with any of the embodiments described hereinabove.

In another embodiment, in each of Formulas (I), (I'), (IA), and (IA'):

ring B is selected from the group consisting of quinolinyl, isoquinolinyl, 1,5-naphthyridinyl, 1,6-naphthyridinyl, 1,7-naphthyridinyl, 1,8-naphthyridinyl, 2,6-naphthyridinyl, 2,7-naphthyridinyl, phthalazinyl, quinazolinyl, quinoxalinyl, pyrido[3,2-c]pyridazinyl, pyrido[3,2-d]pyrimidinyl, pyrido [2,3-b]pyrazinyl, pyrido[2,3-d]pyridazinyl, pyrido[2,3-d] pyrimidinyl, pyrido[2,3-c]pyridazinyl, pyrido[4,3-c] pyridazinyl, pyrido[4,3-d]pyrimidinyl, pyrido[3,4-b]

pyrazinyl, pyrido[3,4-d]pyridazinyl, pyrido[3,4-d]pyrimidinyl, pyrido[3,4-c]pyridazinyl, pteridinyl, pyrazino[2,3-d]pyridazinyl, and pyrazino[2,3-c]pyridazinyl.

In another embodiment, in each of Formulas (I), (I'), (IA), and (IA'):

ring B is selected from the group consisting of 1,5-naphthyridinyl, 1,7-naphthyridinyl, pyrido[3,2-c]pyridazinyl, pyrido[3,2-d]pyrimidinyl, pyrido[2,3-b]pyrazinyl, pyrido[2,3-d]pyridazinyl, pyrido[3,4-b]pyrazinyl, pteridinyl, pyrazino[2,3-d]pyridazinyl, and pyrazino[2,3-c]pyridazinyl.

In another embodiment, in each of Formulas (I), (I'), (IA), and (IA'):

ring B is selected from the group consisting of 1,5-napthyridinyl, 1,7-naphthyridinyl, pyrido[3,2-d]pyrimidinyl, pyrido[2,3-b]pyrazinyl, pyrido[3,4-b]pyrazinyl, and pteridinyl.

In another embodiment, in each of Formulas (I), (I'), (IA), and (IA'):

n is 0 or 1 and ring B, $R^B$, and n form a moiety selected from the group consisting of:

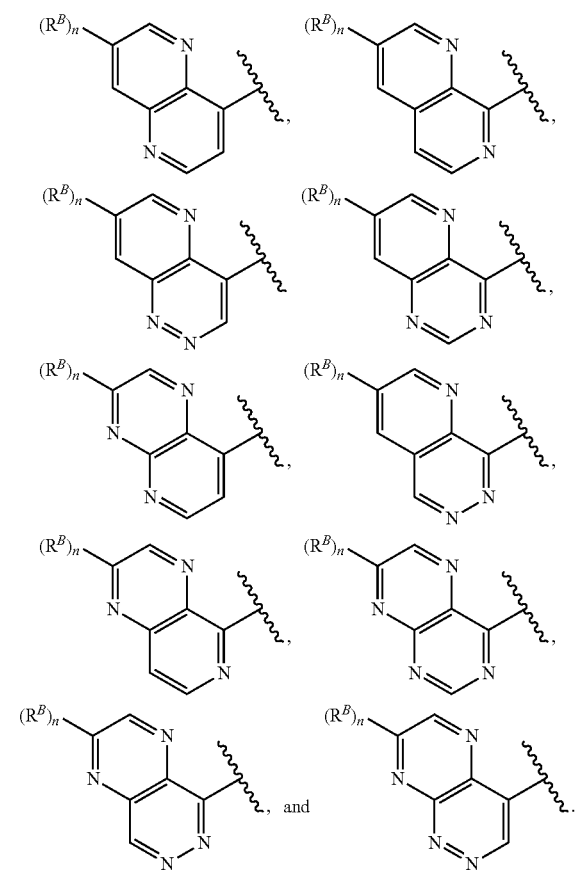

In another embodiment, in each of Formulas (I), (I'), (IA), and (IA'):

n is 0 or 1 and ring B, $R^B$, and n form a moiety selected from the group consisting of:

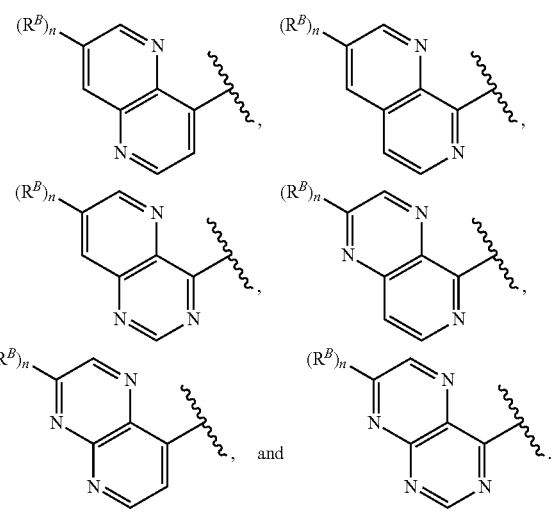

In another embodiment, in each of Formulas (I), (I'), (IA), and (IA'):

n is 1; and $R^B$ is selected from the group consisting of fluoro, chloro, bromo, iodo, —CN, —OH, —CH$_3$, cyclopropyl, —CH$_2$OCH$_3$, —C≡CH, —C≡C—CH$_3$, —CF$_3$, —CHF$_2$, —CH$_2$F, —OCH$_3$, —OCH$_2$—C≡C—H, —OCH$_2$—C≡C—CH$_3$, —OCF$_3$, —OCHF$_2$, and —OCH$_2$F.

In another embodiment, in each of Formulas (I), (I'), (IA), and (IA'):

n is 1; and $R^B$ is selected from the group consisting of fluoro, chloro, bromo, —CN, —OH, —CH$_3$, —CHF$_2$, —CH$_2$F, —OCH$_3$, —OCH$_2$—C≡C—H, and —OCH$_2$—C≡C—CH$_3$.

In another embodiment, in each of Formulas (I), (I'), (IA), and (IA'):

n is 1; and $R^B$ is selected from the group consisting of fluoro, chloro, bromo, —OH, —CN, —OCH$_3$, and —OCH$_2$—C≡C—CH$_3$.

In another embodiment, in each of Formulas (I), (I'), (IA), and (IA'):

ring B is selected from the group consisting of 1,5-naphthyridinyl, 1,7-naphthyridinyl, pyrido[3,2-c]pyridazinyl, pyrido[3,2-d]pyrimidinyl, pyrido[2,3-b]pyrazinyl, pyrido[2,3-d]pyridazinyl, pyrido[3,4-b]pyrazinyl, pteridinyl, pyrazino[2,3-d]pyridazinyl, and pyrazino[2,3-c]pyridazinyl;

n is 0, 1 or 2; and each $R^B$ (when present) is independently selected from the group consisting of fluoro, chloro, bromo, —CN, —OH, —CH$_3$, —CHF$_2$, —CH$_2$F, —OCH$_3$, —OCH$_2$—C≡C—H, —OCH$_2$—C≡C—CH$_3$.

In another embodiment, in each of Formulas (I), (I'), (IA), and (IA'):

ring B is selected from the group consisting of 1,5-naphthyridinyl, 1,7-naphthyridinyl, pyrido[3,2-d]pyrimidinyl, pyrido[2,3-b]pyrazinyl, pyrido[3,4-b]pyrazinyl, and pteridinyl;

n is 0 or 1; and $R^B$ (when present) is selected from the group consisting of fluoro, chloro, bromo, —OH, —CN, —OCH$_3$, and —OCH$_2$—C≡C—CH$_3$.

In another embodiment, in each of Formulas (I), (I'), (IA), and (IA'):

n is 0 or 1; and ring B, $R^B$, and n form a moiety selected from the group consisting of:

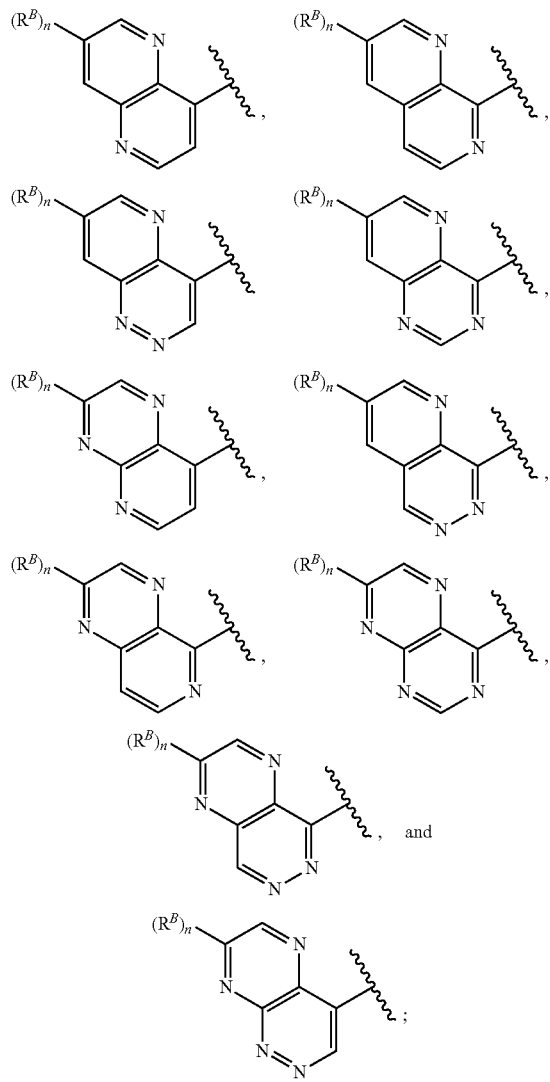

and $R^B$ (when present) is selected from the group consisting of fluoro, chloro, bromo, —CN, —OH, —CH$_3$, —CHF$_2$, —CH$_2$F, —OCH$_3$, —OCH$_2$—C≡C—H, and —OCH$_2$—C≡C—CH$_3$.

In another embodiment, in each of Formulas (I), (I'), (IA), and (IA'):

n is 0 or 1; and ring B, $R^B$, and n form a moiety selected from the group consisting of:

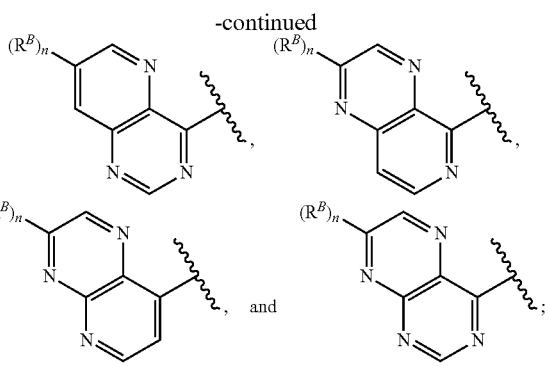

and $R^B$ (when present) is selected from the group consisting of fluoro, chloro, bromo, —OH, —CN, —OCH$_3$, and —OCH$_2$—C≡C—CH$_3$.

In another embodiment, in each of Formulas (I), (I'), (IA), and (IA'):

ring A, $R^A$, and m form a moiety selected from the group consisting of

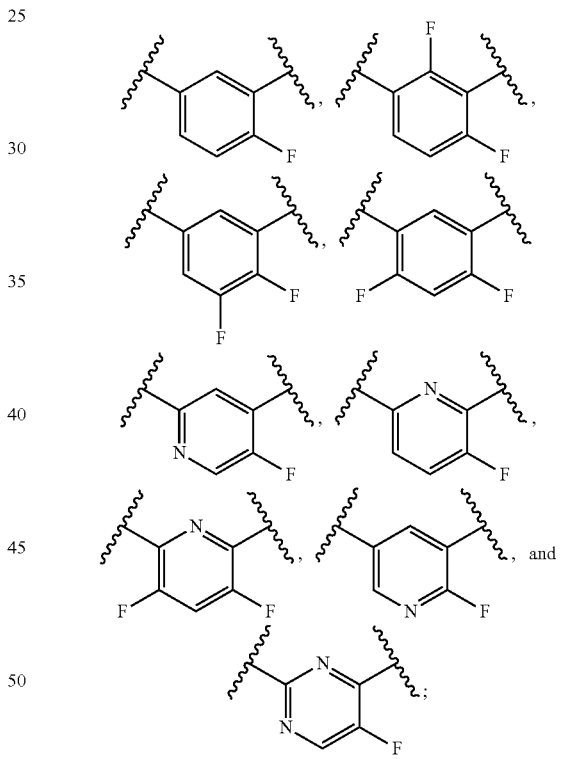

and n is 0 or 1;

ring B, $R^B$, and n form a moiety selected from the group consisting of:

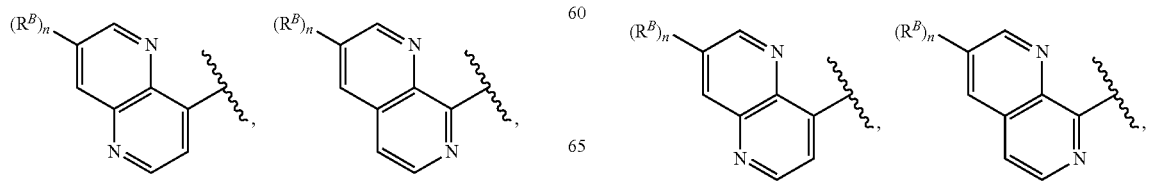

-continued

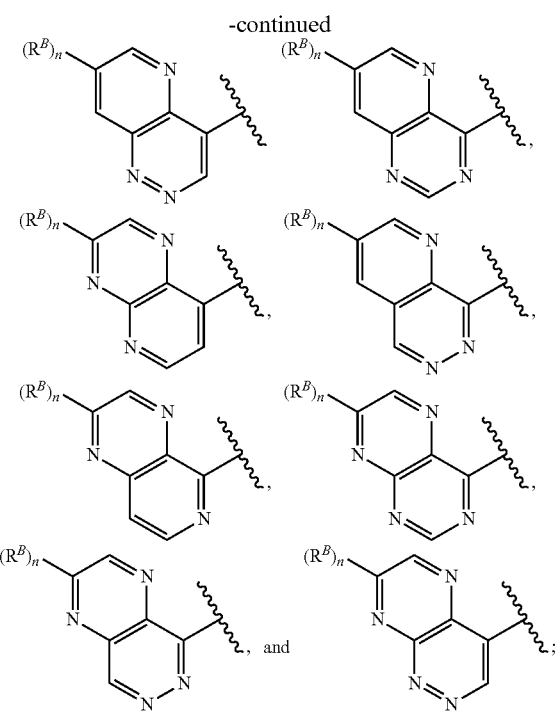

and

R$^B$ (when present) is selected from the group consisting of fluoro, chloro, bromo, —CN, —OH, —CH$_3$, —CHF$_2$, —CH$_2$F, —OCH$_3$, —OCH$_2$—C≡C—H, and —OCH$_2$—C≡C—CH$_3$.

In an alternative of the immediately preceeding embodiment, n is 0.

In another alternative of the immediately preceeding embodiment, n is 1; and R$^B$ is selected from the group consisting of fluoro, chloro, bromo, —OH, —CN, —OCH$_3$, and —OCH$_2$—C≡C—CH$_3$.

In another embodiment, in each of Formulas (I), (I'), (IA), and (IA'):

ring A, R$^A$, and m form a moiety selected from the group consisting of

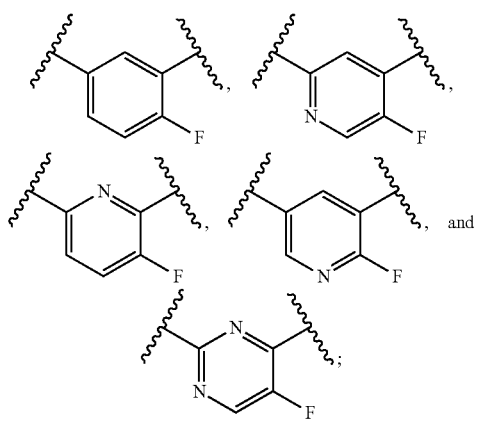

and n is 0 or 1; and ring B, R$^B$, and n form a moiety selected from the group consisting of:

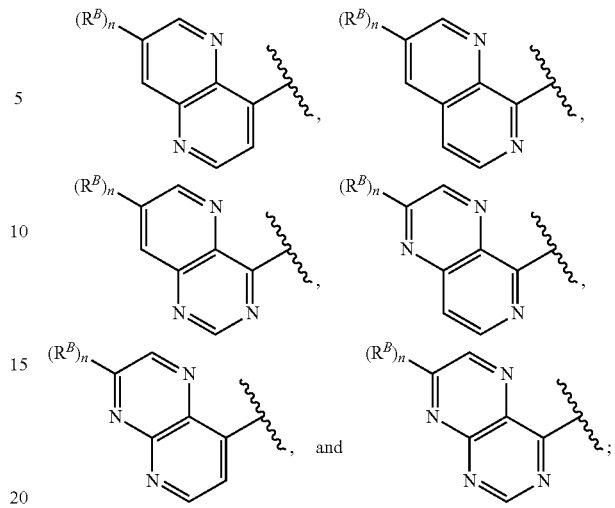

and

R$^B$ (when present) is selected from the group consisting of fluoro, chloro, bromo, —OH, —CN, —OCH$_3$, and —OCH$_2$—C≡C—CH$_3$.

In another embodiment, in each of Formulas (I), (I'), (IA), and (IA'):

R$^1$ is selected from the group consisting of —CH$_3$ and —CH$_2$F;
ring C is cyclopropyl;
p is 0;
R$^2$ is —CH$_3$;
ring A, R$^A$, and m form a moiety selected from the group consisting of

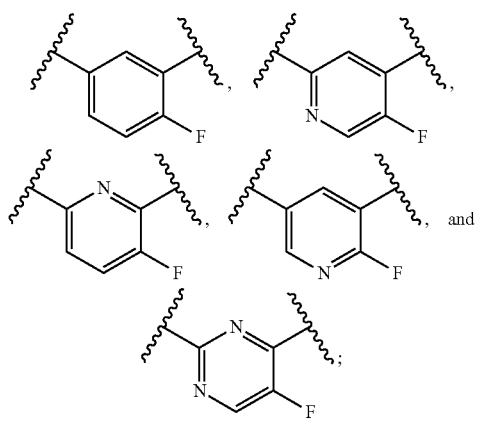

and
n is 0 or 1;
ring B, R$^B$, and n form a moiety selected from the group consisting of:

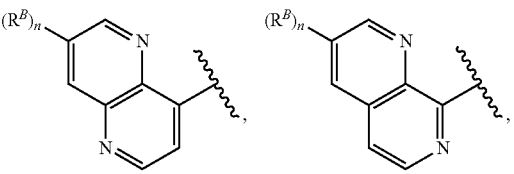

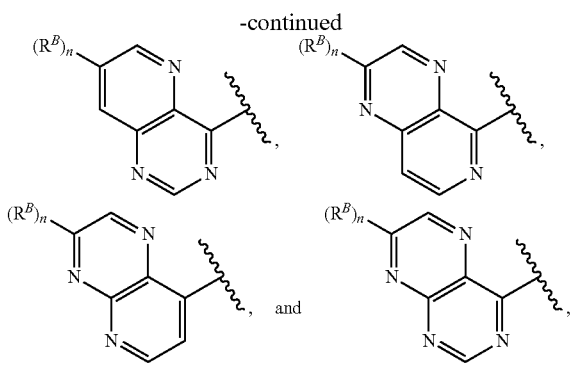

wherein $R^B$ (when present) is selected from the group consisting of fluoro, chloro, bromo, —CN, —OH, —CH$_3$, —CHF$_2$, —CH$_2$F, —OCH$_3$, —OCH$_2$—C≡C—H, and —OCH$_2$—C≡C—CH$_3$.

In an alternative of the immediately preceeding embodiment, n is 0.

In another alternative of the immediately preceeding embodiment, n is 1; $R^B$ is selected from the group consisting of fluoro, chloro, bromo, —OH, —CN, —OCH$_3$, and —OCH$_2$—C≡C—CH$_3$.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples. Where both the structures and the IUPAC names of the example compounds are provided, e.g., in the tables hereinbelow, if there are any discrepancies between the name and the structure, the pictured structure shall control.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from β$_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., m$_1$ agonists (such as acetylcholine, oxotremorine, carbachol, or McNa343), or m$_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals));

5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to about 4 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Heteroalkyl" means an alkyl moiety as defined above, which is substituted by one or more (e.g., one, two, or three) moieties independently selected from the group consisting of: —O-alkyl, —S-alkyl, —S(O)-alkyl, —S(O)$_2$-alkyl, —N(H)alkyl, and —N(alkyl)$_2$. The heteroalkyl moiety may be straight or branched and, if more than one heteroatom is present, said heteroatoms may be the same or different. Non-limiting examples of heteroalkyl include —CH$_2$OCH$_3$, —CH$_2$OCH$_2$CH$_3$, —CH$_2$OCHCH$_2$)CH$_3$, —CH$_2$OC(CH$_2$)$_2$CH$_2$CH$_3$, —CH$_2$SCH$_3$, —CH$_2$SCH$_2$CH$_3$, —CH$_2$SCHCH$_2$)CH$_3$, —CH$_2$SC(CH$_2$)$_2$CH$_2$CH$_3$, —CH$_2$NHCH$_3$, —CH$_2$NHCH$_2$CH$_3$, —CH$_2$NHCHCH$_2$)CH$_3$, —CH$_2$N(CH$_3$)C(CH$_2$)$_2$CH$_2$CH$_3$, and the like.

"Alkenyl" means an aliphatic hydrocarbon group containing at least one carbon-carbon double bond and which may be straight or branched and comprising about 2 to about 10 carbon atoms in the straight or branched chain. Branched means that one or more lower alkyl groups such as methyl, ethyl propyl, ethenyl or propenyl are attached to a linear or branched alkenyl chain. "Lower alkenyl" means about 2 to about 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means about 2 to about 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include azaindolyl, benzimidazolyl, benzoazaindolyl, benzofurazanyl, benzothiazolyl, benzothienyl, furanyl, furazanyl, imidazolyl, imidazopyridinyl, imidazothiazolyl, indolyl, isoquinolinyl, isothiazolyl, isoxazolyl, naphthyridinyl, oxadiazolyl, oxazolyl, oxindolyl, phthalazinyl, pteridinyl, pyrazinopyridazinyl, pyrazinyl, pyrazolyl, pyridazinyl, pyridonyl, pyridopyrazinyl, pyridopyridazinyl, pyridopyrimidinyl, pyridinyl, pyrimidinyl, pyrrolopyridyl, pyrrolyl, quinazolinyl, quinolinyl, quinoxalinyl, thiadiazolyl, thiazolyl, thienopyridyl, thienopyrimidyl, thienyl, triazinyl, triazolyl and the like. The term "monocyclic heteroaryl" refers to monocyclic versions of heteroaryl as described above and includes 5- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridonyl, thiazolyl, isothiazolyl, oxazolyl, oxadiazolyl, isoxazolyl, pyrazolyl, furazanyl, pyrrolyl, pyrazolyl, triazolyl, thiadiazolyl, imidazolyl, and triazinyl, and oxides thereof.

"Cycloalkyl" means a non-aromatic monocyclic or multicyclic ring system comprising about 3 to about 10 carbon atoms, preferably about 3 to about 6 carbon atoms. Monocyclic cycloalkyl refers to monocyclic versions of the cycloalkyl moieties described herein. "Lower cycloalkyl" means —($C_3$-$C_6$)cycloalkyl. Non-limiting examples of suitable monocyclic cycloalkyls include cyclopropyl, cyclobutyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

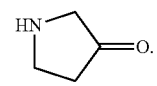

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

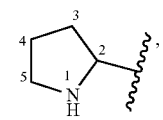

there is no —OH attached directly to carbons marked 2 and 5.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Alkoxy" means an —O-alkyl group in which the alkyl group is as previously described. Non-limiting examples of alkoxy groups include methoxy, ethoxy, n-propoxy, isopropoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —$N(R^6)_2$, or a variable appears more than once in a structure presented herein, the variables can be the same or different.

The line —, as a bond generally indicates a mixture of or either of, the possible isomers, e.g., containing (R)- and (S)-stereochemistry. For example:

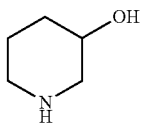

means containing both

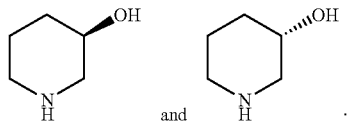

The wavy line ～, as used herein, indicates a point of attachment to the rest of the compound. Lines drawn into the ring systems, such as, for example:

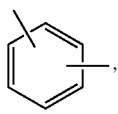

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

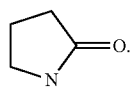

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

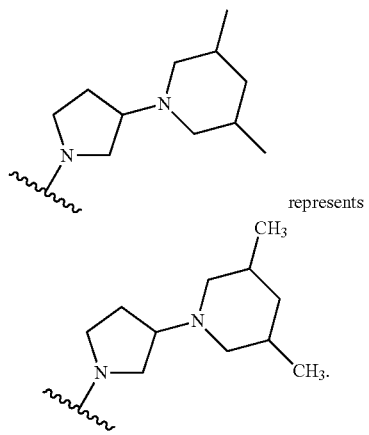

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, a compounds of the invention conforming to the formula:

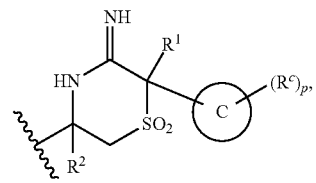

and its tautomer, which can be depicted as:

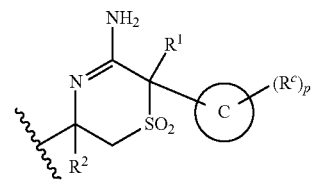

are both contemplated as being within the scope of the compounds of the invention. As noted above, while only one said tautomeric form of each compound is shown in the tables and appended claims, it shall be understood that both tautomeric forms of the compounds are contemplated as being within the scope of the non-limiting example compounds of the invention. Thus, as should be clear from the foregoing, the compounds of examples 1-24 in Table 1 below may alternatively be depicted as follows:

TABLE 1

| Ex | Structure | IUPAC Name |
|----|-----------|------------|
| 1 | 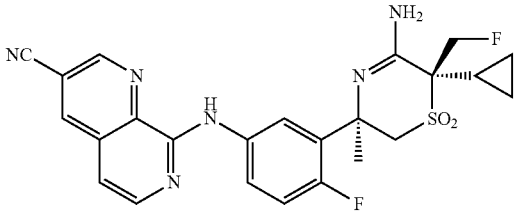 [SMILES: C[C@@]1(c2cc(Nc3nccc4cc(C#N)cnc34)ccc2F)CS(=O)(=O)[C@@](CF)(C2CC2)C(N)=N1] | 8-((3-((3R,6S)-5-amino-6-cyclopropyl-6-(fluoromethyl)-3-methyl-1,1-dioxido-3,6-dihydro-2H-1,4-thiazin-3-yl)-4-fluorophenyl)amino)-1,7-naphthyridine-3-carbonitrile |
| 2 | 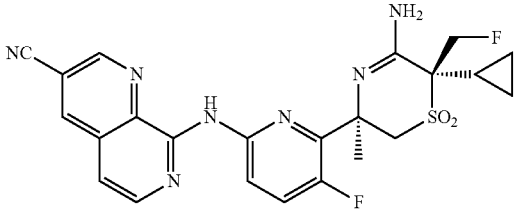 [SMILES: C[C@@]1(c2nc(Nc3nccc4cc(C#N)cnc34)ccc2F)CS(=O)(=O)[C@@](CF)(C2CC2)C(N)=N1] | 8-((6-((3R,6S)-5-amino-6-cyclopropyl-6-(fluoromethyl)-3-methyl-1,1-dioxido-3,6-dihydro-2H-1,4-thiazin-3-yl)-5-fluoropyridin-2-yl)amino)-1,7-naphthyridine-3-carbonitrile |
| 3 | 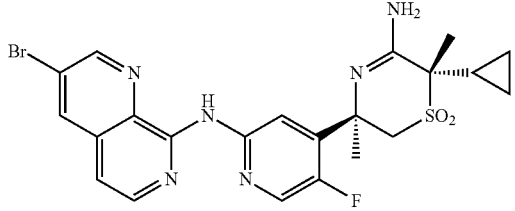 | (3R,6S)-5-amino-3-(2-((3-bromo-1,7-naphthyridin-8-yl)amino)-5-fluoropyridin-4-yl)-6-cyclopropyl-3,6-dimethyl-3,6-dihydro-2H-1,4-thiazine 1,1-dioxide |
| 4 | 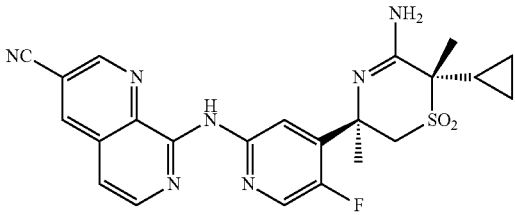 [SMILES: C[C@@]1(c2cc(Nc3nccc4cc(C#N)cnc34)ncc2F)CS(=O)(=O)[C@@](C)(C2CC2)C(N)=N1] | 8-((4-((3R,6S)-5-amino-6-cyclopropyl-3,6-dimethyl-1,1-dioxido-3,6-dihydro-2H-1,4-thiazin-3-yl)-5-fluoropyridin-2-yl)amino)-1,7-naphthyridine-3-carbonitrile |
| 5 | 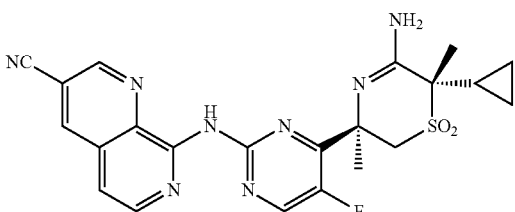 | 8-((4-((3R,6S)-5-amino-6-cyclopropyl-3,6-dimethyl-1,1-dioxido-3,6-dihydro-2H-1,4-thiazin-3-yl)-5-fluoropyrimidin-2-yl)amino)-1,7-naphthyridine-3-carbonitrile |
| 6 | 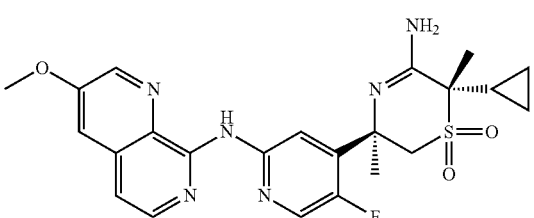 | (3R,6S)-5-amino-6-cyclopropyl-3-(5-fluoro-2-((3-methoxy-1,7-naphthyridin-8-yl)amino)pyridin-4-yl)-3,6-dimethyl-3,6-dihydro-2H-1,4-thiazine 1,1-dioxide |
| 7 | 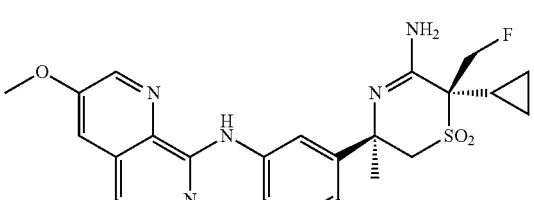 | (3R,6S)-5-amino-6-cyclopropyl-3-(2-fluoro-5-((3-methoxy-1,7-naphthyridin-8-yl)amino)phenyl)-6-(fluoromethyl)-3-methyl-3,6-dihydro-2H-1,4-thiazine 1,1-dioxide |

TABLE 1-continued

| Ex | Structure | IUPAC Name |
|---|---|---|
| 8 | 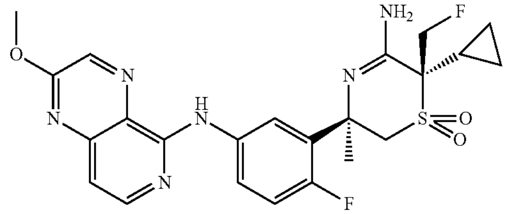 [SMILES: COc1cnc2c(Nc3ccc(F)c([C@]4(C)CS(=O)(=O)[C@@](CF)(C5CC5)C(N)=N4)c3)nccc2n1] | (3R,6S)-5-amino-6-cyclopropyl-3-(2-fluoro-5-((2-methoxypyrido[3,4-b]pyrazin-5-yl)amino)phenyl)-6-(fluoromethyl)-3-methyl-3,6-dihydro-2H-1,4-thiazine 1,1-dioxide |
| 9 | 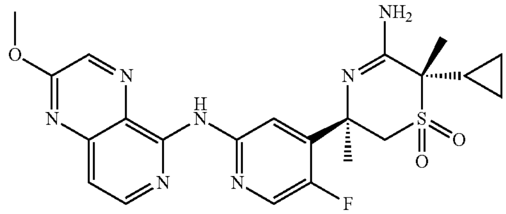 [SMILES: COc1cnc2c(Nc3cc([C@]4(C)CS(=O)(=O)[C@@](C)(C5CC5)C(N)=N4)c(F)cn3)nccc2n1] | (3R,6S)-5-amino-6-cyclopropyl-3-(5-fluoro-2-((2-methoxypyrido[3,4-b]pyrazin-5-yl)amino)pyridin-4-yl)-3,6-dimethyl-3,6-dihydro-2H-1,4-thiazine 1,1-dioxide |
| 10 | 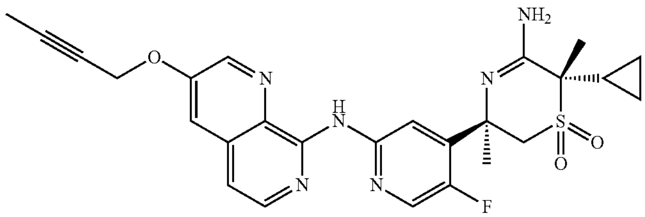 [SMILES: CC#CCOc1cnc2c(Nc3cc([C@]4(C)CS(=O)(=O)[C@@](C)(C5CC5)C(N)=N4)c(F)cn3)nccc2c1] | (3R,6S)-5-amino-3-(2-((3-(but-2-yn-1-yloxy)-1,7-naphthyridin-8-yl)amino)-5-fluoropyridin-4-yl)-6-cyclopropyl-3,6-dimethyl-3,6-dihydro-2H-1,4-thiazine 1,1-dioxide |
| 11 | 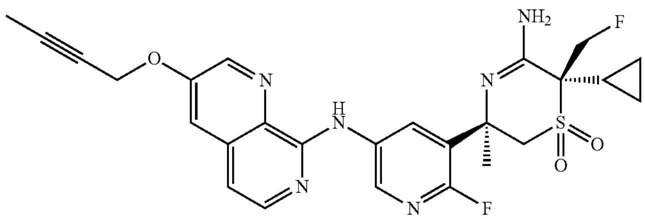 [SMILES: CC#CCOc1cnc2c(Nc3cnc(F)c([C@]4(C)CS(=O)(=O)[C@@](CF)(C5CC5)C(N)=N4)c3)nccc2c1] | (3R,6S)-5-amino-3-(5-((3-(but-2-yn-1-yloxy)-1,7-naphthyridin-8-yl)amino)-2-fluoropyridin-3-yl)-6-cyclopropyl-6-(fluoromethyl)-3-methyl-3,6-dihydro-2H-1,4-thiazine 1,1-dioxide |
| 12 | 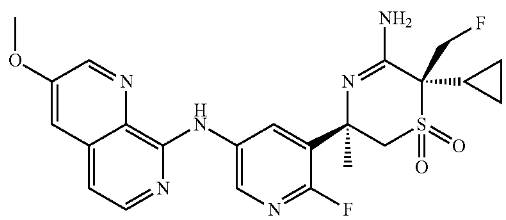 [SMILES: COc1cnc2c(Nc3cnc(F)c([C@]4(C)CS(=O)(=O)[C@@](CF)(C5CC5)C(N)=N4)c3)nccc2c1] | (3R,6S)-5-amino-6-cyclopropyl-3-(2-fluoro-5-((3-methoxy-1,7-naphthyridin-8-yl)amino)pyridin-3-yl)-6-(fluoromethyl)-3-methyl-3,6-dihydro-2H-1,4-thiazine 1,1-dioxide |
| 13 | 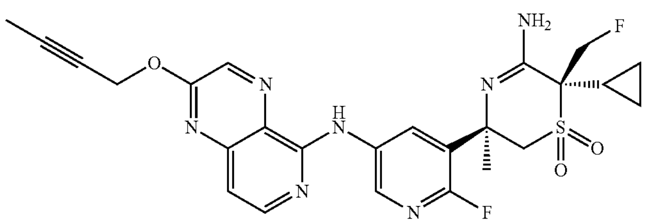 [SMILES: CC#CCOc1cnc2c(Nc3cnc(F)c([C@]4(C)CS(=O)(=O)[C@@](CF)(C5CC5)C(N)=N4)c3)nccc2n1] | (3R,6S)-5-amino-3-(5-((2-(but-2-yn-1-yloxy)pyrido[3,4-b]pyrazin-5-yl)amino)-2-fluoropyridin-3-yl)-6-cyclopropyl-6-(fluoromethyl)-3-methyl-3,6-dihydro-2H-1,4-thiazine 1,1-dioxide |
| 14 | 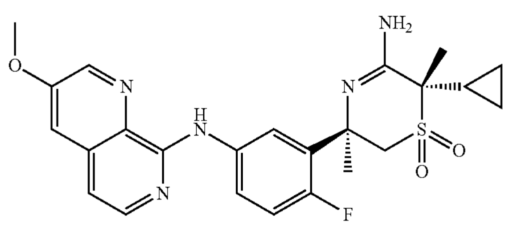 [SMILES: COc1cnc2c(Nc3ccc(F)c([C@]4(C)CS(=O)(=O)[C@@](C)(C5CC5)C(N)=N4)c3)nccc2c1] | (3R,6S)-5-amino-6-cyclopropyl-3-(2-fluoro-5-((3-methoxy-1,7-naphthyridin-8-yl)amino)phenyl)-3,6-dimethyl-3,6-dihydro-2H-1,4-thiazine 1,1-dioxide |

TABLE 1-continued

| Ex | Structure | IUPAC Name |
|---|---|---|
| 15 | 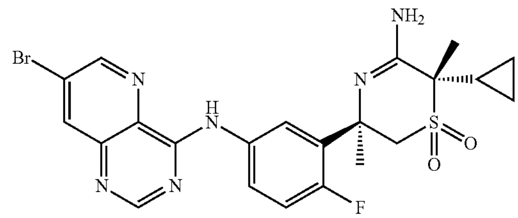 | (3R,6S)-5-amino-3-(5-((7-bromopyrido[3,2-d]pyrimidin-4-yl)amino)-2-fluorophenyl)-6-cyclopropyl-3,6-dimethyl-3,6-dihydro-2H-1,4-thiazine 1,1-dioxide |
| 16 | 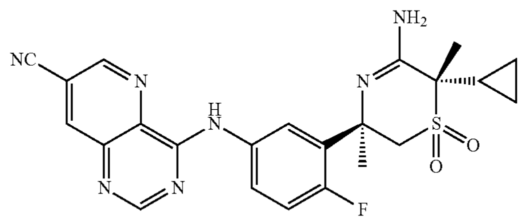 | 4-((3-((3R,6S)-5-amino-6-cyclopropyl-3,6-dimethyl-1,1-dioxido-3,6-dihydro-2H-1,4-thiazin-3-yl)-4-fluorophenyl)amino)pyrido[3,2-d]pyrimidine-7-carbonitrile |
| 17 | 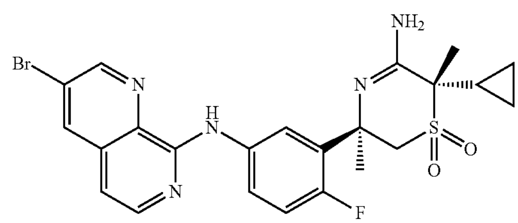 | 8-((3-((3R,6S)-5-amino-6-cyclopropyl-3,6-dimethyl-1,1-dioxido-3,6-dihydro-2H-1,4-thiazin-3-yl)-4-fluorophenyl)amino)-1,7-naphthyridine-3-carbonitrile |
| 18 | 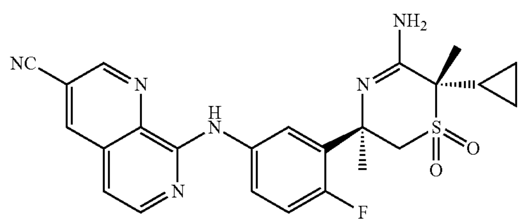 [SMILES: C[C@@]1(c2cc(Nc3nccc4cc(C#N)cnc34)ccc2F)CS(=O)(=O)[C@@](C)(C2CC2)C(N)=N1] | 8-((3-((3R,6S)-5-amino-6-cyclopropyl-3,6-dimethyl-1,1-dioxido-3,6-dihydro-2H-1,4-thiazin-3-yl)-4-fluorophenyl)amino)-1,7-naphthyridine-3-carbonitrile |
| 19 | 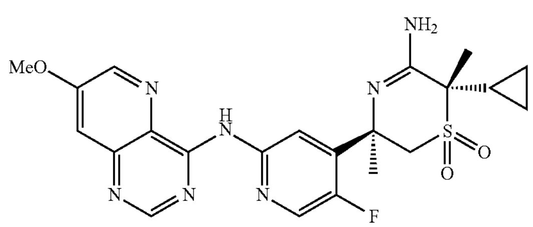 [SMILES: COc1cnc2c(Nc3cc([C@]4(C)CS(=O)(=O)[C@@](C)(C5CC5)C(N)=N4)c(F)cn3)ncnc2c1] | (3R,6S)-5-amino-6-cyclopropyl-3-(5-fluoro-2-((7-methoxypyrido[3,2-d]pyrimidin-4-yl)amino)pyridin-4-yl)-3,6-dimethyl-3,6-dihydro-2H-1,4-thiazine 1,1-dioxide |
| 20 | 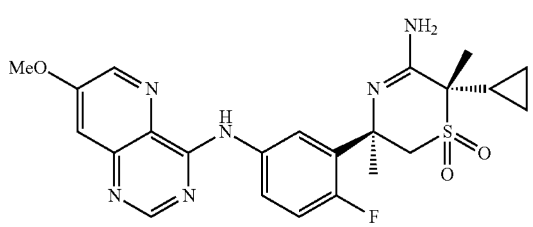 [SMILES: COc1cnc2c(Nc3ccc(F)c([C@]4(C)CS(=O)(=O)[C@@](C)(C5CC5)C(N)=N4)c3)ncnc2c1] | (3R,6S)-5-amino-6-cyclopropyl-3-(2-fluoro-5-((7-methoxypyrido[3,2-d]pyrimidin-4-yl)amino)phenyl)-3,6-dimethyl-3,6-dihydro-2H-1,4-thiazine 1,1-dioxide |
| 21 | 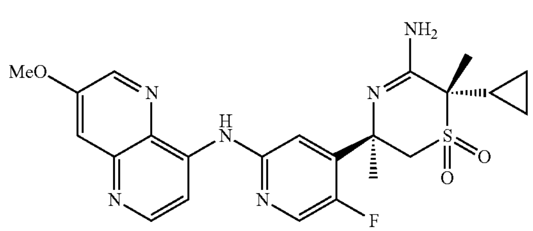 [SMILES: COc1cnc2c(Nc3cc([C@]4(C)CS(=O)(=O)[C@@](C)(C5CC5)C(N)=N4)c(F)cn3)ccnc2c1] | (3R,6S)-5-amino-6-cyclopropyl-3-(5-fluoro-2-((7-methoxy-1,5-naphthyridin-4-yl)amino)pyridin-4-yl)-3,6-dimethyl-3,6-dihydro-2H-1,4-thiazine 1,1-dioxide |

TABLE 1-continued

| Ex | Structure | IUPAC Name |
|---|---|---|
| 22 | 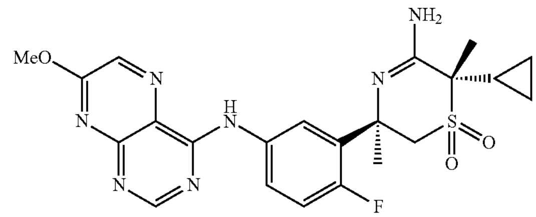 | (3R,6S)-5-amino-6-cyclopropyl-3-(2-fluoro-5-((7-methoxypteridin-4-yl)amino)phenyl)-3,6-dimethyl-3,6-dihydro-2H-1,4-thiazine 1,1-dioxide |
| 23 | 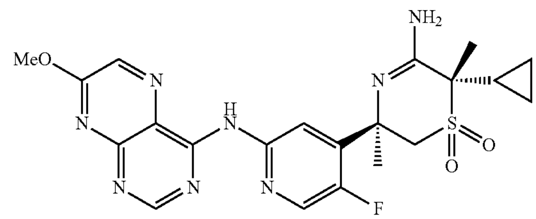 [SMILES: COc1cnc2c(Nc3cc([C@]4(C)CS(=O)(=O)[C@@](C)(C5CC5)C(N)=N4)c(F)cn3)ncnc2n1] | (3R,6S)-5-amino-6-cyclopropyl-3-(5-fluoro-2-((7-methoxypteridin-4-yl)amino)pyridin-4-yl)-3,6-dimethyl-3,6-dihydro-2H-1,4-thiazine 1,1-dioxide |
| 24 | 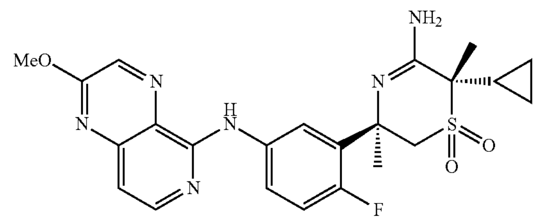 [SMILES: COc1cnc2c(Nc3ccc(F)c([C@]4(C)CS(=O)(=O)[C@@](C)(C5CC5)C(N)=N4)c3)nccc2n1] | (3R,6S)-5-amino-6-cyclopropyl-3-(5-fluoro-2-((2-methoxypyrido[3,4-b]pyiazin-5-yl)amino)pyridin-4-yl)-3,6-dimethyl-3,6-dihydro-2H-1,4-thiazine 1,1-dioxide |
| 25 | 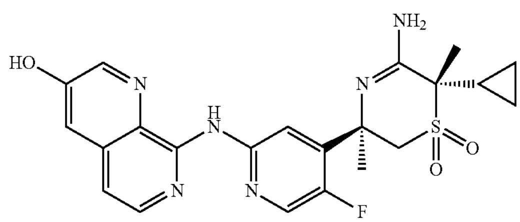 | (3R,6S)-5-amino-6-cyclopropyl-3-(5-fluoro-2-((3-hydroxy-1,7-naphthyridin-8-yl)amino)pyridin-4-yl)-3,6-dimethyl-3,6-dihydro-2H-1,4-thiazine 1,1-dioxide |
| 26 | 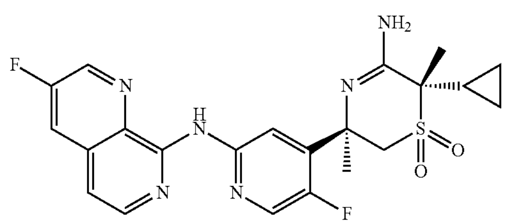 [SMILES: C[C@@]1(c2cc(Nc3nccc4cc(F)cnc34)ncc2F)CS(=O)(=O)[C@@](C)(C2CC2)C(N)=N1] | (3R,6S)-5-amino-6-cyclopropyl-3-(5-fluoro-2-((3-fluoro-1,7-naphthyridin-8-yl)amino)pyridin-4-yl)-3,6-dimethyl-3,6-dihydro-2H-1,4-thiazine 1,1-dioxide |
| 27 | 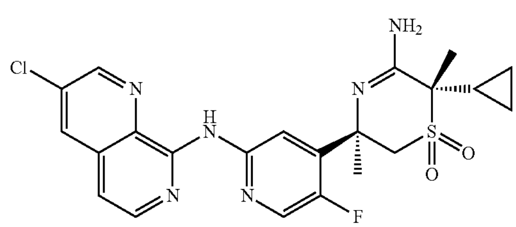 [SMILES: C[C@@]1(c2cc(Nc3nccc4cc(Cl)cnc34)ncc2F)CS(=O)(=O)[C@@](C)(C2CC2)C(N)=N1] | (3R,6S)-5-amino-3-(2-((3-chloro-1,7-naphthyridin-8-yl)amino)-5-fluoropyridin-4-yl)-6-cyclopropyl-3,6-dimethyl-3,6-dihydro-2H-1,4-thiazine 1,1-dioxide |
| 28 | 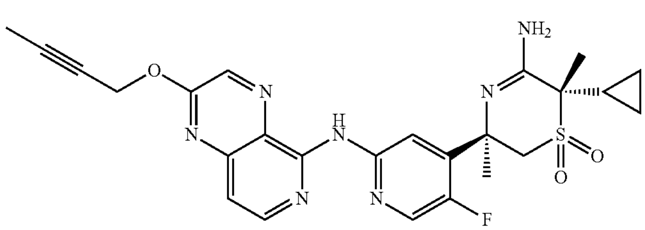 | (3R,6S)-5-amino-3-(2-((2-(but-2-yn-1-yloxy)pyrido[3,4-b]pyrazin-5-yl)amino)-5-fluoropyridin-4-yl)-6-cyclopropyl-3,6-dimethyl-3,6-dihydro-2H-1,4-thiazine 1,1-dioxide |

TABLE 1-continued

| Ex | Structure | IUPAC Name |
|---|---|---|
| 29 | 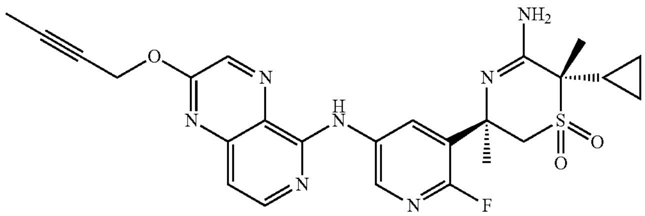 [SMILES: CC#CCOc1cnc2c(Nc3cnc(F)c([C@]4(C)CS(=O)(=O)[C@@](C)(C5CC5)C(N)=N4)c3)nccc2n1] | (3R,6S)-5-amino-3-(5-((2-(but-2-yn-1-yloxy)pyrido[3,4-b]pyrazin-5-yl)amino)-2-fluoropyridin-3-yl)-6-cyclopropyl-3,6-dimethyl-3,6-dihydro-2H-1,4-thiazine 1,1-dioxide |
| 30 | 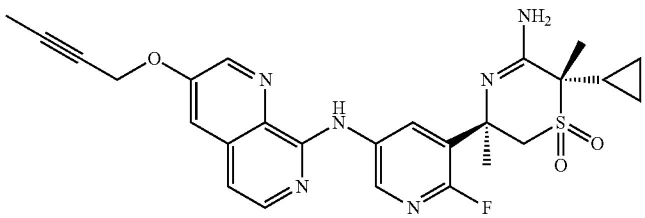 [SMILES: CC#CCOc1cnc2c(Nc3cnc(F)c([C@]4(C)CS(=O)(=O)[C@@](C)(C5CC5)C(N)=N4)c3)nccc2c1] | (3R,6S)-5-amino-3-(5-((3-(but-2-yn-1-yloxy)-1,7-naphthyridin-8-yl)amino)-2-fluoropyridin-3-yl)-6-cyclopropyl-3,6-dimethyl-3,6-dihydro-2H-1,4-thiazine 1,1-dioxide |
| 31 | 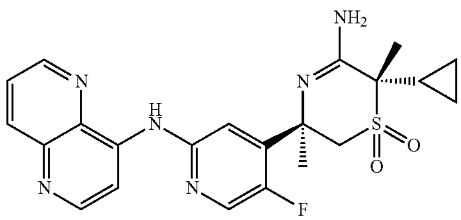 [SMILES: C[C@@]1(c2cc(Nc3ccnc4cccnc34)ncc2F)CS(=O)(=O)[C@@](C)(C2CC2)C(N)=N1] | (3R,6S)-3-(2-((1,5-naphthyridin-4-yl)amino)-5-fluoropyridin-4-yl)-5-amino-6-cyclopropyl-3,6-dimethyl-3,6-dihydro-2H-1,4-thiazine 1,1-dioxide |
| 32 | 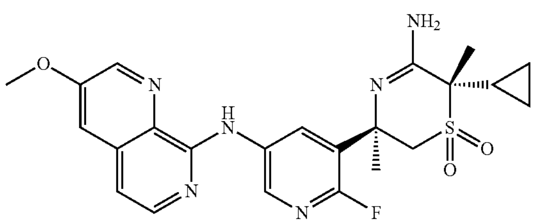 [SMILES: COc1cnc2c(Nc3cnc(F)c([C@]4(C)CS(=O)(=O)[C@@](C)(C5CC5)C(N)=N4)c3)nccc2c1] | (3R,6S)-5-amino-6-cyclopropyl-3-(2-fluoro-5-((3-methoxy-1,7-naphthyridin-8-yl)amino)pyridin-3-yl)-3,6-dimethyl-3,6-dihydro-2H-1,4-thiazine 1,1-dioxide |
| 33 | 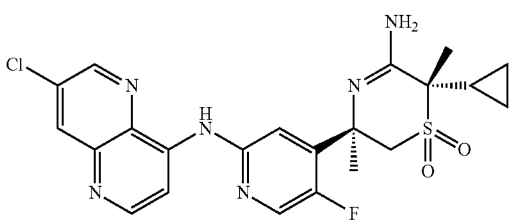 [SMILES: C[C@@]1(c2cc(Nc3ccnc4cc(Cl)cnc34)ncc2F)CS(=O)(=O)[C@@](C)(C2CC2)C(N)=N1] | (3R,6S)-5-amino-3-(2-((7-chloro-1,5-naphthyridin-4-yl)amino)-5-fluoropyridin-4-yl)-6-cyclopropyl-3,6-dimethyl-3,6-dihydro-2H-1,4-thiazine 1,1-dioxide |
| 34 | 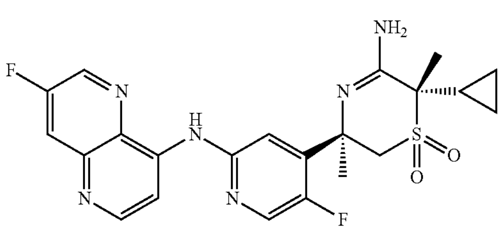 [SMILES: C[C@@]1(c2cc(Nc3ccnc4cc(F)cnc34)ncc2F)CS(=O)(=O)[C@@](C)(C2CC2)C(N)=N1] | (3R,6S)-5-amino-6-cyclopropyl-3-(5-fluoro-2-((7-fluoro-1,5-naphthyridin-4-yl)amino)pyridin-4-yl)-3,6-dimethyl-3,6-dihydro-2H-1,4-thiazine 1,1-dioxide |
| 35 | 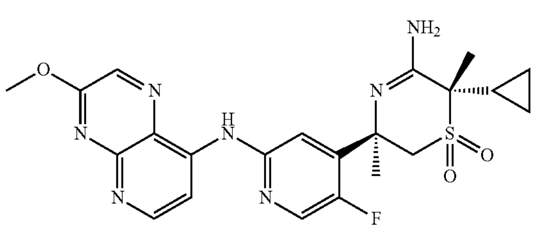 [SMILES: COc1cnc2c(Nc3cc([C@]4(C)CS(=O)(=O)[C@@](C)(C5CC5)C(N)=N4)c(F)cn3)ccnc2n1] | (3R,6S)-5-amino-6-cyclopropyl-3-(5-fluoro-2-((3-methoxypyrido[2,3-b]pyrazin-8-yl)amino)pyridin-4-yl)-3,6-dimethyl-3,6-dihydro-2H-1,4-thiazine 1,1-dioxide |

TABLE 1-continued

| Ex | Structure | IUPAC Name |
|---|---|---|
| 36 | 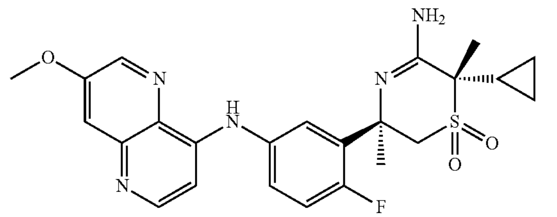 | (3R,6S)-5-amino-6-cyclopropyl-3-(2-fluoro-5-((7-methoxy-1,5-naphthyridin-4-yl)amino)phenyl)-3,6-dimethyl-3,6-dihydro-2H-1,4-thiazine 1,1-dioxide |
| 37 | 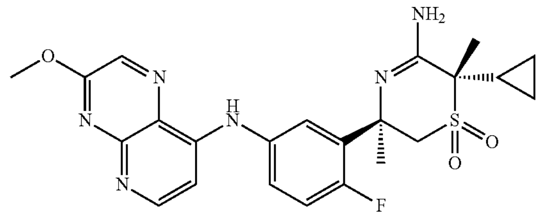 [SMILES: COc1cnc2c(Nc3ccc(F)c([C@]4(C)CS(=O)(=O)[C@@](C)(C5CC5)C(N)=N4)c3)ccnc2n1] | (3R,6S)-5-amino-6-cyclopropyl-3-(2-fluoro-5-((3-methoxypyrido[2,3-b]pyrazin-8-yl)amino)phenyl)-3,6-dimethyl-3,6-dihydro-2H-1,4-thiazine 1,1-dioxide |
| 38 | 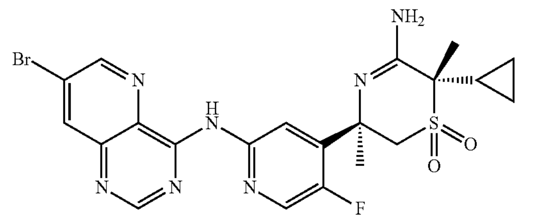 | (3R,6S)-5-amino-3-(2-((7-bromopyrido[3,2-d]pyrimidin-4-yl)amino)-5-fluoropyridin-4-yl)-6-cyclopropyl-3,6-dimethyl-3,6-dihydro-2H-1,4-thiazine 1,1-dioxide |
| 39 | 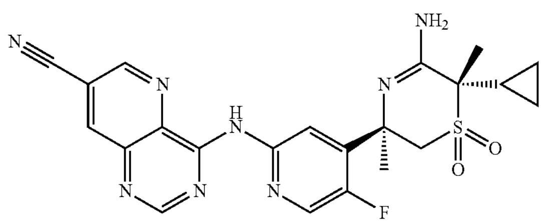 [SMILES: C[C@@]1(c2cc(Nc3ncnc4cc(C#N)cnc34)ncc2F)CS(=O)(=O)[C@@](C)(C2CC2)C(N)=N1] | 4-((4-((3R,6S)-5-amino-6-cyclopropyl-3,6-dimethyl-1,1-dioxido-3,6-dihydro-2H-1,4-thiazin-3-yl)-5-fluoropyridin-2-yl)amino)pyrido[3,2-d]pyrimidine-7-carbonitrile |

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). For example, if a compound of the invention incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation compring one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:

| | |
|---|---|
| Acetonitrile: MeCN, ACN | Dimethylsulfoxide: DMSO |
| Aqueous: aq. | 4,5-bis(Diphenylphosphino)-9,9- |
| tert-Butanol: t-BuOH | dimethylxanthene: Xantphos |
| Concentrated: conc. | Electrospray: ES |
| tris-(Dibenzylideneacetone)dipalladium: | Ethanol: EtOH |
| $Pd_2(dba)_3$ | Ethyl: Et |
| Di-tert-butyldicarbonate: $Boc_2O$ | Ethyl acetate: AcOEt, EtOAc, or |
| Dichloromethane: DCM | EA |
| Diisopropylethylamine: DIEA or | Example: Ex. |
| $iPr_2NEt$ | Grams: g |
| Dimethoxyethane: DME | Hexanes: hex |
| N,N-Dimethylaminopyridine: DMAP | High performance liquid |
| Dimethylacetamide: DMA | chromatography: HPLC |
| Dimethylformamide: DMF | Hours: h |
| Isopropyl alcohol: IPA | Milliliters: mL |
| Liquid chromatography mass | Millimoles: mmol |
| Spectrometry: LCMS | Micromoles: uM or μM |
| Liter: L | Minutes: min |
| Lithium bis(trimethylsilyl)amide: | Molar: M |
| LHMDS | n-Butyllithium: nBuLi or n-BuLi |
| Lithium diisopropylamide: LDA | Normal: N |
| Methanol: MeOH | Nuclear magnetic resonance |
| Methylmagnesium bromide: MeMgBr | spectroscopy: NMR |
| Microliters: μl or μL | Palladium on carbon: Pd/C |
| Milligrams: mg | Temperature: temp. |
| Palladium acetate: $Pd(OAc)_2$ | Tetrahydrofuran: THF |
| Petroleum ether: PE | Thin layer chromatography: TLC |
| Preparative: prep-, p- | Titanium(IV)ethoxide: $Ti(OEt)_4$ |
| Room temperature | Triethylamine: $Et_3N$ or TEA |
| (ambient, about 25° C.): rt or RT | Trifluoroacetic acid: TFA |
| Saturated: sat. | Trimetthylsilyl: TMS- |
| Silica gel: $SiO_2$ | bis(Triphenylphosphine)palladi- |
| Supercritical Fluid Chromatography: | um(II)dichloride: $Pd(PPh_3)_2Cl_2$ |
| SFC | |
| tert-Butoxycarbonyl: t-Boc or Boc | |

Compounds of the formula 1-3 (Scheme 1) can be prepared using the following general procedure. Treatment of an appropriately substituted acetonitrile (1-1) with a compatible base (such as n-BuLi, LDA, LHMDS) is followed by addition of an electrophilic sulphur source (such as dimethyldisulfide). After appropriate quench and work-up the crude product can be treated with an oxidant (such as oxone) to provide the sulphone intermediate 1-2. Subsequent treatment of 1-2 with an appropriate base (such as cesium carbonate or sodium hydride) followed by addition of an appropriately substituted electrophile (such as an alkyl halide) furnishes intermediate 1-3.

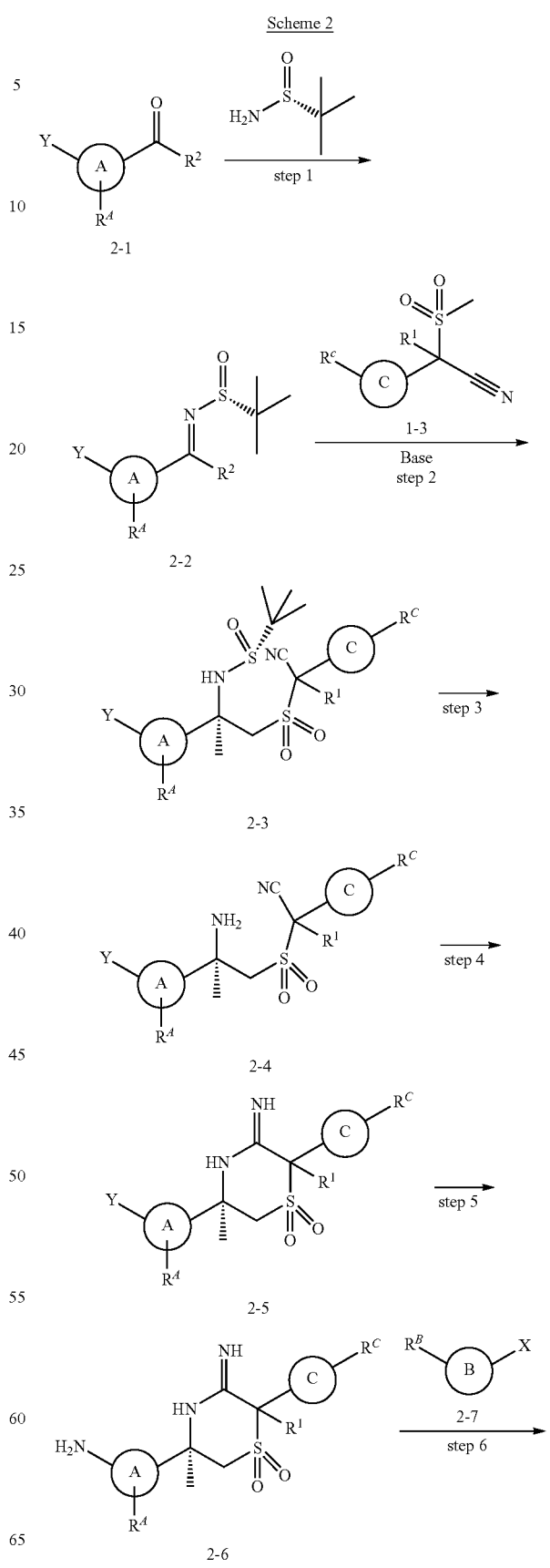

-continued

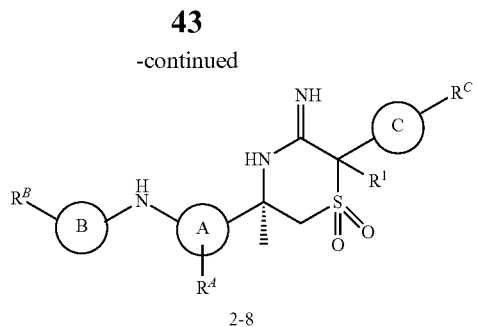

2-8

Compounds of the formula 2-8 (Scheme 2) can be prepared using the following general procedure. An appropriately substituted aryl or heteroaryl ketone (2-1) is selected, bearing a substituent (Y) which is compatable with the following sequence and can be derivitized to an amino group following step 4 (such as halogen or nitro). 2-1 is combined with (R)-2-methyl-2-propanesulfinamide and an appropriate acid or Lewis acid (such as titanium(IV)ethoxide). The resulting ketimine is then added to a solution of 1-3 which has been combined with an appropriate base (such as n-BuLi, LDA, LHMDS). Purification of the major resulting diastereomer can be effected here or at the stage of 2-4 or 2-5 (such as by p-HPLC, p-SFC, or SiO$_2$ chromatography). The chiral auxiliary of 2-3 is then hydrolyzed (for example using acid such as HCl) to provide 2-4 either as the salt or free base. Cyclization of 2-4 under acidic or Lewis acidic conditions (such as CuCl or CuBr) is followed by conversion of the Y group into the amino group of 2-6 (such as by metal catalyzed cross coupling in the case of halogen, or reduction in the case of nitro). Coupling of 2-6 with an appropriate electrophile 2-7 under metal catalysed (such as Pd) coupling conditions, or after treatment with appropriate base (such as LHMDS) provides the example compounds 2-8.

Method A

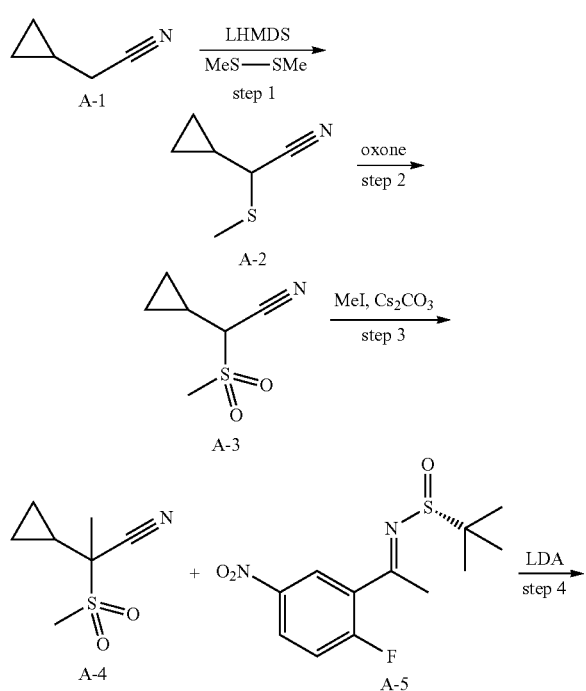

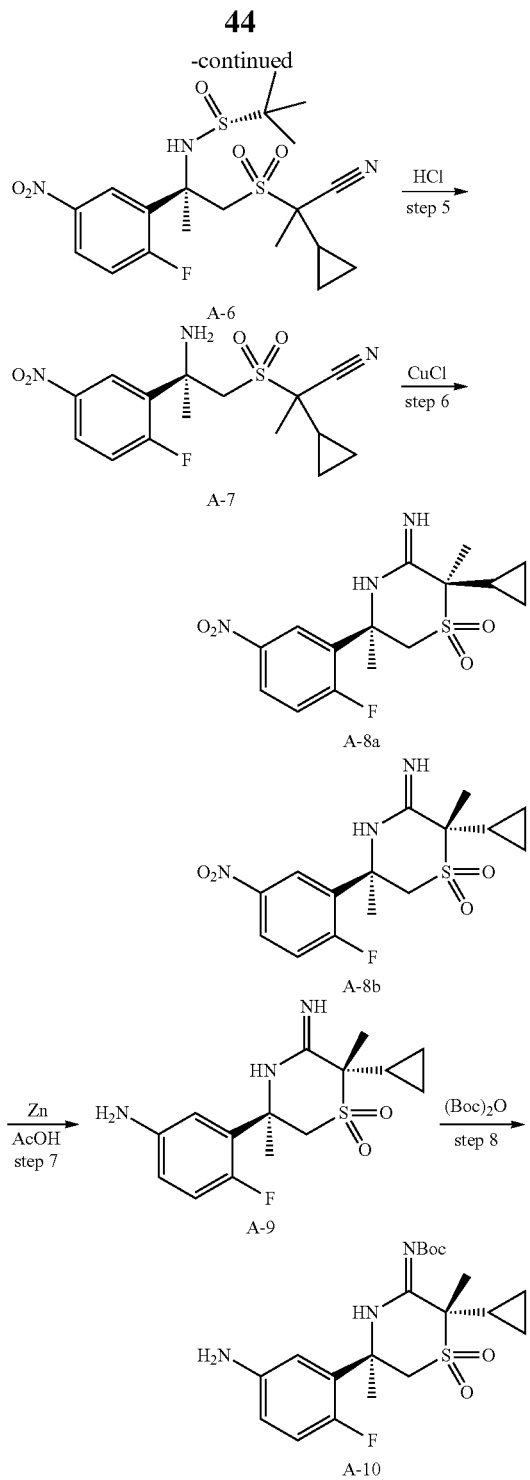

Step 1

A solution of 4.00 g (49.3 mmol) of cyclopropyl acetonitrile A-1 in 40 mL of THF was cooled in a −78° C. bath and treated with a solution of LHMDS (1.0 M in THF, 59.2 mmol) via dropwise addition. The mixture stirred 45 min. in the cooling bath, then dimethyldisulfide (4.65 g, 49.3 mmol) was added dropwise and the cooling bath was removed. The resulting mixture stirred 2 h at rt, then was quenched with saturated ammonium chloride solution (80 mL) and diluted with EtOAc and water. The layers were separated and the organic layer dried over MgSO$_4$, filtered and concentrated, to provide A-2, which was used directly in the next step without further purification. ¹H NMR for A-2 (500 MHz, CDCl₃) δ ppm 0.54 (m, 1H); 0.62 (m, 1H); 0.75 (m, 1H); 0.80 (m, 1H); 1.28 (m, 1H); 2.34 (s, 3H); 3.29 (m, 1H).

Step 2

A solution of 5.00 g of compound A-2 (39.3 mmol) in 200 mL methanol was added to a stirred, cooled (0° C.) mixture of 24.2 g of oxone (39.3 mmol) in 98 mL of water. The cooling bath was removed after complete addition and the mixture stirred at rt for 12 h. Water (600 mL) was added followed by EtOAc (300 mL) and the layers were separated. The organic layer was dried over Na₂SO₄, filtered and concentrated, to provide A-3, which was used directly in the next step without further purification. ¹H NMR for A-3 (500 MHz, CDCl₃) δ ppm 0.77 (m, 2H); 0.96 (m, 2H); 1.54 (m, 1H); 3.16 (s, 3H); 3.91 (m, 1H).

Step 3

To a suspension of compound A-3 (5.00 g, 31.4 mmol) and 11.3 g (34.5 mmol) of cesium carbonate in 105 mL of THF at rt was added 4.90 g (34.5 mmol) of iodomethane and the resulting mixture stirred 12 h at rt. Water (1050 mL) was added followed by EtOAc (2100 mL) and the layers were separated. The organic layer was dried over Na₂SO₄, filtered and concentrated. Purification by flash chromatography (80 g of SiO₂: 0 to 50% EtOAc in hexanes) provided A-4. ¹H NMR for A-4 (500 MHz, CDCl₃) δ ppm 0.77 (m, 1H); 0.88-0.97 (overlapping m's, 3H); 1.54 (m, 1H); 1.76 (s, 3H); 3.18 (s, 3H).

Step 4

To a stirred solution of 17.3 g (100 mmol) of compound A-4 in 300 mL of THF was added 50.0 mL (2.0 M in THF/heptane/ethylbenzene, 100 mmol) of LDA at −78° C. After 30 minutes, a solution of the sulfinimine A-5 (20.5 g, 71.4 mmol) in 50 mL of THF was added dropwise over 30 min. The solution was stirred at −78° C. for an additional 3 h, and quenched with 50 mL of diluted NH₄Cl solution. The mixture was extracted with two 400 mL portions of EtOAc. The combined organic extracts were washed with brine, dried (MgSO₄), filtered and concentrated; the residue was purified by flash chromatography (2×330 g of SiO₂: 0 to 40% EtOAc in hexanes) to provide compound A-6 as a mixture of two diastereomers. MS for A-6: m/e=460 (M+1).

Step 5

A solution of 14.4 g (31.3 mmol) of compound A-6 in 62.7 mL of dichloromethane in a cooling bath (0° C.) was treated with 10 mL of 4 M HCl solution in dioxane. The resulting mixture was stirred at room temperature for 2 h, then concentrated to remove solvent. The resulting residue was redissolved in 100 mL dichloromethane and washed with saturated aqueous sodium bicarbonate solution (100 mL×2). The organic layer was dried (MgSO4), filtered and concentrated to provide A-7 which was used without further purification. MS for A-7: m/e=356 (M+1).

Step 6

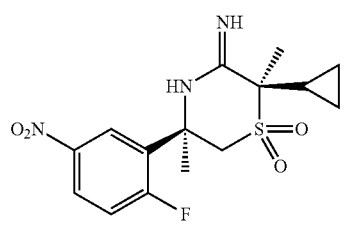

A-8a

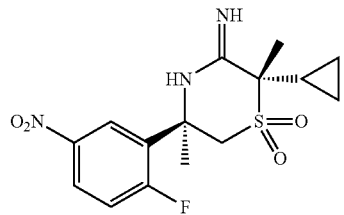

A-8b

A suspension of 3.30 g (9.36 mmol) of compound A-7 and 1.85 g (18.7 mmol) of CuCl in 187 mL of ethanol was heated at reflux for 12 h. The resulting mixture was cooled, filtered through celite, diluted with water (150 mL), and extracted with three 150 mL portions of EtOAc. The combined organic extracts were washed with brine, dried (Na₂SO₄), filtered and concentrated; the residue was purified by SFC (4.6×250 mm AD-H column, 1:1 MeCN:MeOH/CO₂, 250 g/min) to give compounds A-8a and A-8b. MS for A-8a: m/e=356 (M+1); MS for A-8b: m/e=356 (M+1).

Step 7

Zinc powder (0.0640 g, 0.979 mmol) was added slowly to a solution of compound A-8b (0.348 g, 0.979 mmol) in 0.280 mL acetic acid, 0.490 mL THF, and 0.123 mL EtOH cooled in a 0° C. bath. The cooling bath was removed and the reaction mixture was heated in a 70° C. oil bath for 12 h. An additional 0.320 g (4.90 mmol) of zinc powder was added and the reaction mixture was heated in a 70° C. oil bath for an additional 12 h. The resulting mixture was diluted with EtOAc (10 mL), filtered through celite and concentrated in vacuo. Purification by preparative TLC (5% MeOH in CH₂Cl₂ plus 1% NH₄OH) provided intermediate A-9. MS for A-9: m/e=326 (M+1).

Step 8

A solution of A-9 (2.00 g, 6.15 mmol), di-tert-butyl dicarbonate (1.46 mL, 6.27 mmol) and triethylamine (2.57 mL, 18.4 mmol) in DCM (30 ml) was stirred at 20° C. for 18 h. The mixture was partitioned between brine (200 mL) and DCM (50 mL). The organic layer was separated, dried over Na₂SO₄, filtered and concentrated in vacuo. The residue was diluted with PE and stirred for 10 min, filtered and dried under vacuum to give A-10. LCMS for A-10: m/e=426 (M+1).

Method 2A

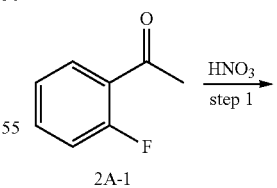

2A-1

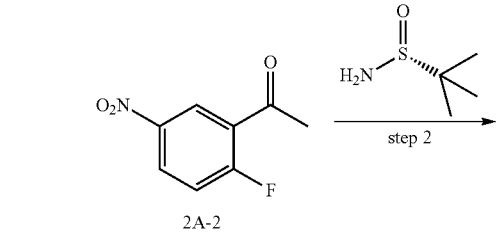

2A-2

-continued

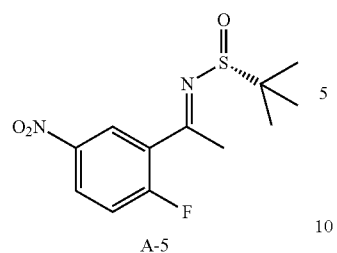

A-5

Step 1

To a mechanically stirred slurry of conc. $H_2SO_4$ (93-98%, 360 mL) at −42° C. were added dropwise T-fluoro-acetophenone 2A-1 (90.0 g, 652 mmol) and a solution of fuming nitric acid (53.1 mL) in conc. $H_2SO_4$ (129 mL). The slurry was stirred for 30 min at −42° C. The mixture was slowly poured onto 1.3 kg of ice. To the mixture was added water (1 L). The product precipitated out of solution. After all of the ice melted, the product was collected via filtration. The solid was dissolved with EtOAc. The organic layer was washed sequentially with 5% $Na_2CO_3$ (2×300 mL), water (300 mL), and brine (300 mL), then dried over $Na_2SO_4$, filtered, and concentrated to give compound 2A-2.

Step 2

To a solution of the acetophenone 2A-2 (115 g, 628 mmol) in THF (900 mL) was added (R)-2-methylpropane-2-sulfinamide (87.7 g, 691 mmol) and Ti(OEt)$_4$ (315 g, 1.38 mole). The solution was heated at reflux for 20 h, cooled to RT, and poured onto ice (3.0 kg). The mixture was stirred for 20 min and then filtered. The organic layer was washed with brine, and dried over $Na_2SO_4$, filtered, and the filtrate was concentrated. The residue was purified by flash chromatography (SiO$_2$, 15% EtOAc in hexanes) to give compound A-5. MS for A-5: m/e=287 (M+1).

Method B

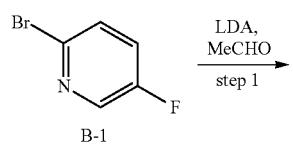

B-1

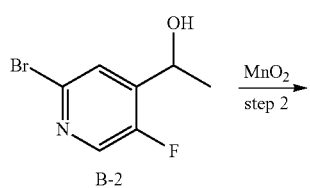

B-2

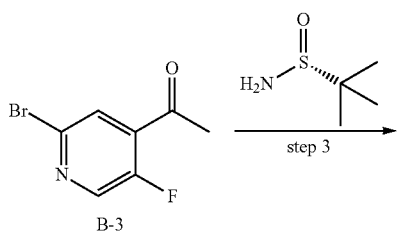

B-3

-continued

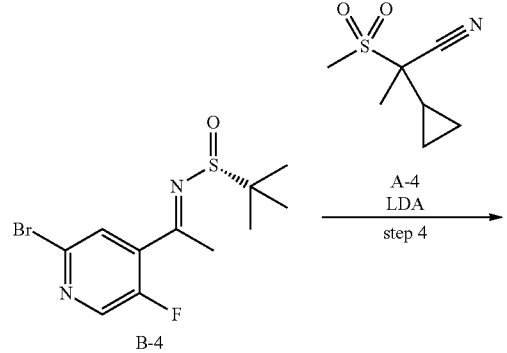

B-4

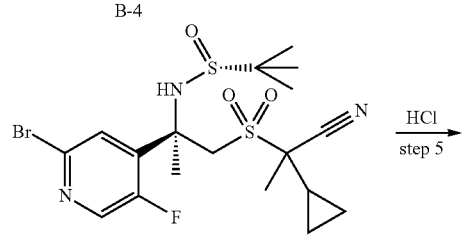

B-5

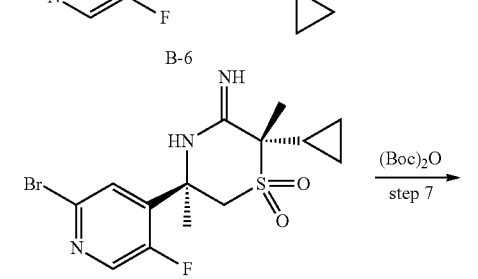

B-6

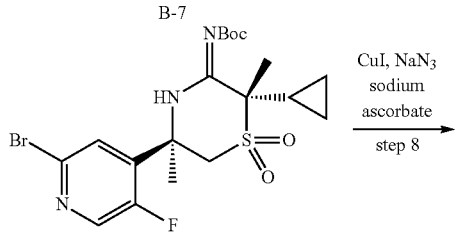

B-7

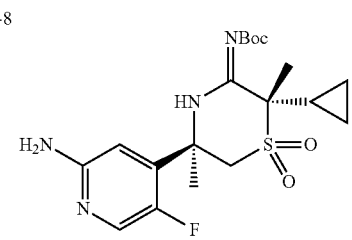

B-8

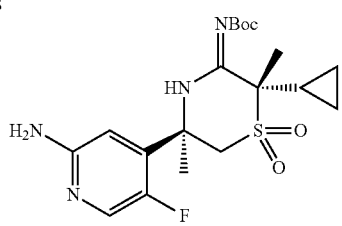

B-9

Step 1

To a solution of 2-bromo-5-fluoropyridine B-1 (50.0 g, 0.290 mol) in THF (300 mL) was added LDA (150 mL, 0.290 mol, 2 M in THF) at −78° C. After stirring at −78° C. for 2 h, acetaldehyde (13.8 g, 0.340 mol) was added and the reaction mixture was allowed to warm to room temperature and stirred at room temperature overnight. The reaction was quenched with saturated aqueous NH₄Cl and extracted with EtOAc. The combined extracts were washed with brine, dried over Na₂SO₄, filtered and concentrated. The residue was purified by column chromatography on silica gel (PE: EtOAc=10:1) to afford compound B-2. MS for B-2: m/e=220 and 222 (M+1).

Step 2

A suspension of 1-(2-bromo-5-fluoropyridin-4-yl)ethanol B-2 (43.0 g, 0.20 mol) and MnO₂ (68.0 g, 0.80 mmol) in CHCl₃ (400 mL) was heated at reflux under N₂ overnight. The reaction mixture was filtered and the filtrate was concentrated. The residue was purified by column chromatography (PE:EtOAc=20:1) to afford compound B-3. MS for B-3: m/e=218 and 220 (M+1).

Step 3

A mixture of 1-(2-bromo-5-fluoropyridin-4-yl)ethanone B-3 (30.0 g, 0.140 mol), (R)-2-methyl-2-propanesulfinamide (25.0 g, 0.210 mol) and Ti(OEt)₄ (63.0 g, 0.280 mol) in THF (300 mL) was heated at reflux overnight. The mixture was quenched by ice-water (150 mL) and filtered. The filtrate was extracted with EtOAc. The combined extracts were washed with water and brine, dried over Na₂SO₄ and filtered. The filtrate was concentrated. The residue was purified by column chromatography (PE:EtOAc=10:1) to afford compound B-4. MS for B-4: m/e=321 and 323 (M+1).

Step 4

To a solution of 2-cyclopropyl-2-(methylsulfonyl)propanenitrile A-4 (16.0 g, 90.0 mmol) in THF (100 mL) was added LDA (45.0 mL, 90.0 mmol, 2 M in THF) at −78° C. After being stirred at −78° C. for 1 h, a solution of B-4 (24.0 g, 80.0 mmol) in THF (100 mL) was added. The reaction mixture was stirred at −78° C. for 3 h, quenched with saturated NH₄Cl, and extracted with EtOAc. The combined organic layers were washed with water and brine, dried over Na₂SO₄ and filtered. The filtrate was concentrated. The residue was purified by silica column chromatography (PE: EtOAc=10:1) to afford compound B-5. MS for B-5: m/e=494 and 496 (M+1).

Step 5

To a solution of B-5 (48.0 g, 97.2 mmol) in DCM (200 mL) was added HCl in dioxane (20.0 mL, 4 M) at 0° C. After being stirred at room temperature for 3 h, MeOH (10 mL) was added to quench the reaction. The mixture was concentrated, basified with saturated aqueous NaHCO₃, and extracted with DCM. The combined extracts were washed with brine, dried over Na₂SO₄ and filtered. The filtrate was concentrated. The residue was purified by silica column chromatography (PE:EtOAc=9:1 to 1:1) to afford compound B-6. MS for B-6: m/e=390 and 392 (M+1).

Step 6

To a solution of B-6 (4.00 g, 10.3 mmol) in EtOH (150 mL) was added CuBr (2.90 g, 20.2 mmol) at room temperature. The mixture was heated at reflux for 40 h, cooled to room temperature, conc. NH₃.H₂O (4 mL) was added to quench the reaction, and the mixture was concentrated. The residue was partitioned between water (40 mL) and EtOAc (100 mL), the layers were separated, and the aqueous layer extracted with EtOAc. The combined organic extracts were washed with brine, dried over Na₂SO₄ and concentrated. The residue was purified by SFC (column: AD 300 mm×50 mm, 10 μm; mobile phase: 45% EtOH NH₃H₂O; 200 mL/min; mobile phase B: acetonitrile) to afford compound B-7. MS for B-7: m/e=390 and 392 (M+1).

Step 7

To a rt solution of B-7 (18.5 g, 47.4 mmol) in DCM (300 mL) were added di-tert-butyl dicarbonate (11.4 g, 52.1 mmol) followed by triethylamine (5.76 g, 56.9 mmol) and the mixture was stirred at 25° C. for 5 h. The mixture was washed with water (50 mL×3), brine (50 mL), dried over Na₂SO₄ and concentrated in vacuo to afford compound B-8. MS for B-8: m/e=490 and 492 (M+1).

Step 8

To a mixture of Intermediate B-8 (8.00 g, 16.3 mmol) in EtOH (80 mL)/Water (25 mL) were added N-,N-dimethylcyclohexane-1,2-diamine (2.32 g, 16.3 mmol), copper(I) iodide (1.55 g, 8.16 mmol), (R)-5-(1,2-dihydroxyethan-1-ylium-1-yl)-4-hydroxy-2-oxo-2,5-dihydrofuran-3-olate, sodium salt (1.61 g, 8.16 mmol), and sodium azide (6.36 g, 98.0 mmol). The mixture was stirred at 70° C. for 2 h, then cooled to rt and the pH adjusted to 9 by addition of Na₂CO₃ solution (aq, 5 M, 60 mL). The resulting mixture was washed with NH₃H₂O (35%, 40 mL), then extracted with EtOAc (30 mL×3). The combined organic layers were washed with brine (40 mL), dried over Na₂SO₄ and concentrated. The residue was purified by silica column chromatography (PE:EtOAc=8:1 to 2:1) to afford compound B-9. MS for B-9: m/e=427 (M+1).

Method C

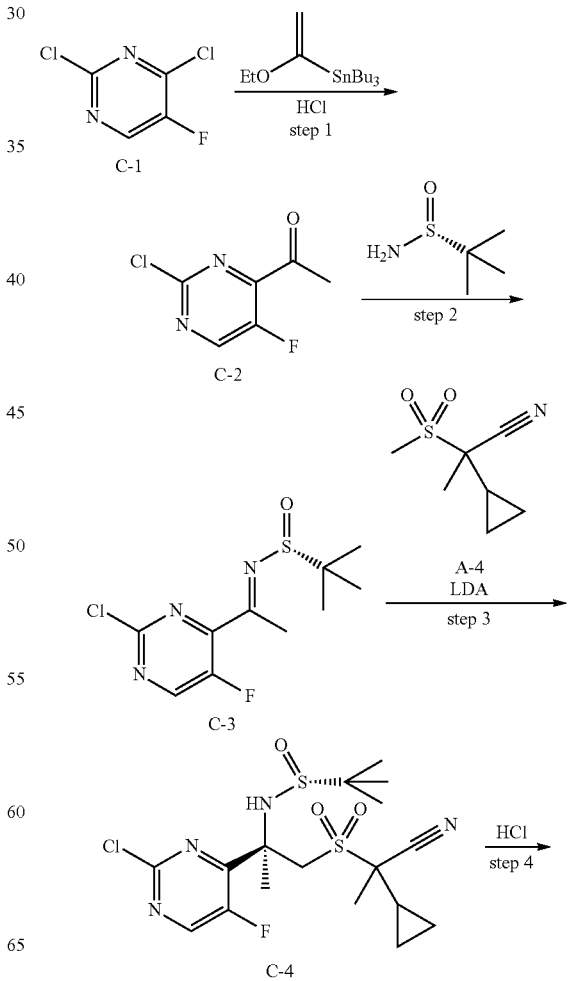

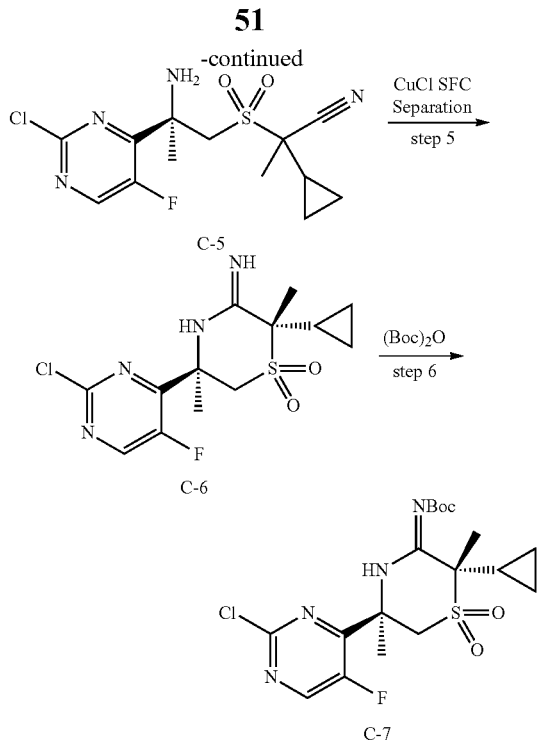

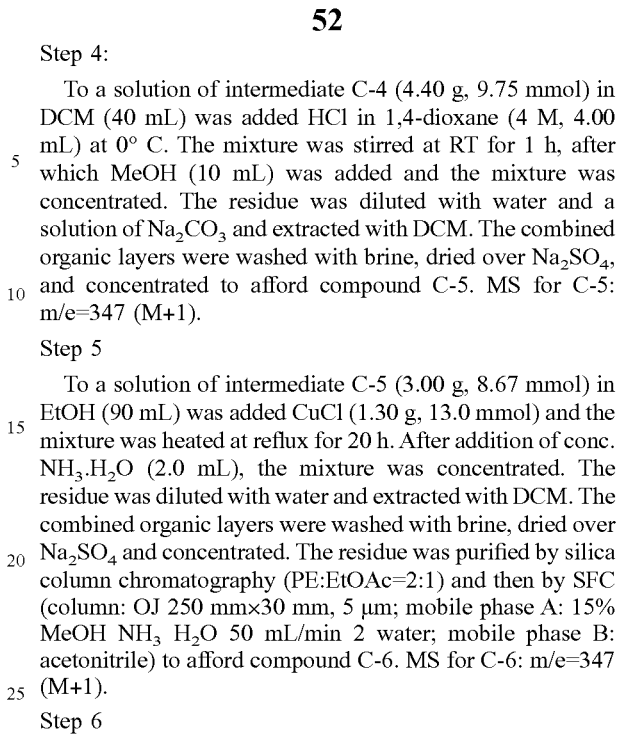

Step 1

To a solution of 2,4-dichloro-5-fluoropyrimidine C-1 (5.00 g, 30.0 mmol) in DMF (60 mL) were added tributyl (1-ethoxyvinyl)stannane (17.5 g, 33.0 mmol) and Pd(PPh$_3$)$_2$Cl$_2$ (426 mg, 0.600 mmol). The mixture was stirred at 70° C. for 1 h, then cooled to rt, treated with solid KF and the mixture was stirred at RT for 0.5 h. The mixture was filtered, diluted with water and extracted with EtOAc. The organic layer was washed with brine, dried over Na$_2$SO$_4$, filtered and concentrated. The residue was diluted with THF (10 mL) and HCl/H$_2$O (10 mL, 6 N). The mixture was stirred at 30° C. for 2 h, diluted with a solution of Na$_2$CO$_3$ in H$_2$O, and extracted with EtOAc. The combined extracts were washed with brine, dried over Na$_2$SO$_4$, concentrated and the residue was purified by silica column chromatography (PE:EtOAc=60:1) to afford compound C-2. MS for C-2: m/e=175 (M+1).

Step 2

To a solution of Intermediate C-2 (3.90 g, 22.0 mmol) in THF (40 mL) were added (R)-2-methylpropane-2-sulfinamide (3.20 g, 26.0 mmol) and Ti(OEt)$_4$ (10.2 g, 44.8 mmol). The mixture was stirred at 80° C. for 2 h, poured into water, and stirred at RT for 0.5 h. The mixture was filtered and the filtrate was extracted with EtOAc. The combined organic extracts were washed with brine, dried over Na$_2$SO$_4$, and concentrated. The residue was purified by silica column chromatography (PE:EtOAc=100:1) to afford compound C-3. MS for C-3: m/e=278 (M+1).

Step 3:

To a solution of Intermediate A-4 (568 mg, 3.30 mmol) in THF (10 mL) was added LDA (1.8 mL, 3.6 mmol, 2.0 M in THF) at −78° C. After stirring at −78° C. for 1 h. Intermediate C-3 (1.00 g, 3.60 mmol) in THF (10 mL) was added at −78° C. The mixture was stirred at −78° C. for 4 h, quenched with water, and extracted with EtOAc. The combined organic layers were washed with brine, dried over Na$_2$SO$_4$, and concentrated. The residue was purified by silica column chromatography (PE:EtOAc=3:1) to afford compound C-4. MS for C-4: m/e=451 (M+1).

Step 4:

To a solution of intermediate C-4 (4.40 g, 9.75 mmol) in DCM (40 mL) was added HCl in 1,4-dioxane (4 M, 4.00 mL) at 0° C. The mixture was stirred at RT for 1 h, after which MeOH (10 mL) was added and the mixture was concentrated. The residue was diluted with water and a solution of Na$_2$CO$_3$ and extracted with DCM. The combined organic layers were washed with brine, dried over Na$_2$SO$_4$, and concentrated to afford compound C-5. MS for C-5: m/e=347 (M+1).

Step 5

To a solution of intermediate C-5 (3.00 g, 8.67 mmol) in EtOH (90 mL) was added CuCl (1.30 g, 13.0 mmol) and the mixture was heated at reflux for 20 h. After addition of conc. NH$_3$.H$_2$O (2.0 mL), the mixture was concentrated. The residue was diluted with water and extracted with DCM. The combined organic layers were washed with brine, dried over Na$_2$SO$_4$ and concentrated. The residue was purified by silica column chromatography (PE:EtOAc=2:1) and then by SFC (column: OJ 250 mm×30 mm, 5 µm; mobile phase A: 15% MeOH NH$_3$ H$_2$O 50 mL/min 2 water; mobile phase B: acetonitrile) to afford compound C-6. MS for C-6: m/e=347 (M+1).

Step 6

To a stirred solution of C-6 (285 mg, 0.82 mmol) and triethylamine (166 mg, 1.64 mmol) in DCM (4 mL) at RT was added di-tert-butyl dicarbonate (179 mg, 0.82 mmol). The mixture was stirred at 25° C. overnight, then diluted with water and DCM and the layers separated. The organic layer was dried over Na$_2$SO$_4$ and concentrated to afford compound C-7, which was used in the next step directly. MS for C-7: m/e=447 (M+1).

Method D

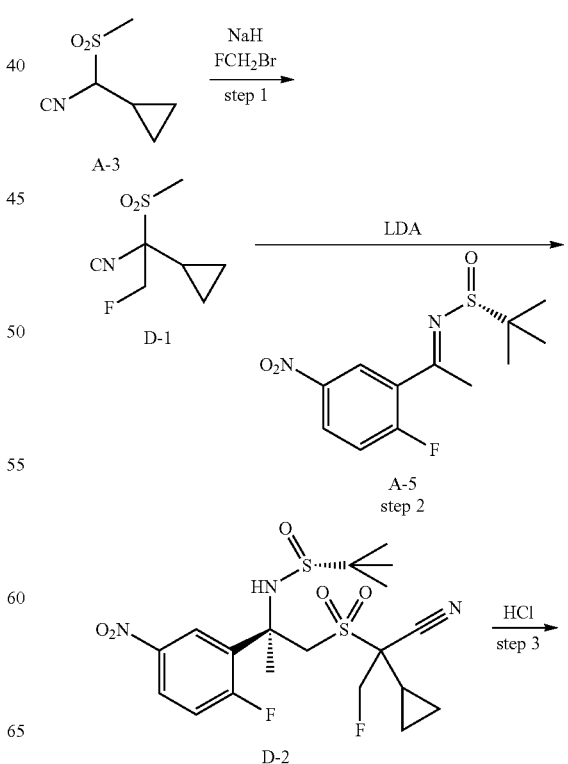

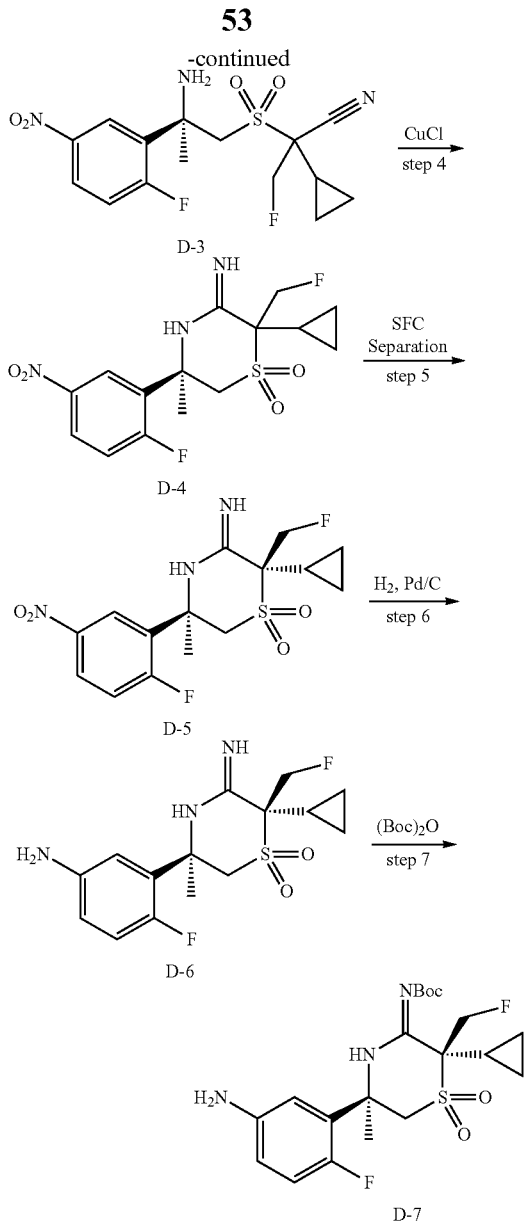

Step 1

To a suspension of NaH (3.00 g, 75.0 mmol, 60%) in THF (400 mL) at 0° C. was added a solution of 2-cyclopropyl-2-(methylsulfonyl)acetonitrile A-3 (10.0 g, 62.5 mmol) in THF (200 mL). The mixture was stirred at 0° C. for 1.5 h, followed by addition of bromofluoromethane (14.0 g, 125 mmol). The reaction mixture was stirred at 0° C. for 10 min, then warmed to RT and stirred overnight. The resulting mixture was quenched with aq. NH$_4$Cl and extracted with EtOAc. The combined organic extracts were washed with water and brine, dried over Na$_2$SO$_4$, filtered, and concentrated. The residue was purified by silica column chromatography (PE:EtOAc=5:1) to afford compound D-1. $^1$H NMR for D-1 (300 MHz, CDCl$_3$): δ ppm 4.87~4.94 (m, 0.5H), 4.69~4.82 (m, 1H), 4.59 (d, J=10.2 Hz, 0.5H), 3.05 (s, 3H), 1.10 (d, J=5.1 Hz, 1H), 0.80~0.92 (m, 2H), 0.67~0.74 (m, 1H), 0.47~0.59 (m, 1H).

Step 2

To a solution of 2-cyclopropyl-3-fluoro-2-(methylsulfonyl)propanenitrile D-1 (10.0 g, 52.1 mmol) in THF (400 mL) at −78° C. was added LDA (31.3 mL, 62.5 mmol, 2.0 M in THF) dropwise. After being stirred at −78° C. for 1 h, a solution of intermediate A-5 (14.9 g, 52.1 mmol) in THF (200 mL) was added dropwise. The mixture was stirred for another 5 h at −78° C., then quenched with aq. NH$_4$Cl and extracted with EtOAc. The combined organic layers were dried over Na$_2$SO$_4$ and concentrated. The residue was purified by silica column chromatography (PE:EtOAc=1:1) to afford compound D-2. MS for D-2: m/e=478 (M+1).

Step 3

To a solution of intermediate D-2 (14.0 g, 29.4 mmol) in DCM/MeOH (200 mL/10 mL) was added HCl in dioxane (20 mL, 4 M) at 0° C. The mixture was then warmed to RT and stirred for 2 h. The reaction mixture was concentrated, redissolved in MeOH, neutralized with aq. NaHCO$_3$ at 0° C. and extracted with DCM. The organic layers were dried over Na$_2$SO$_4$ and concentrated to afford compound D-3. MS for D-3: m/e=374 (M+1).

Step 4

To a solution of intermediate D-3 (10.5 g, 28.1 mmol) in EtOH (150 mL) was added CuCl (5.56 g, 56.2 mmol). The mixture was heated at reflux overnight. The resulting suspension was treated with 15% aq. NaOH and extracted with DCM. The organic layer was washed with brine, dried over Na$_2$SO$_4$ and concentrated, then purified by silica column chromatography (PE:EtOAc=3:1) to afford compound D-4. MS for D-4: m/e=374 (M+1).

Step 7

Intermediate D-4 (10.5 g) was resolved by SFC column (AD 300 mm×50 mm, 10 μm, A: supercritical CO$_2$, B: IPA (0.1% NH$_3$H$_2$O), A:B=60:40) to afford compound D-5. $^1$H NMR for D-5 (400 MHz, MeOD): δ ppm 8.35~8.39 (m, 1H), 8.22 (dt, J=8.8, 3.5 Hz, 1H), 7.36 (dd, J=11.3, 9.0 Hz, 1H), 4.71~4.95 (m, 2H), 3.53~3.92 (m, 2H), 1.70 (s, 3H), 1.23~1.32 (m, 1H), 0.66~0.83 (m, 4H).

Step 6

To a solution of intermediate D-5 (1.00 g, 2.68 mmol) in MeOH (100 mL) was added Pd/C (300 mg, 10%) and the mixture was stirred at RT under H$_2$ balloon for 1 h. The reaction mixture was filtered through Celite and the filtrate was concentrated to afford compound D-6. MS for D-6: m/e=344 (M+1).

Step 7

To a stirred solution of intermediate D-6 (250 mg, 0.730 mmol) and triethylamine (74.0 mg, 0.730 mmol) in DCM (8 mL) was added di-tert-butyl dicarbonate (160 mg, 0.730 mmol). The mixture was stirred at 25° C. overnight, then diluted with water and extracted with DCM. The combined organic extracts were dried over Na$_2$SO$_4$ and concentrated. The residue was purified by silica column chromatography (PE:EtOAc=3:1) to afford compound D-7. MS for D-7: m/e=444 (M+1).

Method E

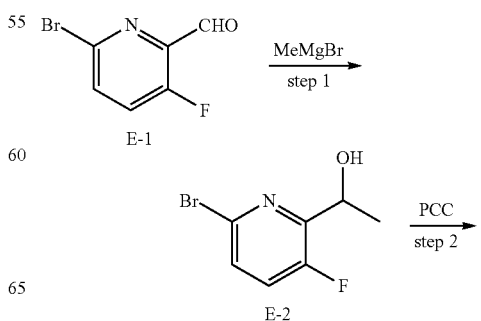

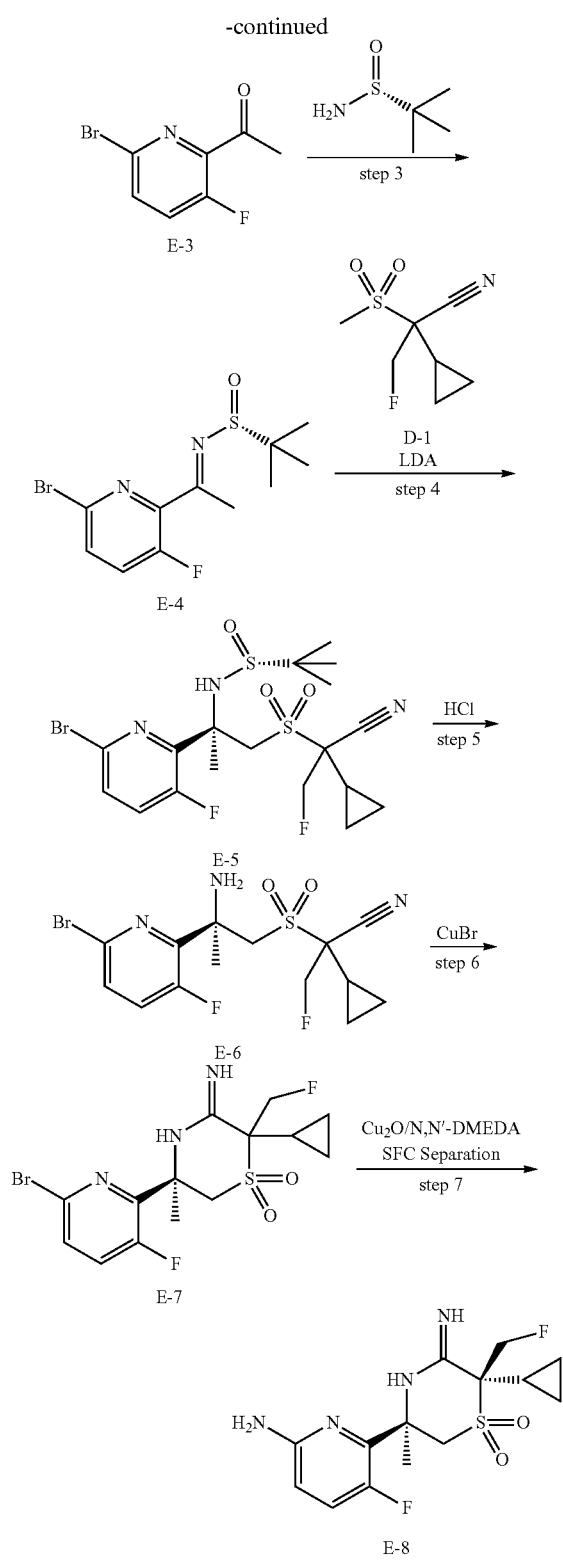

Step 1

To a stirred solution of 6-bromo-3-fluoropicolinaldehyde E-1 (10.0 g, 49.0 mmol) in 200 mL of THF was added 18.0 mL of MeMgBr (3.0 M in ether, 54.0 mmol) at −78° C. dropwise over a period of 35 min. The reaction was stirred at −78° C. for 3 hrs, then warmed to 0° C. and stirred at 0° C. for additional 1 h. The mixture was quenched with 150 mL of saturated aq. NH$_4$Cl at 0° C. and extracted with three 200 mL portions of EtOAc. The combined organic extracts were concentrated; the residue was purified by flash chromatography (220 g of SiO$_2$: 0 to 30% EtOAc in hexane) to give compound E-2. MS for E-2: m/e=220 and 222 (M+1).

Step 2:

To a solution of compound E-2 (8.74 g, 39.7 mmol) in 175 mL of CH$_2$Cl$_2$ at room temperature were added 21.4 g (99.0 mmol) of pyridinium chlorochromate and 7.50 g of Celite. The reaction mixture was stirred at room temperature for 25 h and then filtered through Celite and washed with CH$_2$Cl$_2$. The CH$_2$Cl$_2$ filtrate was concentrated; the residue was purified by flash chromatography (220 g of SiO$_2$: 0 to 10% EtOAc in hexane) to give compound E-3. MS for E-3: m/e=218 and 220 (M+1).

Step 3

A mixture of E-3 (9.22 g, 42.3 mmol), (R)-(+)-2-methyl-2-propanesulfinamide (9.23 g, 76.0 mmol), titanium (IV) ethoxide (19.3 g, 85.0 mmol) in THF (90 mL) was heated at reflux under nitrogen for 3 h. The mixture was cooled and poured into ice water (300 mL) and stirred 10 min, after which EtOAc (300 mL) was added and stirring continued for 20 min. The mixture was filtered through Celite and the layers were separated. The aqueous layer was extracted with EtOAc (2×) and the combined organic layers were dried (MgSO$_4$), filtered and concentrated. The resulting residue was purified by flash chromatography (330 g SiO$_2$, 0 to 30% EtOAc in hexanes) to provide E-4. MS for E-4: m/e=321 and 323 (M+1).

Step 4

To a solution of 2-cyclopropyl-3-fluoro-2-(methylsulfonyl)propanenitrile D-1 (4 g, 21 mmol) in THF (150 mL) at −78° C. was added LDA (11.5 mL, 23 mmol, 2.0 M in hexane) dropwise and the mixture was stirred for 1 h at −78° C. Then a solution of intermediate E-4 (6.70 g, 21.0 mmol) in THF (15 mL) was added and the mixture was stirred for 6 h at −78° C. The mixture was quenched with saturated NH$_4$Cl and extracted with EtOAc. The combined organic layers were washed with water and brine, dried over NaSO$_4$ and purified by silica column chromatography (PE:EA=20:1 to 10:1 to 3:1) to afford compound E-5. MS for E-5: m/e=512 and 514 (M+1).

Step 5

To a solution of intermediate E-5 (6.50 g, 12.7 mmol) in DCM (200 mL) and MeOH (5 mL) at 0° C. was added HCl in 1,4-dioxane (4 M, 40 mL). The mixture was stirred for 1 h and concentrated. The residue was diluted with Na$_2$CO$_3$ solution and extracted with DCM. The combined organic layers were dried over Na$_2$SO$_4$ and concentrated to afford compound E-6. MS for E-6: m/e=408 and 410 (M+1).

Step 6

A mixture of intermediate E-6 (6.50 g, 15.9 mmol) and CuBr (4.30 g, 30.0 mmol) in EtOH (200 mL) was stirred at 100° C. for 20 h, then cooled and concentrated. The residue was diluted with DCM and NH$_3$ H$_2$O (10%), filtered; the filtrate was extracted with EtOAc. The combined organic layers were dried over Na$_2$SO$_4$ and concentrated to afford compound E-7. MS for E-7: m/e=408 and 410 (M+1).

Step 7

A solution of intermediate E-7 (4.80 g, 11.7 mmol), Cu$_2$O (172 mg 1.20 mmol), N,N-DMEDA (211 mg, 2.40 mmol), K$_2$CO$_3$ (331 mg, 2.40 mmol) and NH$_4$OH (150 mL) in a sealed tube was stirred at 65° C. for 16 h. The mixture was filtered and the filtrate was concentrated. The residue was purified by SFC (Column: Chiralpak AD-3 50×4.6 mm I.D., 3 μm; Mobile phase: 40% methanol (0.05% DEA) in CO$_2$;

Flow rate: 4 mL/min; Wave length: 220 nm) to afford compound E-8. MS for E-8: m/e=345 (M+1).

Method F

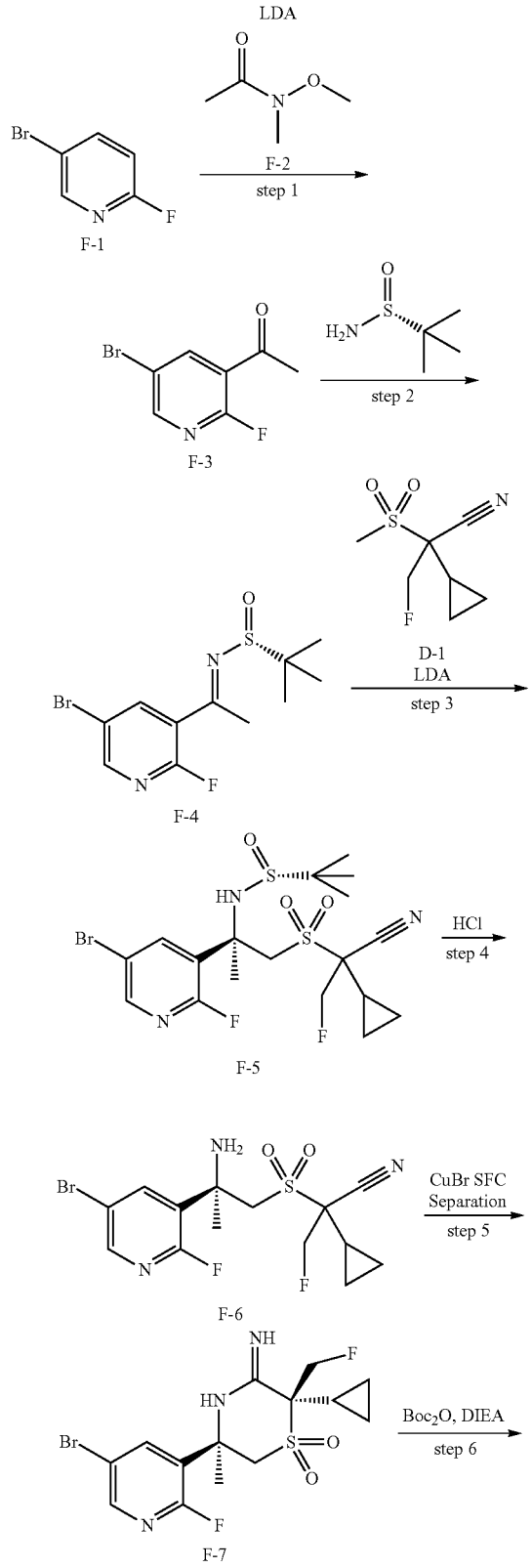

Step 1

To a solution of diisopropylamine (16.2 mL, 114 mmol) in 25 mL THF at −78° C. was added dropwise n-butyllithium (2.5 M in hexanes, 45.5 mL) and the mixture stirred 1 h at −78° C. following complete addition. The resulting solution was added dropwise over 50 min. to a stirred solution of F-1 in 75 mL THF at −78° C. and the mixture stirred 1 h at −78° C. A solution of F-2 in 20 mL THF was then added and the mixture was allowed to warm slowly to rt, stirring 12 h. The reaction mixture was quenched with 1.0 N HCl and diluted with EtOAc. The organic layer was separated and washed sequentially with water and brine, dried ($Na_2SO_4$), filtered and concentrated. The resulting residue was purified by flash chromatography (220 g $SiO_2$; 0 to 20% EtOAc in hexanes) to provide F-3. MS for F-3: m/e=218 and 220 (M+1).

Step 2

A mixture of F-3 (13.0 g, 59.6 mmol), (R)-(+)-2-methyl-2-propanesulfinamide (14.5 g, 119 mmol), titanium (IV) ethoxide (31.0 g, 136 mmol), and 100 mL THF was heated at reflux under nitrogen for 12 h. The mixture was cooled and poured into ice water (300 mL) and EtOAc (300 mL) and stirred for 1 h. The mixture was filtered through Celite and the layers were separated. The organic layer was washed with brine, dried ($Na_2SO_4$), filtered and concentrated to provide F-4 which was used without further purification. MS for F-4: m/e=321 and 323 (M+1).

Step 3

To a solution of 2-cyclopropyl-3-fluoro-2-(methylsulfonyl)propanenitrile D-1 (1.49 g, 7.78 mmol) in THF (30 mL) at −78° C. was added LDA (4.67 mL, 9.34 mmol, 2.0 M in THF) dropwise, then stirred at −78° C. for 1 h. A solution of intermediate F-4 in THF (10 mL) was added and the resulting mixture was stirred at −78° C. for another 5 h, then quenched with aq. $NH_4Cl$ and extracted with EtOAc. The combined organic layers were dried over $Na_2SO_4$, filtered and concentrated, then purified by silica column chromatography (PE:EA=3:1) to afford compound F-5. MS for F-5: m/e=512 and 514 (M+1).

Step 4

To a solution of sulfinamide F-5 (1.92 g, 3.75 mmol) in DCM/MeOH (40 mL/40 mL) was added HCl in dioxane (4 M, 8.0 mL) at 0° C. The mixture was stirred at 25° C. for 40 min and then concentrated. The resulting residue was diluted with a solution of $Na_2CO_3$ and extracted with DCM. The combined organic layers were washed with brine, dried over Na₂SO₄, filtered and concentrated to afford compound F-6. MS for F-6: m/e=408 and 410 (M+1).

Step 5

A suspension of intermediate F-6 (1.53 g, 3.75 mmol) and CuBr (1.08 g, 7.50 mmol) in EtOH (30 mL) was heated at reflux under N₂ for 36 h. The reaction mixture was diluted with NH₃.H₂O (20 mL, 30%) and concentrated. The resulting residue was diluted with water and extracted with EtOAc. The combined organic layers were washed with brine, dried over Na₂SO₄, filtered and concentrated. The residue was purified by silica column (PE:EtOAc=10:1 to 3:1) and then by SFC (Chiralpak AD-H 250×4.6 mm I.D., 5 μm; Mobile phase: methanol (0.05% DEA) in CO₂ from 5% to 40%; Flow rate: 2.35 mL/min) to afford compound F-7. MS for F-7: m/e=408 and 410 (M+1).

Step 6

To a stirred solution of (2S,5R)-5-(5-bromo-2-fluoropyridin-3-yl)-2-cyclopropyl-2-(fluoromethyl)-3-imino-5-methylthiomorpholine 1,1-dioxide F-7 (2.92 g, 7.15 mmol) in DCM (30 mL) were added Boc₂O (3.12 g, 14.3 mmol) and DIEA (1.85 g, 14.3 mmol). The mixture was stirred at 25° C. for 12 h, washed with brine, dried over Na₂SO₄, filtered, and concentrated. The resulting residue was purified by silica column chromatography (PE:EtOAc=3:1) to afford compound F-8. MS for F-8: m/e=508 and 510 (M+1).

Step 7

To a mixture intermediate F-8 (4.44 g, 8.73 mmol) in EtOH/H₂O (30 mL/10 mL) were added NaN₃ (4.54 g, 69.9 mmol), CuI (0.832 g, 4.37 mmol), L-ascorbic acid sodium salt (1.24 g, 8.73 mmol), and cyclohexanedimethyldiamine (1.24 g, 8.73 mmol) at 25° C. under N₂ and the mixture warmed at 55° C. and stirred for 1 h. The mixture was adjusted to pH 9 by Na₂CO₃ (aq) and washed with NH₃.H₂O, then extracted with DCM. The organic layer was washed with brine, dried over Na₂SO₄, filtered and concentrated. The residue was purified by silica column chromatography (PE:EtOAc=3:1) to afford compound F-9. MS for F-9: m/e=445 (M+1).

Method 2F

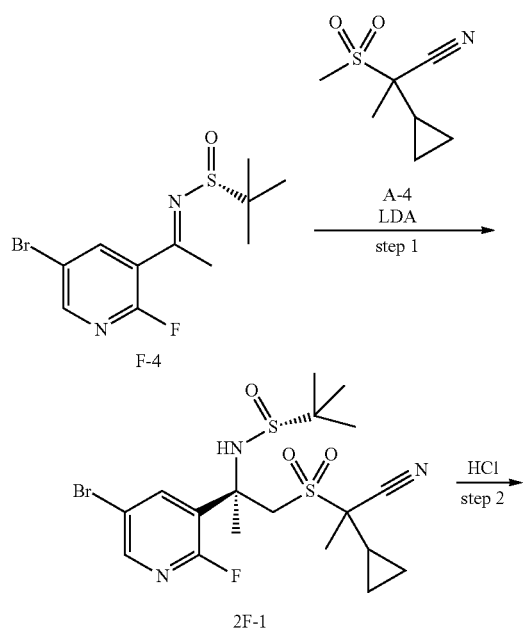

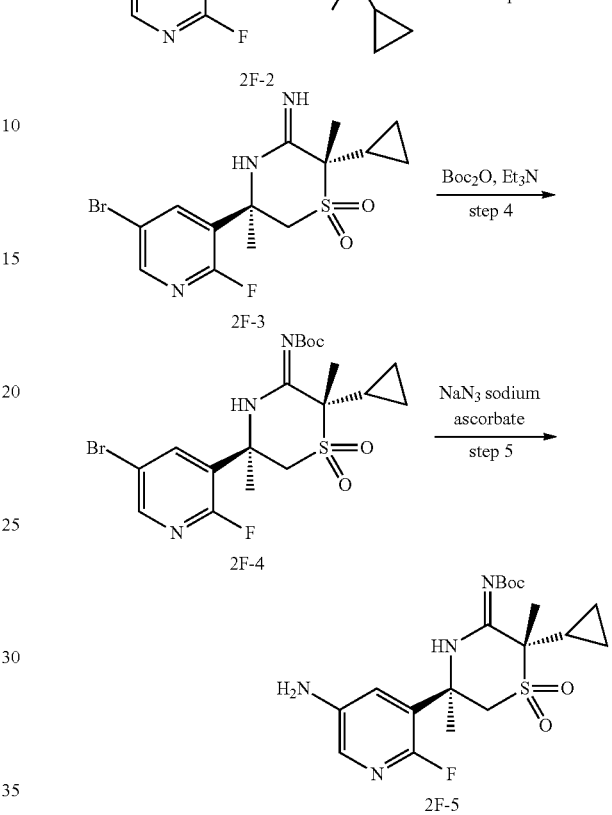

Step 1

To a solution of 2-cyclopropyl-2-(methylsulfonyl)propanenitrile A-4 (5.00 g, 28.9 mmol) in THF (100 mL) at −78° C. was added LDA (17.3 mL, 34.6 mmol, 2.0 M in THF) dropwise, then stirred at −78° C. for 1 h. A solution of intermediate F-4 (7.42 g, 23.1 mmol) in THF (60 mL) was added and the resulting mixture was stirred at −78° C. for another 4 h, then quenched with aq. NH₄Cl and extracted with EtOAc. The combined organic layers were dried over Na₂SO₄, filtered and concentrated, then purified by silica column chromatography (PE:EA=3:1) to afford compound 2F-1. MS for 2F-1: m/e=494 and 496 (M+1).

Step 2

To a solution of sulfinamide 2F-1 (20.0 g, 40.4 mmol) in DCM (200 mL) was added HCl in dioxane (4 M, 20.0 mL) at 0° C. The mixture was stirred at 25° C. for 2 h and then concentrated. The resulting residue was diluted with a solution of Na₂CO₃ and extracted with DCM. The combined organic layers were washed with brine, dried over Na₂SO₄, filtered and concentrated to afford compound 2F-2. MS for 2F-2: m/e=390 and 392 (M+1).

Step 3

A suspension of intermediate 2F-2 (9.00 g, 23.1 mmol) and CuBr (6.62 g, 42.1 mmol) in EtOH (200 mL) was heated at reflux under N₂ for 48 h. The reaction mixture was diluted with NH₃.H₂O (20 mL, 30%) and concentrated. The resulting residue was diluted with water and extracted with EtOAc. The combined organic layers were washed with brine, dried over Na₂SO₄, filtered and concentrated. The residue was purified by silica column (PE:EtOAc=2:1) and then by SFC (Chiralpak AD-H 250×4.6 mm I.D., 5 μm; Mobile phase: isopropanol (0.05% DEA) in $CO_2$ from 5% to 40%; Flow rate: 2.5 mL/min) to afford compound 2F-3. MS for 2F-3: m/e=390 and 392 (M+1).

Step 6

To a stirred solution of 2F-3 (5.00 g, 12.8 mmol) in DCM (70 mL) were added $Boc_2O$ (5.59 g, 25.6 mmol) and TEA (2.59 g, 25.6 mmol). The mixture was stirred at 25° C. for 5 h, washed with brine, dried over $Na_2SO_4$, filtered, and concentrated. The resulting residue was purified by silica column chromatography (PE:EtOAc=12:1) to afford compound 2F-4. MS for 2F-4: m/e=490 and 492 (M+1).

Step 7

To a mixture intermediate 2F-4 (2.00 g, 4.08 mmol) in $EtOH/H_2O$ (35 mL/15 mL) were added $NaN_3$ (2.12 g, 32.6 mmol), CuI (0.388 g, 2.04 mmol), L-ascorbic acid sodium salt (0.404 g, 2.04 mmol), and cyclohexanedimethyldiamine (0.580 g, 2.08 mmol) at 25° C. under $N_2$ and the mixture warmed at 50° C. and stirred for 2 h. The mixture was adjusted to pH 9 by $Na_2CO_3$ (aq) and washed with $NH_3.H_2O$, then extracted with DCM. The organic layer was washed with brine, dried over $Na_2SO_4$, filtered and concentrated. The residue was purified by silica column chromatography (PE:EtOAc=3:1) to afford compound 2F-5. MS for 2F-5: m/e=427 (M+1).

Method G

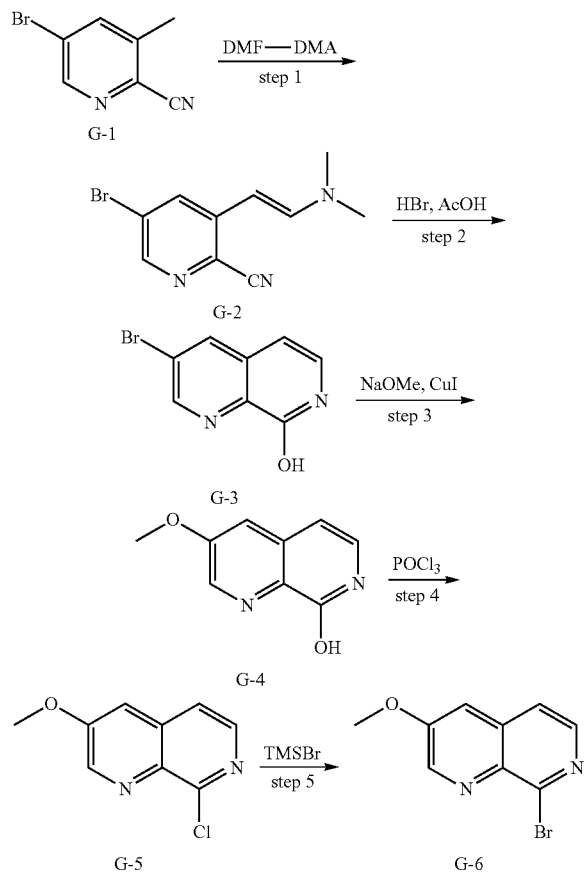

Step 1

To a solution of 5-bromo-3-methylpicolinonitrile G-1 (5.00 g, 25.4 mmol) in DMF (30 mL) was added DMF-DMA (6.80 mL, 50.8 mmol) at room temperature. The mixture was stirred at 145° C. overnight, then cooled and concentrated. The resulting residue was purified by column chromatography on silica (PE:EtOAc=50:1~10:1) to afford compound G-2. MS for G-2: m/e=252 and 254 (M+1).

Step 2

To a mixture of 5-bromo-3-(2-(dimethylamino)vinyl)picolinonitrile G-2 (1.10 g, 4.36 mmol) in EtOH (9 mL) was added dropwise 40% aq. HBr (9 mL) at room temperature. The mixture was heated at reflux for 4 h, then cooled to room temperature. The precipitated solid was filtered and the filter cake was neutralized with sat. sodium bicarbonate until gas evolution ceased. The mixture was filtered and the filter cake was dried to afford compound G-3. MS for G-3: m/e=225 and 227 (M+1).

Step 3

A mixture of 3-bromo-1,7-naphthyridin-8-ol G-3 (2.0 g, 8.89 mmol), sodium methanolate (2.40 g, 44.4 mmol) and copper(I) iodide (846 mg, 4.44 mmol) in DMF (20 mL) was stirred at 100° C. for 16 h under $N_2$. Then mixture was concentrated to afford compound G-4. MS for G-4: m/e=177 (M+1).

Step 4

Intermediate G-4 (2.00 g, 7.95 mmol) was added to $POCl_3$ (30 mL, 322 mmol) and the mixture was stirred at 100° C. for 3 h. The mixture was concentrated and the residue was poured into water slowly, neutralized with solid $Na_2CO_3$, and extracted with EtOAc. The combined organic extracts were washed with brine, dried over $Na_2SO_4$, concentrated, and purified by silica column chromatography (PE:EtOAc=10:1~5:1) to afford compound G-5. MS for G-5: m/e=195 (M+1).

Step 5

To a suspension of intermediate G-5 (900 mg, 4.62 mmol) in acetonitrile (10 mL) was added bromotrimethylsilane (708 mg, 46.2 mmol). The mixture was stirred at 80° C. for 16 h, then the resulting solid was collected by filtration and washed with $Na_2CO_3$ (aq.) (10 mL) to afford compound G-6. MS for G-6: m/e=239 and 241 (M+1).

Method 2G

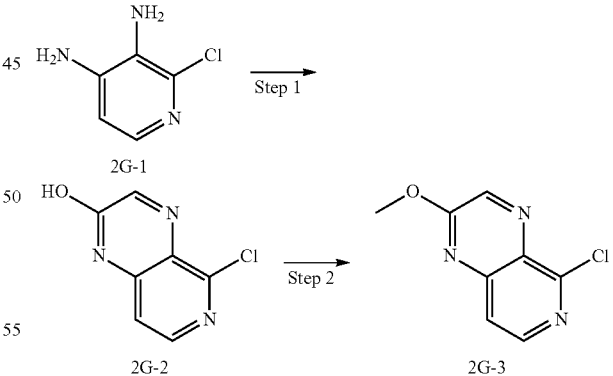

Step 1

To a stirred solution of 2-chloropyridine-3,4-diamine 2G-1 (1.36 g, 9.45 mmol) in EtOH (95 ml) was added glyoxylic acid monohydrate (4.35 g, 47.3 mmol) at RT. The reaction stirred at 70° C. for 15 h, then cooled to RT and was concentrated. The residue was purified directly without workup by silica column chromatography (0-100% EtOAc in DCM) to give compound 2G-2. MS for 2G-2: m/e=182 (M+1).

Step 2

Intermediate 2G-2 (1.24 g, 6.83 mmol) was dissolved in DCM (30.7 mL) and MeOH (3.41 mL). To this solution at 0° C. was added TMS-diazomethane (0.5 M in diethyl ether, 5.12 mL, 10.24 mmol) slowly. After being stirred for 2 h at RT, the reaction was cooled to 0° C. and acetic acid (1.96 mL, 34.1 mmol) was added. After 30 min, the reaction was quenched with saturated aqueous sodium bicarbonate and extracted with DCM three times. The combined organic layers were dried with magnesium sulfate, filtered, concentrated and the residue was purified by silica column chromatography (0-30% EtOAc in hexanes) to afford compound 2G-3. MS for 2G-3: m/e=196 (M+1).

Method 3G

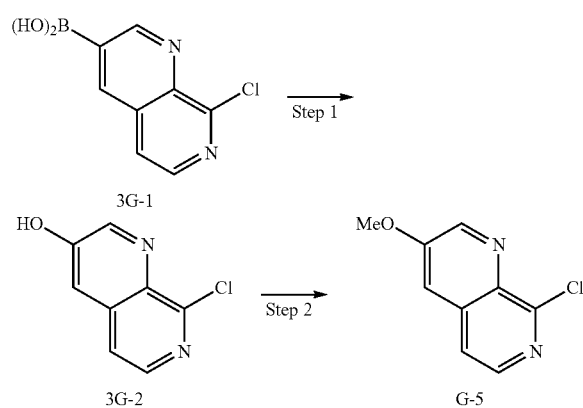

Step 1

To a solution of (8-chloro-1,7-naphthyridin-3-yl)boronic acid 3G-1 (1.00 g, 4.80 mmol) in acetic acid (19.2 mL) was added hydrogen peroxide (2.10 mL, 24.0 mmol). The reaction was stirred at RT for 4 h, and poured over ice. Saturated sodium bicarbonate solution was added slowly until the aqueous layer is slightly basic. The resulting mixture was extracted with EtOAc three times. The combined organic extracts were dried with magnesium sulfate, filtered, and concentrated. The residue was purified by silica column chromatography (0-10% MeOH in DCM) to give compound 3G-2. MS for 3G-2: m/e=181 (M+1).

Step 2

To a stirred solution of intermediate 3G-2 (0.361 g, 2.00 mmol) and cesium carbonate (0.977 g, 3.00 mmol) in DMF (8.00 ml) was added methyl iodide (0.187 ml, 3.00 mmol). The reaction mixture was stirred at room temperature for 2 h, then diluted with water and extracted with DCM three times. The combined organic layers were dried with magnesium sulfate, filtered, and concentrated. The residue was purified by silica column chromatography (0-100% EtOAc in Hexane) to give compound G-5. MS for G-5: m/e=195 (M+1).

Method 4G

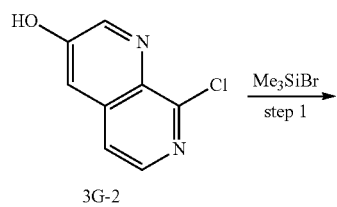

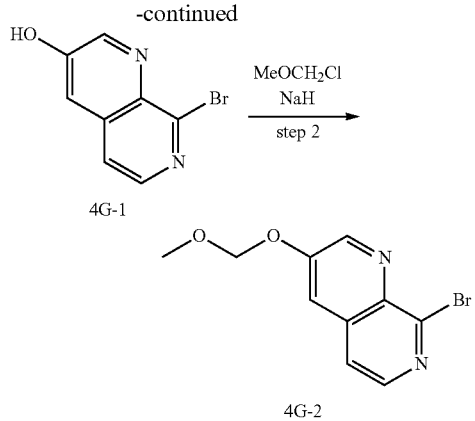

Step 1

To a suspension of 3G-2 (300 mg, 0.831 mmol) in acetonitrile (10 mL) was added bromotrimethylsilane (1270 mg, 8.31 mmol). The reaction was stirred at 80° C. for 16 h, then concentrated in vacuo to provide 4G-1. MS for 4G-1: m/e=225 and 227 (M+1).

Step 2

To a stirred solution of intermediate 4G-1 (140 mg, 0.622 mmol) in DCM (5 mL) was added 2.0 M sodium hydroxide solution (1.24 mL, 2.48 mmol) and tetrabutylammonium bromide (60.2 mg, 0.187 mmol) and the mixture stirred 20 min. at RT. The mixture was cooled to 0° C. and chloro(methoxy)methane (50.1 mg, 0.622 mmol) in DCM (1 mL) was added dropwise.

The mixture was allowed to warm to RT and stirred 3 h, after which it was diluted with water and extracted with DCM three times. The combined organic layers were dried with magnesium sulfate, filtered, and concentrated. The residue was purified by silica column chromatography (PE: EtOAc=1:1) to give compound 4G-2. ¹H NMR for 4G-2 (400 MHz CDCl3): δ ppm 8.86 (s, 1H), 8.29 (d, J=5.6 Hz, 1H), 7.64 (d, J=2.4 Hz, 1H), 7.55 (d, J=5.6 Hz, 1H), 5.37 (s, 2H), 3.54 (s, 3H).

Method H

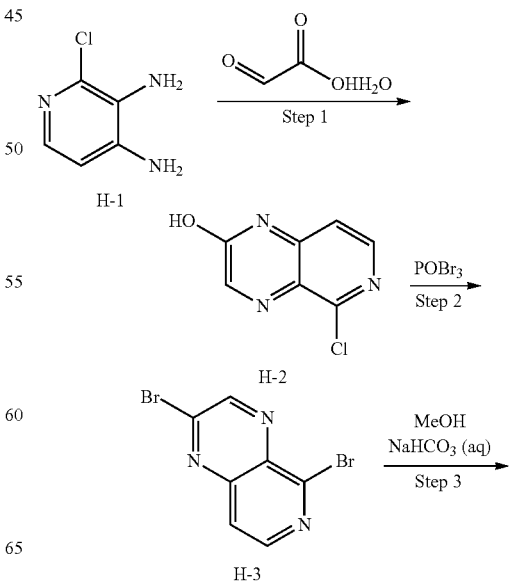

-continued

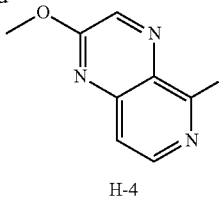

H-4

Step 1
To a solution of 2-chloropyridine-3,4-diamine H-1 (5.00 g, 34.8 mmol) in EtOH (174 mL) was added 2-oxoacetic acid hydrate (16.1 g, 174 mmol). The mixture was stirred at 75° C. for 16 h. After cooling to RT, the solvent was removed and the residue was diluted with water (5 mL) and 3:1 CHCl$_3$:IPA: (20 mL). The resulting solid was collected by filtration to afford compound H-2. MS for H-2: m/e=182 (M+1).

Step 2
A mixture of Intermediate H-2 (1.10 g, 6.06 mmol), POBr$_3$ (17.4 g, 60.6 mmol) and MeCN (30 mL) was stirred at 80° C. overnight. The mixture was poured into water (40 mL) under ice-bath and NaHCO$_3$ was used to adjust to pH 7-8. The mixture was extracted with EtOAc three times, and the combined organic layers were dried over Na$_2$SO$_4$, filtered and concentrated. The residue was purified by silica column chromatography (PE:EtOAc=5:1) to afford compound H-3. $^1$H NMR for H-3 (400 MHz CDCl3): δ ppm 8.94 (s, 1H), 8.56 (d, J=5.6 Hz, 1H), 7.78 (d, J=56 Hz, 1H).

Step 3
To a solution of Intermediate H-3 (180 mg, 0.623 mmol) in MeOH (7 mL) was added saturated NaHCO$_3$ (7 mL) and the mixture was stirred at 40° C. for 2 h. The mixture was cooled and concentrated. The residue was diluted with water, extracted with EtOAc; the combined organic extracts were dried over Na$_2$SO$_4$ and concentrated to afford compound H-4. MS for H-4: m/e=240 and 242 (M+1).

Method I

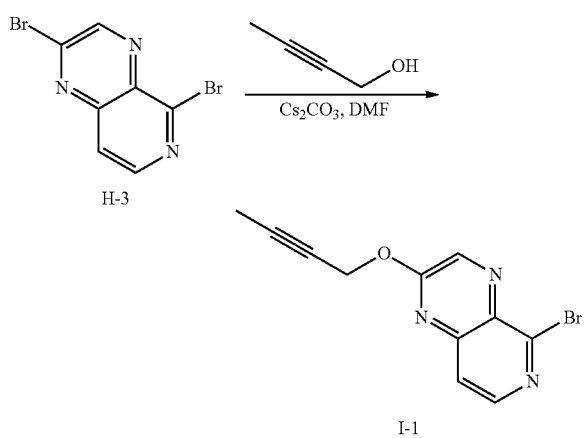

To a mixture of 2,5-dibromopyrido[3,4-b]pyrazine H-3 (50.0 mg, 0.17 mmol) and Cs$_2$CO$_3$ (67.7 mg, 0.21 mmol) in DMF (3 ml) was added but-2-yn-1-ol (12.1 mg, 0.17 mmol) at 0° C. The mixture was stirred at 25° C. for 2 h, then extracted with EtOAc (30 mL×3). The combined organic extracts were washed with water and brine, dried over Na$_2$SO$_4$, concentrated to afford compound I-1. MS for I-1: m/e=278 and 280 (M+1).

Method J

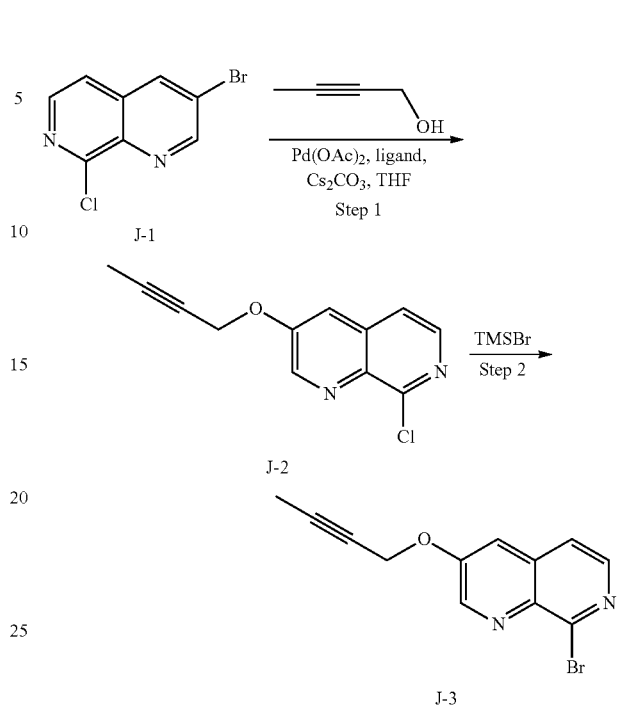

Step 1
To a mixture of 3-bromo-8-chloro-1,7-naphthyridine J-1 (4.00 g, 16.4 mmol), but-2-yn-1-ol (1.78 g, 24.6 mmol), Cs$_2$CO$_3$ (8.03 g, 24.6 mmol), and 5-(di-tert-butylphosphino)-1',3',5'-triphenyl-1'H-1,4'-bipyrazole (1.67 g, 3.29 mmol) in THF (40 mL) was added diacetoxypalladium (0.574 g, 1.64 mmol) under N$_2$. The mixture was stirred at 70° C. for 4 h and concentrated; the residue was purified directly by silica column chromatography (PE:EtOAc=3:1) to afford compound J-2. MS for J-2: m/e=233 (M+1).

Step 2
To a suspension of Intermediate J-2 (200 mg, 0.86 mmol) in acetonitrile (4 mL) was added bromotrimethylsilane (1.32 g, 8.60 mmol). The mixture was stirred at 80° C. for 16 h, then cooled to RT. The resulting solid was collected by filtration to afford compound J-3. MS for J-3: m/e=277 and 279 (M+1).

Method K

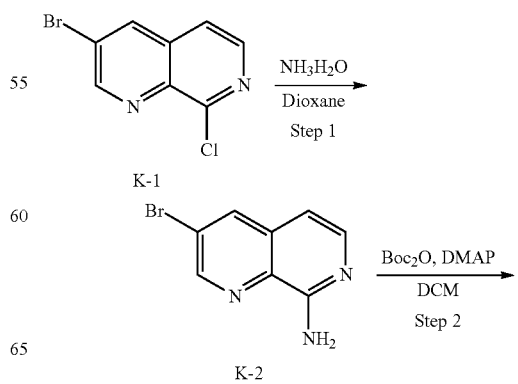

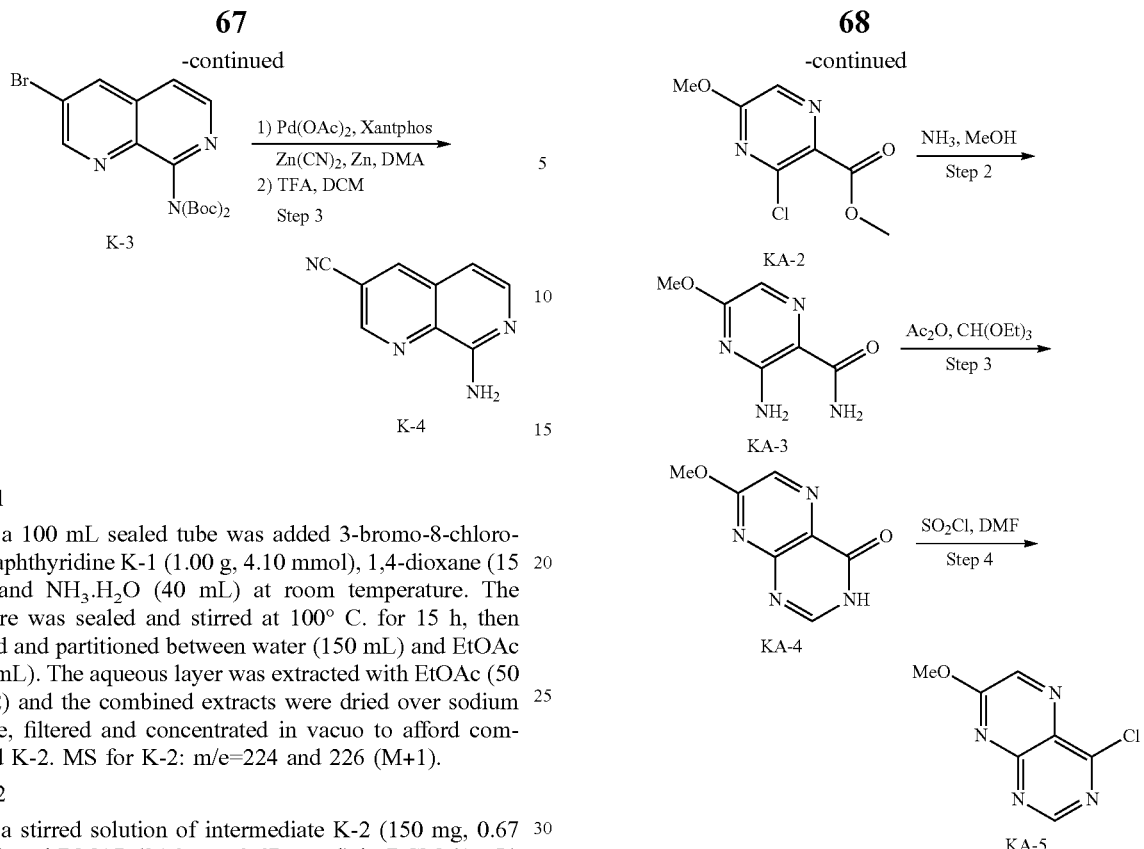

Step 1

To a 100 mL sealed tube was added 3-bromo-8-chloro-1,7-naphthyridine K-1 (1.00 g, 4.10 mmol), 1,4-dioxane (15 mL) and NH$_3$.H$_2$O (40 mL) at room temperature. The mixture was sealed and stirred at 100° C. for 15 h, then cooled and partitioned between water (150 mL) and EtOAc (100 mL). The aqueous layer was extracted with EtOAc (50 mL×2) and the combined extracts were dried over sodium sulfate, filtered and concentrated in vacuo to afford compound K-2. MS for K-2: m/e=224 and 226 (M+1).

Step 2

To a stirred solution of intermediate K-2 (150 mg, 0.67 mmol) and DMAP (84.0 mg, 0.67 mmol) in DCM (4 mL) was added di-tert-butyl dicarbonate (161 mg, 0.74 mmol). The mixture was stirred at 25° C. overnight, then quenched with water and extracted with DCM. The combined organic extracts were dried over Na$_2$SO$_4$ and concentrated. The residue was purified by p-TLC (PE:EA=1:1) to afford compound K-3. MS for K-3: m/e=424 and 426 (M+1).

Step 3

To a mixture of intermediate K-3 (356 mg, 1.10 mmol), zinc cyanide (77.0 mg, 0.66 mmol) and zinc powder (0.700 mg, 0.011 mmol) in DMF (5 mL) under nitrogen was added palladium acetate (24.7 mg, 0.11 mmol), followed by Xantphos (64.0 mg, 0.11 mmol). The mixture was degassed with nitrogen and heated at 80° C. for 3 h, then cooled and partitioned between water and EtOAc. The aqueous layer was extracted with EtOAc (100 mL×3) and the combined organic extracts were dried over sodium sulfate, filtered and concentrated in vacuo. The residue was dissolved in 3 mL of DCM, treated dropwise with TFA (0.5 mL) at 0° C. and stirred at 25° C. overnight. The resulting mixture was neutralized with NaHCO$_3$ and extracted with DCM. The organic layer was washed with brine, dried over Na$_2$SO$_4$ and concentrated; purified by silica gel (PE:EtOAc=20:1 to 1:1) to afford compound K-4. MS for K-4: 171 (M+1).

Method 2K

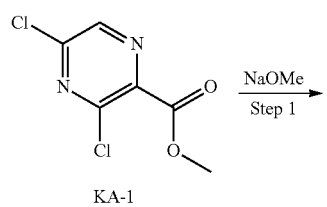

Step 1

A mixture of methyl 3,5-dichloropyrazine-2-carboxylate (1.30 g, 6.28 mmol) and sodium methoxide (0.5 M in MeOH, 13.8 mL) was stirred at room temperature for 2 h. The mixture was quenched with ice water and extracted with EtOAc (2×). The combined extracts were dried over sodium sulfate, filtered and concentrated. SiO$_2$ column chromatography (5% to 100% EtOAc in hexane) in vacuo to afford compound 2K-2. MS for 2K-2: m/e=203 (M+1).

Step 2

A stirred solution of intermediate 2K-2 (500 mg, 0.426 mmol) and ammonia (0.5 M in MeOH, 11.6 mL) was heated to 60° C. for 12 h. The mixture was cooled to rt and the resulting precipitate collected by vacuum filtration and washed with water to afford compound 2K-3. MS for 2K-3: m/e=169 (M+1).

Step 3

To a mixture of Intermediate 2K-3 (1.20 g, 7.14 mmol) and triethylorthoformate (34.9 g, 235 mmol) at rt was added acetic anhydride (43.0 g, 421 mmol). The mixture was heated at 150° C. for 3 h, then cooled and concentrated under reduced pressure to afford compound 2K-4. MS for 2K-4: 179 (M+1).

Step 4

Intermediate 2K-4 (100 mg, 0.561 mmol) was treated at rt with thionyl chloride (0.68 mL, 9.18 mmol) followed by DMF (0.043 mL, 0.561 mmol). The mixture was heated at 78° C. for 1 h, then cooled and concentrated under reduced pressure. Silica gel column chromatography (0->100% EtOAc in hexanes) provided compound 2K-5. MS for 2K-5: 197 (M+1).

Method 3K

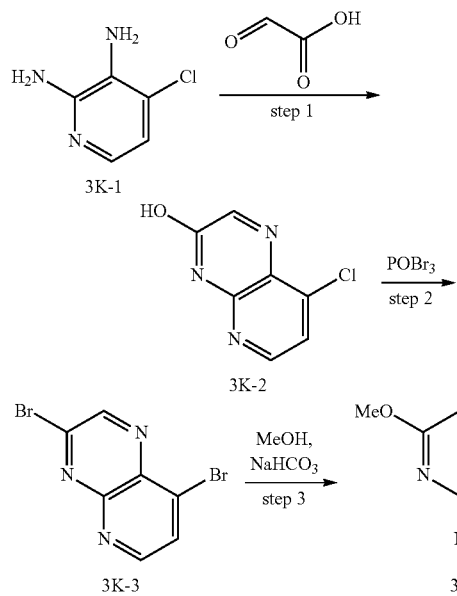

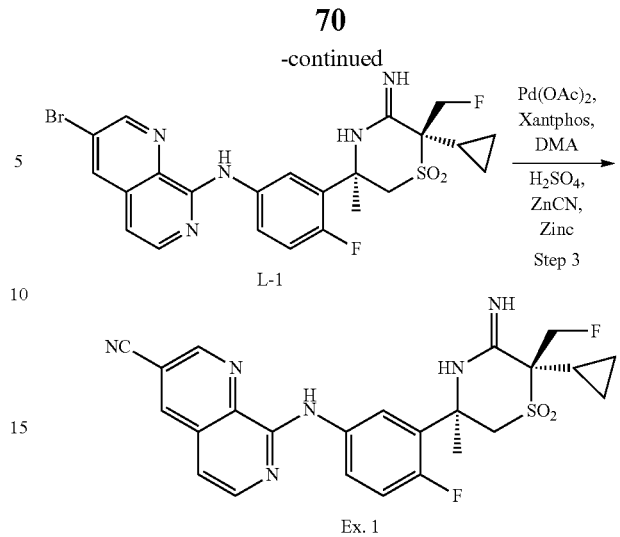

Step 1

To a solution of 4-chloropyridine-2,3-diamine 3K-1 (5.00 g, 34.8 mmol) in EtOH (80 mL) was added 2-oxoacetic acid hydrate (16.0 g, 174 mmol). The mixture was stirred at 95° C. for 16 h. After cooling to RT, the resulting solid was collected by filtration, washed with EtOH (3×), and dried to afford compound 3K-2. MS for 3K-2: m/e=182 (M+1).

Step 2

A mixture of Intermediate 3K-2 (2.25 g, 12.4 mmol), POBr$_3$ (35.5 g, 124 mmol) and MeCN (40 mL) was stirred at 110° C. for 15 h. The mixture was poured into water (40 mL) under ice-bath and NaHCO$_3$ was used to adjust to pH 7-8. The mixture was extracted with EtOAc three times, and the combined organic layers were washed with brine, dried over Na$_2$SO$_4$, filtered and concentrated to afford compound 3K-3. MS for 3K-3: m/e=289 and 331 (M+1).

Step 3

To a solution of Intermediate 3K-3 (650 mg, 2.25 mmol) in Acetonitrile (6 mL) and MeOH (18 mL) was added NaHCO$_3$ (378 mg, 4.50 mmol) and the mixture was stirred at RT for 3 h. The mixture was concentrated. The residue was diluted with water, extracted with EtOAc; the combined organic extracts were dried over Na$_2$SO$_4$ and concentrated to afford compound 3K-4. MS for 3K-4: m/e=240 and 242 (M+1).

Method L

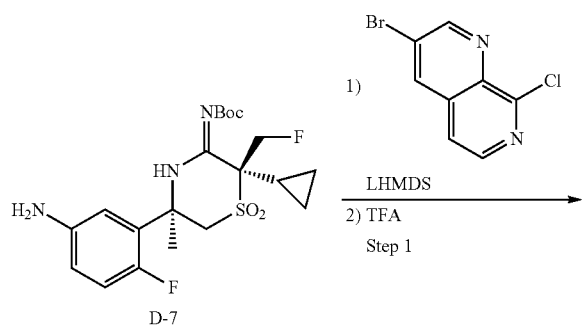

Step 1

To a stirred solution of intermediate D-7 (200 mg, 0.45 mmol) and 3-bromo-8-chloro-1,7-naphthyridine (165 mg, 0.68 mmol) in THF (8 mL) was added LHMDS (1 M in THF, 1.13 mL, 1.13 mmol) at RT. The mixture was stirred at 45° C. for 2 h, then an additional 1 eq. of LHMDS was added and the mixture was stirred at 45° C. overnight. The mixture was diluted with saturated NH$_4$Cl and extracted with DCM. The combined organic extracts were dried over Na$_2$SO$_4$ and concentrated. The resulting residue was rediluted with 5 mL of DCM and TFA (0.5 mL) was added. The resulting mixture was stirred at 25° C. for 2 h, then neutralized with NaHCO$_3$, and extracted with DCM. The organic layer was washed with brine, dried over Na$_2$SO$_4$ and concentrated. The residue was purified by prep-TLC (DCM:MeOH=15:1) to afford compound L-1. MS for L-1: m/e=550 and 552 (M+1).

Step 2

To a solution of palladium acetate (5.00 mg, 0.014 mmol) and Xantphos (8.00 mg, 0.014 mmol) in DMA (1 mL) was added H$_2$SO$_4$ (2.00 mg, 0.020 mmol). The reaction was sealed, purged with N$_2$ for 5 min and then allowed to heat at 80° C. for 30 min. after which the mixture was cooled to RT. Intermediate L-1 (70.0 mg, 0.130 mmol), Zn(CN)$_2$ (9.00 mg, 0.086 mmol), zinc (1.00 mg, 0.015 mmol) and DMA (2 mL) were added to a separate vial and purged with N$_2$ for 5 min. To this vial was introduced the catalyst solution via syringe. After the mixture was heated to 80° C. for 15 h, the mixture was quenched with sat. sodium bicarbonate and extracted with DCM. The combined organic layers were dried over Na$_2$SO$_4$ concentrated and purified by p-HPLC (ACN/water with 0.1% TFA modifier) to afford example 1 as the TFA salt. MS for example 1: m/e=497 (M+1).

Method M

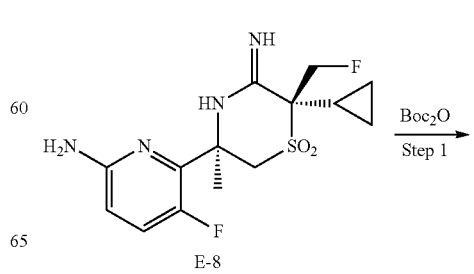

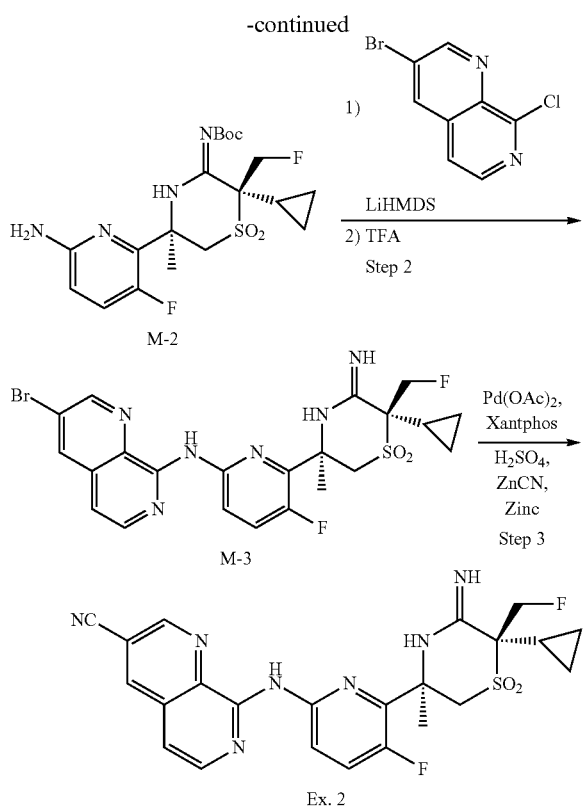

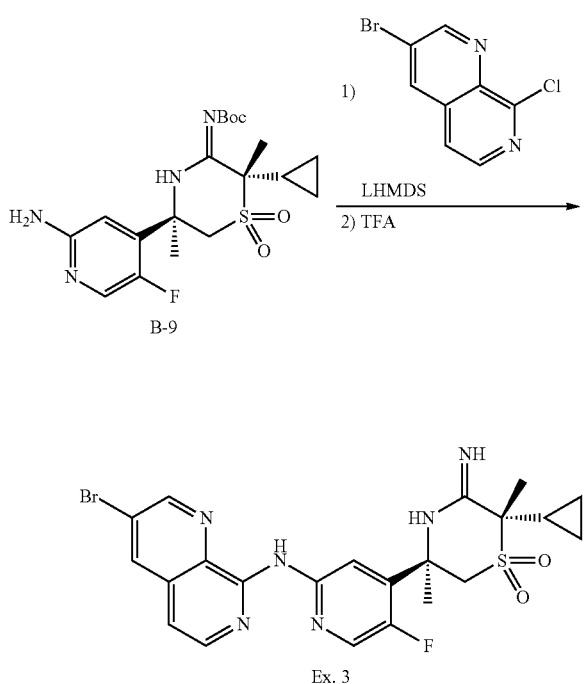

introduced the catalyst solution via syringe and the mixture was heated to 80° C. for 15 h. The mixture was quenched with saturated sodium bicarbonate, extracted with DCM (50 mL×3) and the combined organic layers dried over Na$_2$SO$_4$ and concentrated. The residue was purified by p-HPLC (ACN/water with 0.1% TFA modifier) to afford example 2 as the TFA salt. MS for example 2: m/e=498 (M+1).

Method N

Step 1

To a stirred solution of intermediate E-8 (300 mg, 0.87 mmol) and triethylamine (88.0 mg, 0.87 mmol) in DCM (8 mL) was added di-tert-butyl dicarbonate (200 mg, 0.92 mmol) and the mixture was stirred at 25° C. overnight. The resulting mixture was diluted with water and extracted with DCM. The combined organic extracts were dried over Na$_2$SO$_4$ and concentrated. The residue was purified by silica column chromatography (PE:EtOAc=3:1) to afford compound M-2. MS for M-2: m/e=445 (M+1).

Step 2

To a stirred solution of intermediate M-2 (90.0 mg, 0.20 mmol) and 3-bromo-8-chloro-1,7-naphthyridine (74.0 mg, 0.30 mmol) in THF (3 mL) was added LHMDS (1 M in THF, 0.510 mL, 0.51 mmol) at RT and the mixture was heated at 45° C. After 2 h, additional 1 eq. of LHMDS was added and the mixture was stirred overnight at 45° C. The reaction was quenched with saturated NH$_4$Cl and extracted with DCM. The combined organic extracts were dried over Na$_2$SO$_4$ and concentrated. The resulting residue was treated with 5 mL of DCM and TFA (0.5 mL) was added. The mixture was stirred at 25° C. for 2 h, then neutralized with saturated NaHCO$_3$ and extracted with DCM. The organic layer was washed with brine, dried over Na$_2$SO$_4$ and concentrated. The residue was purified by p-TLC (DCM:MeOH=15:1) to afford compound M-3. MS for M-3: m/e=551 and 553 (M+1).

Step 3

To a solution of palladium acetate (3.00 mg, 0.010 mmol) and Xantphos (6.00 mg, 0.010 mmol) in DMA (1 mL) was added H$_2$SO$_4$ (1.00 mg, 0.010 mmol). The reaction was sealed and purged with N$_2$ for 5 min., then the mixture was heated at 80° C. for 30 min. Separately, Intermediate M-3 (48.0 mg, 0.090 mmol), ZnCN$_2$ (6.00 mg, 0.057 mmol), zinc (1.00 mg, 0.015 mmol) and DMA (2 mL) were added to a vial and purged with N$_2$ for 5 min. To this solution was To a stirred solution of Intermediate B-9 (400 mg, 0.937 mmol) and 3-bromo-8-chloro-1,7-naphthyridine (252 mg, 1.03 mmol) in THF (10 mL) was added LHMDS (1 M in THF, 3.28 mL, 3.28 mmol) at RT. The mixture was stirred at 45° C. overnight, quenched with NH$_4$Cl (sat.) and extracted with DCM. The combined organic extracts were dried over Na$_2$SO$_4$ and concentrated. The residue was treated with 5 mL of DCM and 0.5 mL of TFA and stirred at 25° C. for 2 h. The mixture was neutralized with NaHCO$_3$ and extracted with DCM. The organic layer was washed with brine, dried over Na$_2$SO$_4$ and concentrated. The residue was purified by silica column chromatography (PE: EtOAc=1:1) to afford example 3. MS for example 3: m/e=533 and 535 (M+1).

Method O

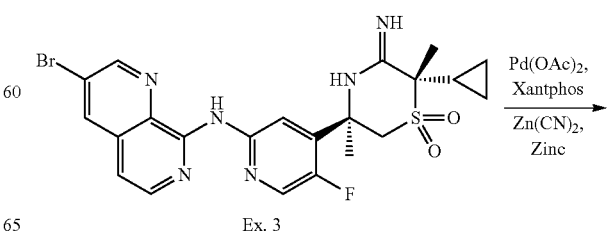

-continued

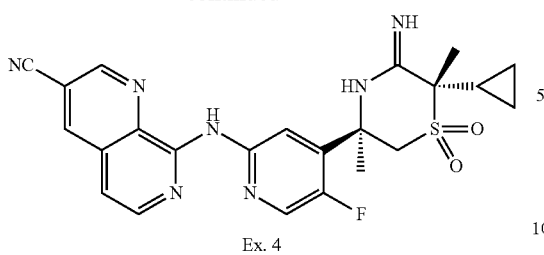

Ex. 4

A solution of Pd(OAc)$_2$ (7.20 mg, 0.032 mmol) and Xantphos (19.0 mg, 0.032 mmol) in DMA (2 mL) was sealed in a microwave tube and purged with N$_2$ for 5 min. The mixture was heated at 80° C. for 30 min. Example 3 (200 mg, 0.316 mmol), Zn(CN)$_2$ (37 mg, 0.316 mmol) and zinc (2 mg, 0.032 mmol) and DMA (2 mL) were added to a separate vial and the catalyst solution added via syringe. The mixture was heated at 80° C. for 15 h, quenched with sat Na$_2$CO$_3$ and extracted with DCM. The combined organic layers were dried over Na$_2$SO$_4$ concentrated and purified by prep-HPLC (ACN/water with 0.1% TFA modifier) to afford example 4 as a TFA salt. MS for example 4: m/e=480 (M+1).

Method P

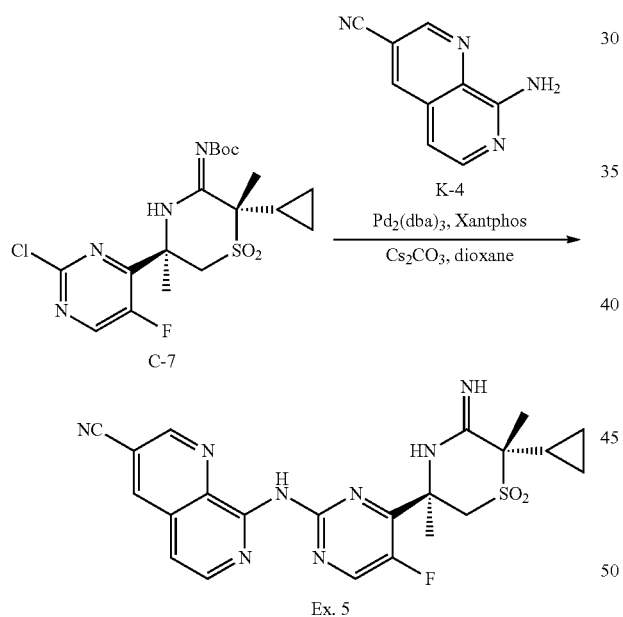

Ex. 5

To a mixture of Intermediate C-7 (120 mg, 0.27 mmol), 8-amino-1,7-naphthyridine-3-carbonitrile (46.0 mg, 0.27 mmol) and cesium carbonate (176 mg, 0.54 mmol) in dioxane (3 mL) under nitrogen were added Pd$_2$(dba)$_3$ (25.0 mg, 0.027 mmol), followed by Xantphos (15.6 mg, 0.027 mmol). The mixture was degassed with nitrogen and heated at 110° C. for 2 h, then partitioned between water and EtOAc. The aqueous layer was extracted with EtOAc (30 mL×3) and the combined extracts were dried over sodium sulfate, filtered and concentrated. The residue was purified by prep-HPLC (ACN/water with 0.1% TFA modifier) to afford example 5 as the TFA salt. MS for example 5: m/e=481 (M+1).

Method Q

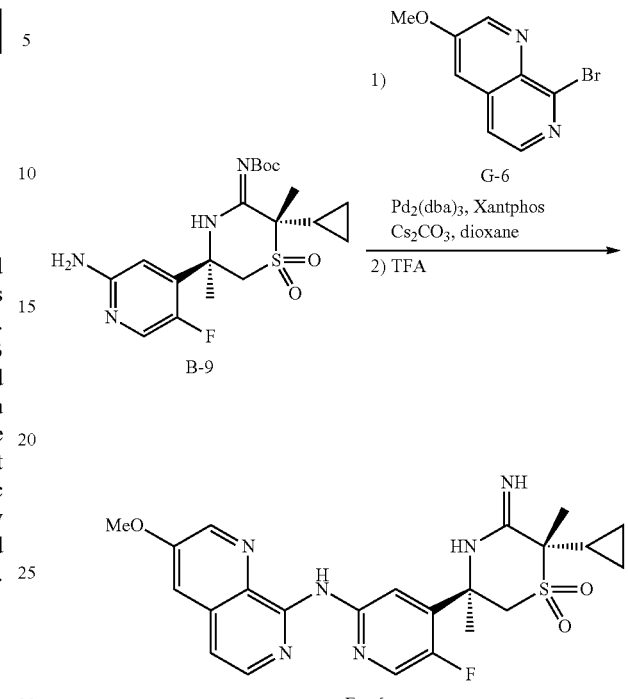

Ex. 6

To a mixture of intermediate B-9 (170 mg, 0.399 mmol), intermediate G-6 (105 mg, 0.440 mmol) and cesium carbonate (195 mg, 0.598 mmol) in DME (4 mL) were added Xantphos (46.0 mg, 0.080 mmol) and Pd$_2$(dba)$_3$ (36.0 mg, 0.0400 mmol) under N$_2$. The mixture was stirred at 65° C. for 1 h, then diluted with water (20 mL) and extracted with DCM (20 mL×3). The combined extracts were washed with brine (20 mL), dried over Na$_2$SO$_4$ and concentrated. The residue was treated with DCM (3 mL), followed by TFA (0.5 mL, 6.49 mmol). The mixture was stirred at 15° C. for 2 h, then neutralized with NaHCO$_3$ (aq.) (30 mL) and extracted with EtOAc (10 mL×3). The combined organic extracts were washed with brine (10 mL), dried over Na$_2$SO$_4$ and concentrated. The residue was purified by prep-HPLC (ACN/water with 0.1% TFA modifier) to afford example 6 as the TFA salt. MS for example 6: m/e=485 (M+1).

Method R

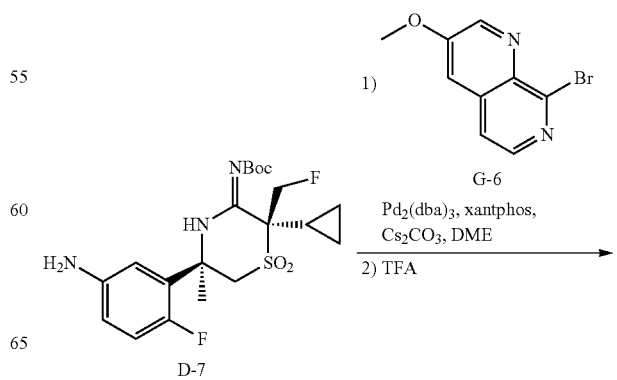

-continued

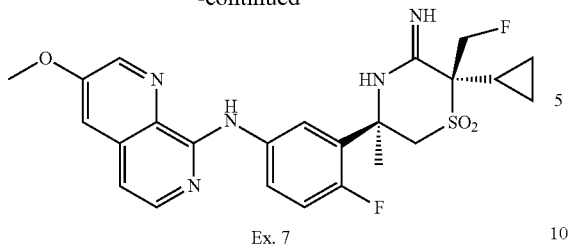

Ex. 7

To a mixture of intermediate D-7 (150 mg, 0.338 mmol), intermediate G-6 (81.0 mg, 0.338 mmol) and cesium carbonate (165 mg, 0.507 mmol) in DME (2 mL) were added Xantphos (20.0 mg, 0.034 mmol) and $Pd_2(dba)_3$ (31.0 mg, 0.034 mmol) under $N_2$. The mixture was stirred at 65° C. for 1 h, then cooled to RT, diluted with water and extracted with EtOAc (50 mL×3). The combined organic extracts were washed with brine, dried over $Na_2SO_4$ and concentrated. The residue was treated with DCM (5 mL) and TFA (1 mL), then stirred at RT overnight. The resulting mixture was diluted with water, neutralized with $NaHCO_3$ and extracted with DCM (50 mL×3). The combined organic extracts were washed with brine, dried over $Na_2SO_4$ and concentrated. The residue was purified by prep-HPLC (ACN/water with 0.1% TFA modifier) to afford example 7. MS for example 7: m/e=502 (M+1).

Method S

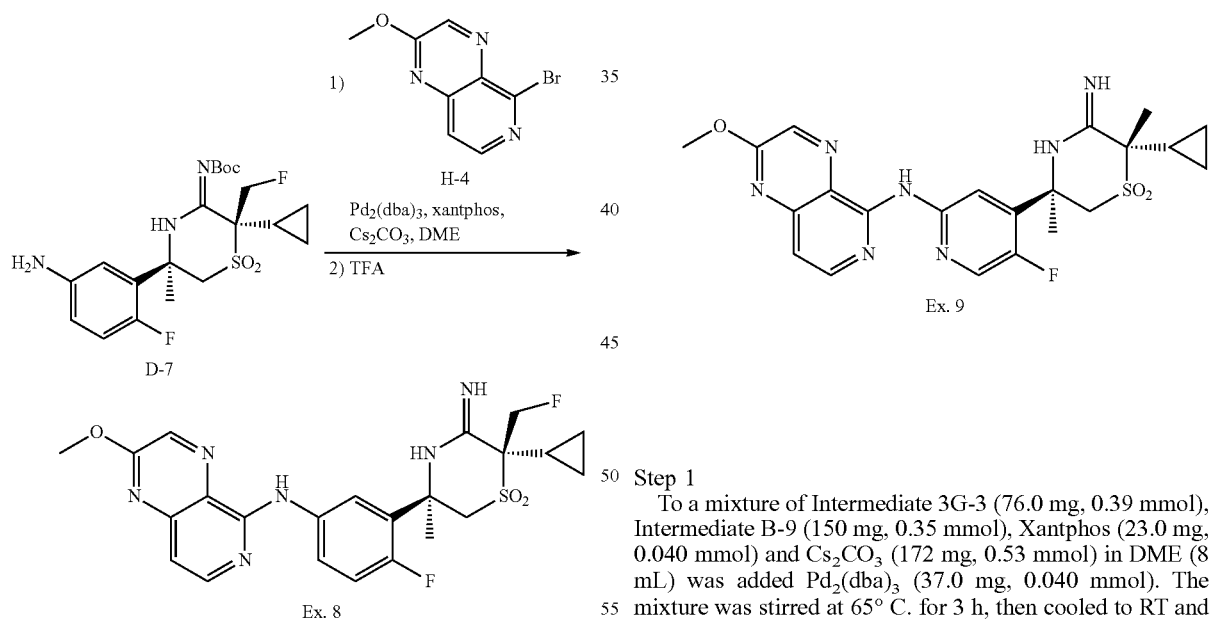

Ex. 8

To a solution of intermediate D-7 (100 mg, 0.230\ mmol) and intermediate H-4 (48.5 mg, 0.250\ mmol) in t-BuOH (4 mL) in a microwave vial was added HCl (0.12 mL of a 4 M solution in dioxane). The vial was sealed and heated to 100° C. for 1.5 h. The mixture was cooled, diluted with saturated $NaHCO_3$(aq.), and extracted with EtOAc. The combined organic extracts were dried over $Na_2SO_4$, concentrated; the residue was purified by p-HPLC (ACN/water with 0.1% TFA modifier) to afford example 8. MS for example 8: m/e=503 (M+1).

Method T

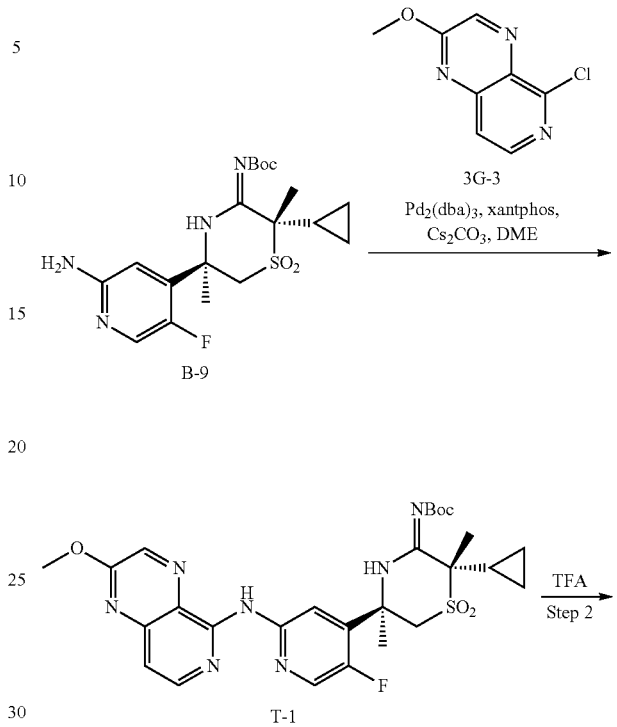

Step 1

To a mixture of Intermediate 3G-3 (76.0 mg, 0.39 mmol), Intermediate B-9 (150 mg, 0.35 mmol), Xantphos (23.0 mg, 0.040 mmol) and $Cs_2CO_3$ (172 mg, 0.53 mmol) in DME (8 mL) was added $Pd_2(dba)_3$ (37.0 mg, 0.040 mmol). The mixture was stirred at 65° C. for 3 h, then cooled to RT and diluted with EtOAc. The organic layer was washed with aq.$NH_4Cl$, dried over $Na_2SO_4$, and concentrated. The residue was purified by chromatography on silica (PE: EtOAc=10:1) to afford compound T-1. MS for T-1: m/e=586 (M+1).

Step 2

To a solution of Intermediate T-1 (43.0 mg, 0.070 mmol) in DCM (3 mL) was added TFA (0.6 mL) at 0° C. After stirring at RT for 2 h, the solution was concentrated and the residue was purified by p-HPLC (ACN/water with 0.1% TFA modifier) to afford example 9 as the TFA salt. MS for example 9: m/e=486 (M+1).

Method U

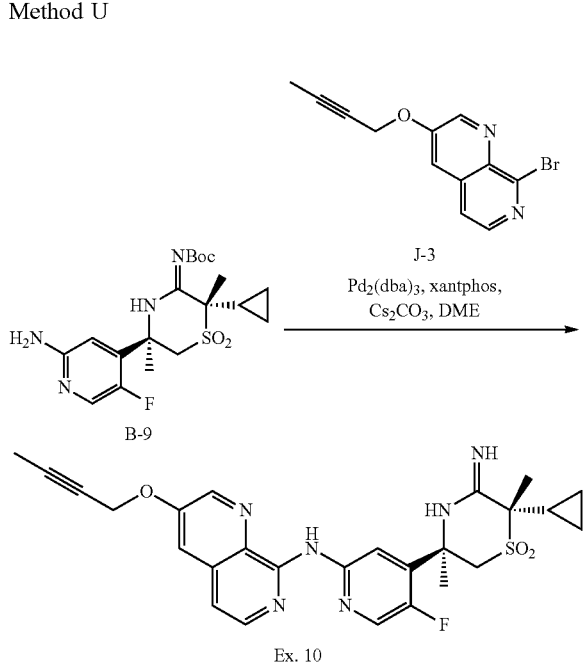

To a mixture of intermediate B-9 (60.0 mg, 0.14 mmol), intermediate J-3 (43.0 mg, 0.16 mmol) and cesium carbonate (92.0 mg, 0.280 mmol) in DME (2 mL) were added Xantphos (16.0 mg, 0.028 mmol) and Pd$_2$(dba)$_3$ (13.0 mg, 0.014 mmol) under N$_2$. The mixture was heated to 70° C. for 1 h, then diluted with water and extracted with EtOAc (10 mL×3). The combined organic extracts were dried over Na$_2$SO$_4$ and concentrated. The residue was treated with DCM (2 mL) and TFA (0.5 mL) and stirred at 15° C. for 1 h. The mixture was neutralized with NaHCO$_3$, and extracted with EtOAc. The combined extracts were dried over Na$_2$SO$_4$ and concentrated. The residue was purified by prep-HPLC (ACN/water with 0.1% TFA modifier) to afford example 10 as the TFA salt. MS for example 10: m/e=523 (M+1).

Method V

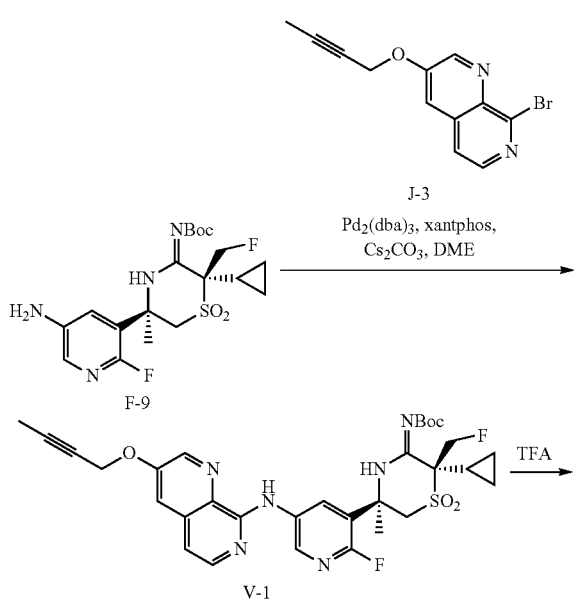

Step 1

A mixture of intermediate F-9 (64.0 mg, 0.140 mmol), intermediate J-3 (39.0 mg, 0.14 mmol), Pd$_2$(dba)$_3$ (13.0 mg, 0.014 mmol), Xantphos (8.00 mg, 0.014 mmol) and Cs$_2$CO$_3$ (70.0 mg, 0.20 mmol) in DME (3 mL) was stirred at 60° C. for 1.5 h. The mixture was quenched with H$_2$O (2 mL), extracted with EtOAc (10 mL×3); the combined organic layers were washed with brine, dried over Na$_2$SO$_4$, and concentrated to afford compound V-1. MS for V-1: m/e=641 (M+1).

Step 2

To a solution of intermediate V-1 (140 mg, 0.050 mmol) in DCM (1 mL) was added TFA (0.2 mL), the mixture was stirred at 18° C. under N$_2$ protection for 1 h, then neutralized with sat. NaHCO$_3$ (4 mL) and extracted with DCM (10 mL×3). The combined organic layers were washed with brine, concentrated, and the residue purified by prep-HPLC (ACN/water with 0.1% TFA modifier) to afford example 11 as the TFA salt. MS for example 11: m/e=541 (M+1).

Method W

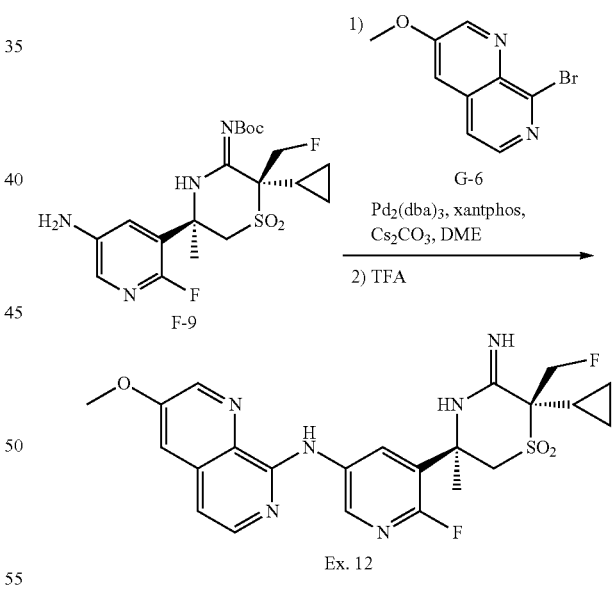

To a mixture of intermediate F-9 (124 mg, 0.280 mmol), intermediate G-6 (59.0 mg, 0.250 mmol), cesium carbonate (110 mg, 0.340 mmol) in DME (3 mL) were added Xantphos (26.0 mg, 0.0450 mmol) and Pd$_2$(dba)$_3$ (21.0 mg, 0.0220 mmol) under N$_2$. The mixture was stirred at 65° C. for 1 h, diluted with water and extracted with DCM (20 mL×3). The combined organic extracts were dried over Na$_2$SO$_4$ and concentrated. The residue was treated with DCM (3 mL) and TFA (0.5 mL) and the mixture was stirred at 15° C. for 2 h, then neutralized with NaHCO$_3$ (aq) (30 mL), and extracted with EtOAc (10 mL×3). The combined organic extracts were washed with brine, dried over $Na_2SO_4$ and concentrated. The residue was purified by prep-HPLC (ACN/water with 0.1% TFA modifier) to afford example 12 as the TFA salt. MS for example 12: m/e=503 (M+1).

Method X

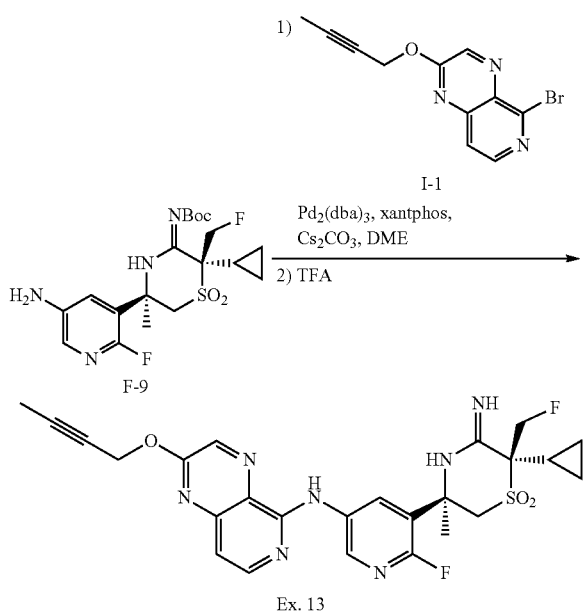

Ex. 13

To a solution of intermediate F-9 (30.4 mg, 0.0700 mmol) and intermediate I-1 (19.0 mg, 0.0700 mmol) in t-BuOH (2 mL) in a microwave vial was added HCl in dioxane (4 M, 0.06 mL). The vial was sealed and heated to 100° C. for 1.5 h, cooled to RT, diluted with $NaHCO_3$ (aq.), and extracted with EtOAc (2 mL×3). The combined organic layers were dried over $Na_2SO_4$ and concentrated. The residue was purified by p-HPLC (ACN/water with 0.1% TFA modifier) to afford example 13 as the TFA salt. MS for example 13: m/e=542 (M+1).

Method Y

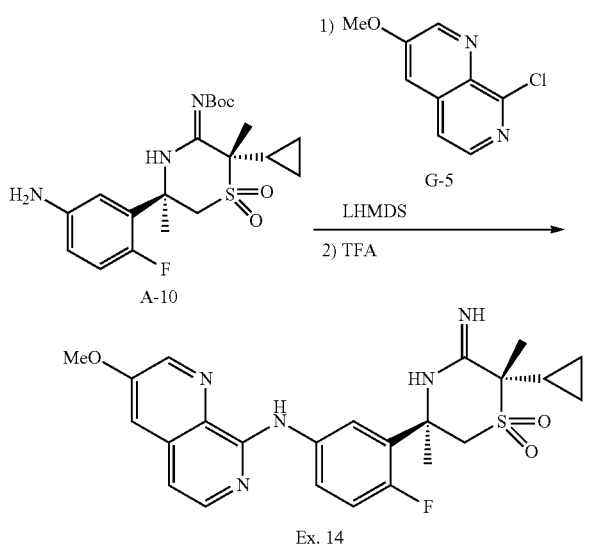

Ex. 14

To a stirred solution of intermediate A-10 (0.100 g, 0.235 mmol) and intermediate G-5 (0.0460 g, 0.235 mmol) in THF (2.4 ml) was added LHMDS in THF (0.705 ml, 0.705 mmol) at RT. The mixture was stirred at 45° C. for 14 h. The reaction mixture was cooled and diluted with dichloromethane (20 mL) and sat ammonium chloride. The organic layer was collected, dried with magnesium sulfate, filtered, and concentrated. The residue was treated with DCM (3 ml) and TFA (0.091 ml) and stirred at RT for 3 h. The mixture was then diluted with DCM (20 ml) and washed with aqueous sodium hydrogen carbonate 10 ml, dried ($Na_2SO_4$), filtered and concentrated. The residue was purified by column chromatography (40 g of $SiO_2$, 0-100% EtOAc in DCM) to give example 14. MS for example 14: m/e=484 (M+1).

Method Z

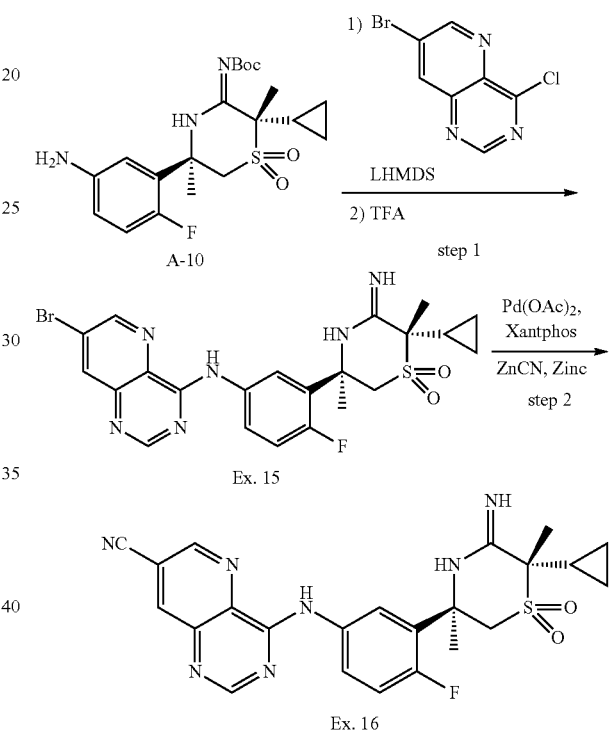

Step 1

To a stirred solution intermediate A-10 (0.410 g, 0.964 mmol) and 7-bromo-4-chloropyrido[3,2-d]pyrimidine (0.259 g, 1.06 mmol) in THF (9.6 ml) was added LHMDS in THF (2.89 ml, 2.89 mmol) at RT. The mixture was stirred at 45° C. for 14 h. The reaction mixture was cooled and diluted with dichloromethane (20 mL) and saturated ammonium chloride. The organic layer was collected, dried with magnesium sulfate, filtered, and concentrated. The residue was treated with DCM (3 ml) and TFA (0.37 ml) and stirred at RT for 15 h, after which it was diluted with DCM (20 ml) and washed with aqueous sodium hydrogen carbonate 10 mL, dried ($Na_2SO_4$), filtered and concentrated. The residue was purified by column chromatography (40 g of $SiO_2$, 0-100% EtOAc in hexane) to give example 15. MS for example 15: m/e=534 (M+1).

Step 2

To a solution of palladium(II) acetate (20.2 mg, 0.030 mmol) and 4,5-bis(diphenylphosphino)-9,9-dimethylxanthene (17.4 mg, 0.030 mmol) in DMA (2 ml) was added sulfuric acid (1.60 µl, 0.0300 mmol). The reaction was sealed and purged with N₂ for 5 min, then heated at 80° C. for 30 min., then cooled to RT. Example 15 (160 mg, 0.300 mmol), zinc cyanide (21.1 mg, 0.180 mmol), zinc (1.96 mg, 0.030 mmol) and DMA (2 mL) were added to a separate vial and purged with N₂ for 5 min after which the catalyst solution was added via syringe. The reaction mixture was heated to 80° C. for 15 h, cooled to RT, quenched with saturated NaHCO₃, and extracted with DCM (15 mL×3). The combined organic layers were dried with magnesium sulfate, filtered and concentrated. The residue was purified by column chromatography (40 g of SiO₂, 0-100% EtOAc in hexane) to give example 16. MS for example 16: m/e=480 (M+1).

Method AA

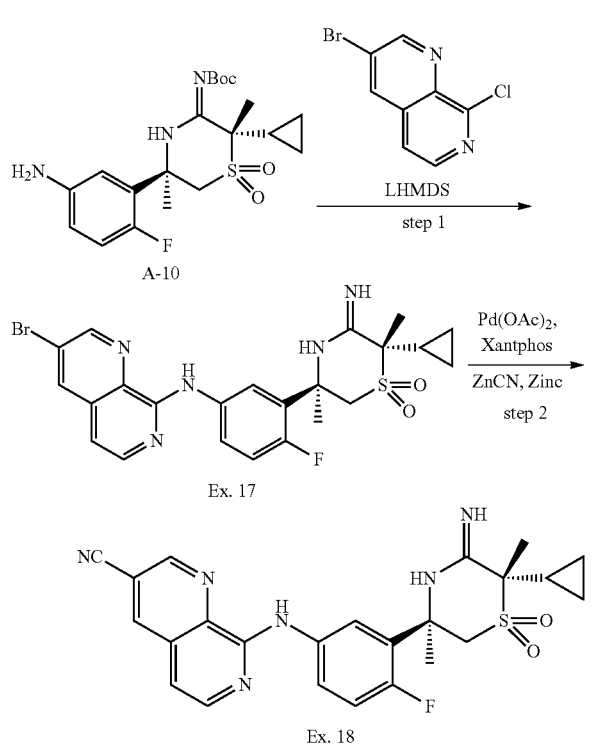

Step 1

To a stirred solution of intermediate A-10 (1.43 g, 3.36 mmol) and 3-bromo-8-chloro-1,7-naphthyridine (0.982 g, 4.03 mmol) in THF (34 ml) was added LHMDS in THF (11.8 ml, 11.8 mmol) at RT. The mixture was stirred at 45° C. for 14 h, cooled, and diluted with dichloromethane (200 mL) and water (50 ml). The organic layers were collected, dried with magnesium sulfate, filtered, and concentrated. The residue was purified by column chromatography (120 g of SiO₂, 0-100% EtOAc in hexane) to provide example 17. MS for example 17: m/e=532 and 534 (M+1).

Step 2

To a solution of palladium(II) acetate (63.3 mg, 0.0940 mmol) and Xantphos (54.3 mg, 0.0940 mmol) in DMA (3 ml) was added sulfuric acid (5.01 μl, 0.0940 mmol). The reaction was sealed and purged with N₂ for 5 min., then heated at 80° C. for 30 min. and cooled to RT. Example 17 (500 mg, 0.939 mmol), zinc cyanide (66.2 mg, 0.563 mmol) zinc (6.14 mg, 0.0940 mmol) and DMA (1 mL) were added to a separate vial and purged with N₂ for 5 min., after which the catalyst solution was added via syringe. The reaction mixture was heated to 80° C. for 15 h, cooled to RT, quenched with saturated NaHCO₃, and extracted with DCM (15 mL×3). The combined organic layers were dried with magnesium sulfate, filtered and concentrated. The residue was purified by column chromatography (80 g of SiO₂, 0-100% EtOAc in hexane) to give example 18. MS for example 18: m/e=479 (M+1).

Method AB

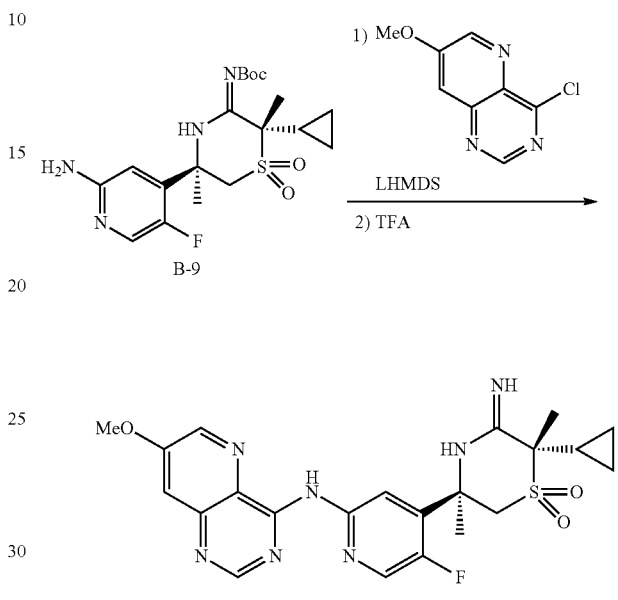

To a stirred solution of Intermediate B-9 (90.0 mg, 0.211 mmol) and 4-chloro-7-methoxypyrido[3,2-d]pyrimidine (41.3 mg, 0.211 mmol) in THF (5 ml) was added LHMDS in THF (1.06 ml, 1.06 mmol) at RT. The mixture was stirred at 25° C. for 1 h, cooled, and diluted with water (5 ml) and extracted with EtOAc (10 mL×4). The organic layers were collected, dried with sodium sulfate, filtered, and concentrated. The residue was dissolved in DCM (3 mL), treated with TFA (0.400 mL) and stirred at RT for 1 h. The mixture was quenched with aqueous sodium hydrogen carbonate (10 ml) and extracted with DCM (15 mL×3). The combined organic extracts were washed with brine, dried (Na₂SO₄), filtered and concentrated. The residue was purified by prep-HPLC (column 250×21.2 mm, 4 μm; mobile phases A=0.075% TFA water, B=MeCN; gradient 10-40% B, 11 min, 25 mL/min) to provide example 19. MS for example 19: m/e=486 (M+1).

Method AC

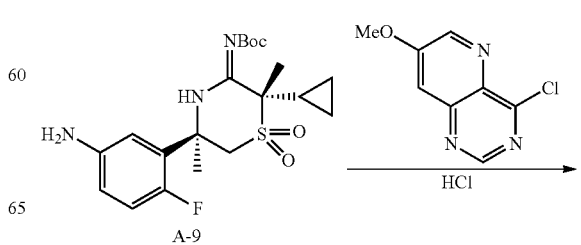

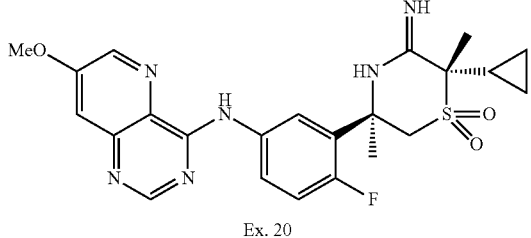

Ex. 20

A mixture of 4-chloro-7-methoxypyrido[3,2-d]pyrimidine (36.1 mg, 0.184 mmol), intermediate A-9 (60.0 mg, 0.184 mmol) and 4 M hydrogen chloride (0.046 ml, 0.184 mmol, solution in 1,4-dioxane) in t-BuOH (2 ml) was stirred at 100° C. for 1 h. The mixture was neutralized with sat. NaHCO₃ (5 mL), and extracted with EtOAc (15 mL×3). The combined organic layers were washed with brine (10 mL), dried over Na₂SO₄, filtered and concentrated. Purified by prep-HPLC (column 100×21.2 mm, 4 um; mobile phases A=0.075 TFA water, B=MeCN; gradient 16-42% B, 12 min, 25 mL/min) to afford. example 20. MS for example 20: m/e=485 (M+1).

Method AD

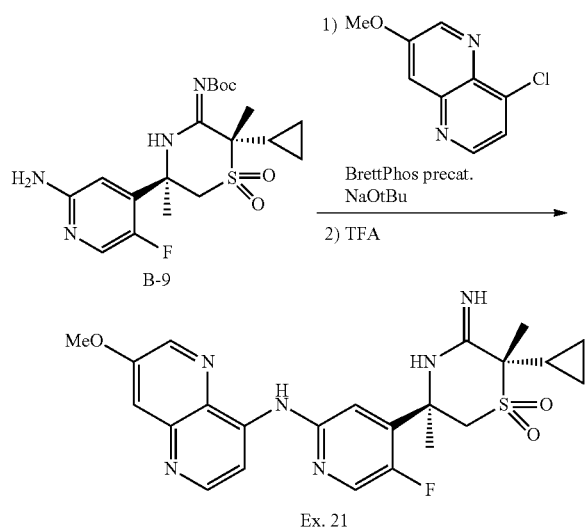

To a stirred solution of Intermediate B-9 (99.0 mg, 0.231 mmol) and 8-chloro-3-methoxy-1,5-naphthyridine (30.0 mg, 0.154 mmol) in THF (4 ml) under nitrogen was added chloro[2-(dicyclohexylphosphino)-3,6-dimethoxy-2',4',6'-triisopropyl-1,1'-biphenyl][2-(2-aminoethyl)phenyl]palladium(II) (24.6 mg, 0.0310 mmol) and sodium tert-butoxide (0.154 mL, 2 M) at RT. The mixture was stirred at 40° C. for 15 h, cooled, filtered, and diluted with water (5 ml) and extracted with EtOAc (6 mL×3). The organic layers were collected, dried with sodium sulfate, filtered, and concentrated. The residue was dissolved in DCM (6 mL), treated with TFA (0.200 mL) and stirred at 18° C. for 1 h. The mixture was quenched with aqueous sodium hydrogen carbonate (5 ml) and extracted with EtOAc (5 mL×4). The combined organic extracts were washed with brine, dried (Na₂SO₄), filtered and concentrated. The residue was purified by prep-HPLC (column 250×21.2 mm, 4 μm; mobile phases A=0.075% TFA water, B=MeCN; gradient 10-40% B, 11 min, 25 mL/min) to provide example 21. MS for example 21: m/e=485 (M+1).

Method AE

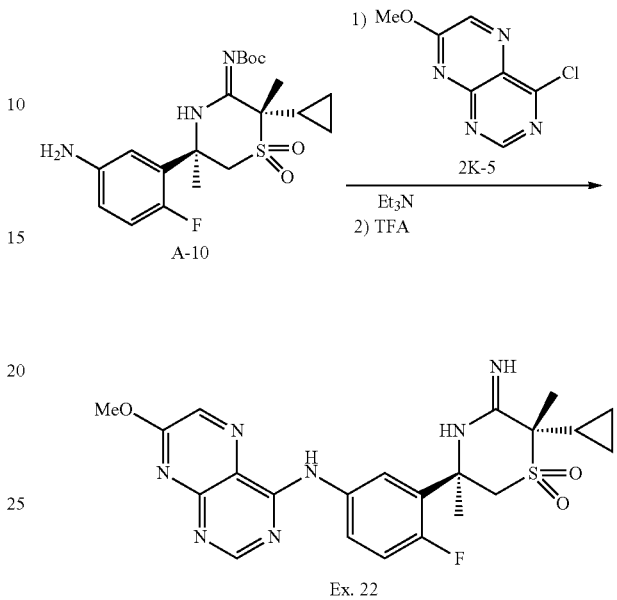

Ex. 22

To a stirred solution of intermediate A-10 (43.3 mg, 0.102 mmol) and intermediate 2K-5 (20.0 mg, 0.102 mmol) in t-BuOH (2 ml) under nitrogen was added triethylamine (30.9 mg, 0.305 mmol) at RT. The mixture was stirred at 75° C. for 1 h, cooled and diluted with water (5 ml) and extracted with EtOAc (6 mL×3). The organic layers were collected, dried with sodium sulfate, filtered, and concentrated. The residue was dissolved in DCM (6 mL), treated with TFA (1.5 mL) and stirred at 18° C. for 1 h. The mixture was quenched with aqueous sodium hydrogen carbonate (5 ml) and extracted with EtOAc (5 mL×4). The combined organic extracts were washed with brine, dried (Na₂SO₄), filtered and concentrated. The residue was purified by prep-HPLC (column 250×21.2 mm, 4 μm; mobile phases A=0.075% TFA water, B=MeCN; gradient 10-40% B, 11 min, 25 mL/min) to provide example 22. MS for example 22: m/e=486 (M+1).

Method AF

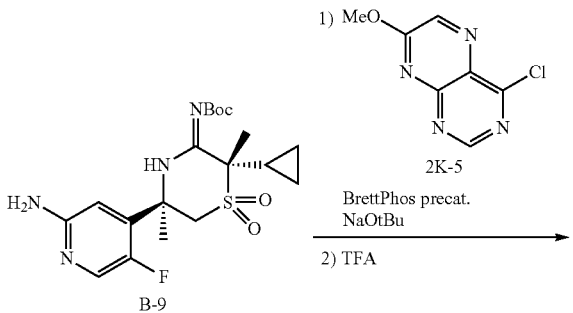

-continued

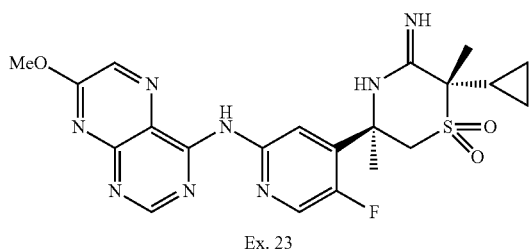

Ex. 23

To a stirred solution of Intermediate B-9 (87.0 mg, 0.203 mmol) and intermediate 2K-5 (40.0 mg, 0.203 mmol) in THF (4 ml) under nitrogen at 0° C. was added LHMDS (1.0 M, 0.814 mL) and the mixture stirred 1 h. The mixture was quenched with water (5 ml) and extracted with EtOAc (10 mL×3). The organic layers were collected, dried with sodium sulfate, filtered, and concentrated. The residue was dissolved in DCM (6 mL), treated with TFA (0.300 mL) and stirred at 18° C. for 1 h. The mixture was quenched with aqueous sodium hydrogen carbonate (5 ml) and extracted with EtOAc (5 mL×4). The combined organic extracts were washed with brine, dried (Na$_2$SO$_4$), filtered and concentrated. The residue was purified by prep-HPLC (column 250×21.2 mm, 4 μm; mobile phases A=0.075 TFA water, B=MeCN; gradient 10-40% B, 11 min, 25 mL/min) to provide example 23. MS for example 23: m/e=487 (M+1).

Method AG

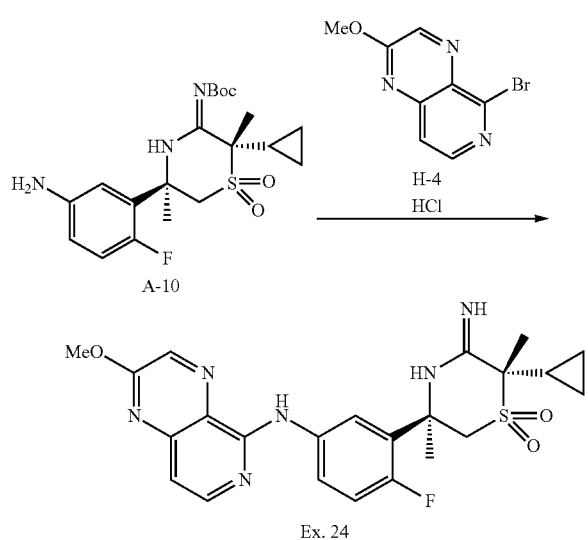

Ex. 24

To a solution of intermediate A-10 (45.0 mg, 0.106 mmol) and intermediate H-4 (26.7 mg, 0.111 mmol) in tBuOH (3 ml) under nitrogen was added HCl in dioxane (4 M, 0.053 mL). The mixture was sealed and heated in a MW reactor at 100° C. for 1.5 h, cooled, diluted with sat sodium bicarbonate solution (5 ml) and extracted with EtOAc (3 mL×3). The organic layers were collected, dried with sodium sulfate, filtered, and concentrated. The residue purified by prep-HPLC (column 250×21.2 mm, 4 μm; mobile phases A=0.075 TFA water, B=MeCN; gradient 10-40% B, 11 min, 25 mL/min) to provide example 24. MS for example 24: m/e=485 (M+1).

Method AH

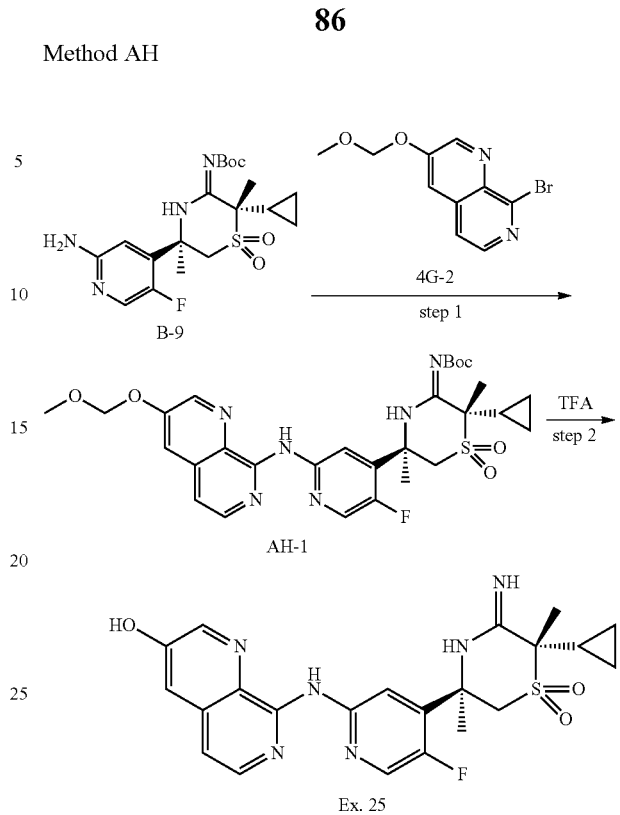

Ex. 25

Step 1

To a mixture of intermediate B-9 (96.0 mg, 0.225 mmol), intermediate 4G-2 (60.6 mg, 0.225 mmol), and cesium carbonate (147 mg, 0.450 mmol) in DME (2 mL) under nitrogen was added (9,9-dimethyl-9H-xanthene-4,5-diyl)bis(diphenylphosphine) (26.0 mg, 0.0450 mmol) and Pd$_2$(dba)$_3$ (41.2 mg, 0.0450 mmol). The mixture was stirred at 65° C. for 2 h, diluted with water and extracted with DCM (20 mL×3). The combined organic extracts were dried over Na$_2$SO$_4$ and concentrated. The residue was purified by prep-TLC (SiO$_2$; PE:EtOAc=1:2) to afford compound AH-1. MS for AH-1: m/e=616 (M+1).

Step 2

A solution of AH-1 (99.0 mg, 0.0970 mmol) in DCM (5 mL) was treated with TFA (1 mL) and the mixture stirred at RT for 2 h. The mixture was concentrated in vacuo and the resulting residue purified by prep-HPLC (column 250×21.2 mm, 4 μm; mobile phases A=0.075 TFA water, B=MeCN; gradient 10-40% B, 11 min, 25 mL/min) to provide example 25. MS for example 25: m/e=471 (M+1).

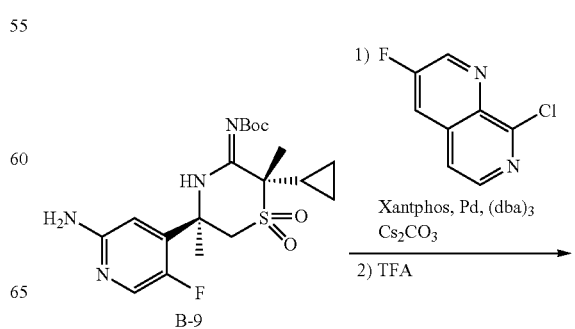

-continued

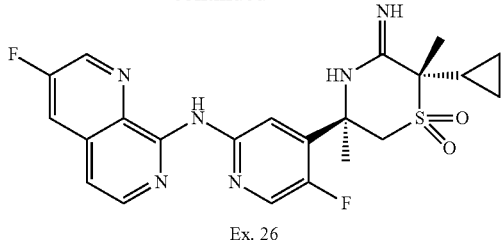

Ex. 26

Method AI

To a stirred solution of Intermediate B-9 (47.5 mg, 0.111 mmol) and 8-chloro-3-fluoro-1,7-naphthyridine (21.4 mg, 0.117 mmol) in DMF (5 ml) under nitrogen was added 4,5-bis(diphenylphosophino)-9,9-dimethylxanthene (12.9 mg, 0.0220 mmol), Pd$_2$(dba)$_3$ (10.2 mg, 0.0110 mmol) and cesium carbonate (0.109 mg, 0.334 mmol) at RT. The mixture was stirred at 65° C. for 2 h, cooled, filtered, and diluted with water (5 ml) and extracted with EtOAc (6 mL×3). The organic layers were collected, dried with sodium sulfate, filtered, and concentrated. The residue was dissolved in DCM (3 mL), treated with TFA (0.200 mL) and stirred at 18° C. for 1 h. The mixture was quenched with aqueous sodium hydrogen carbonate (5 ml) and extracted with EtOAc (5 mL×4). The combined organic extracts were washed with brine, dried (Na$_2$SO$_4$), filtered and concentrated. The residue was purified by prep-HPLC (column 250×21.2 mm, 4 μm; mobile phases A=0.075% TFA water, B=MeCN; gradient 10-40% B, 11 min, 25 mL/min) to provide example 26. MS for example 26: m/e=473 (M+1).

The following additional examples were prepared using procedures analogous to those described above in method AI:

| Ex # | Structure | SM 1 | SM 2 | me (M + H) |
|---|---|---|---|---|
| 27 | 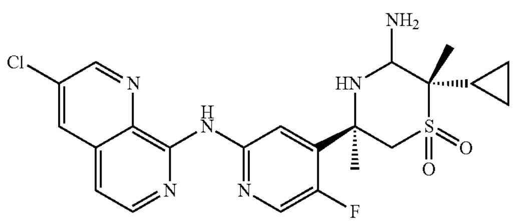 [SMILES: C[C@]1(C2CC2)C(N)N[C@](C)(c2cc(Nc3nccc4cc(Cl)cnc34)ncc2F)CS1(=O)=O] | 3,8-dichloro-1,7-naphthyridine | B-9 | 490 |
| 28 | 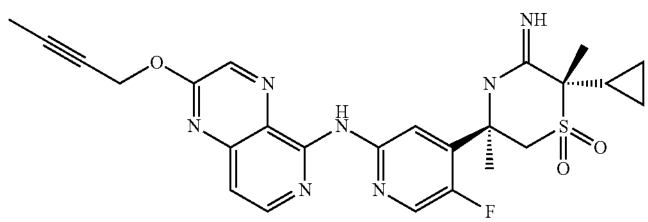 [SMILES: CC#CCOc1cnc2c(Nc3cc([C@]4(C)CS(=O)(=O)[C@@](C)(C5CC5)C(=N)N4)c(F)cn3)nccc2n1] | I-1 | B-9 | 525 |
| 29 | 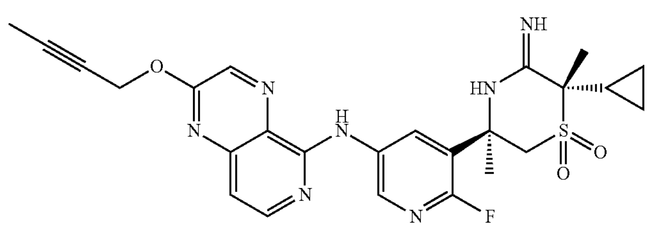 [SMILES: CC#CCOc1cnc2c(Nc3cnc(F)c([C@]4(C)CS(=O)(=O)[C@@](C)(C5CC5)C(=N)N4)c3)nccc2n1] | I-1 | 2F-5 | 525 |
| 30 | 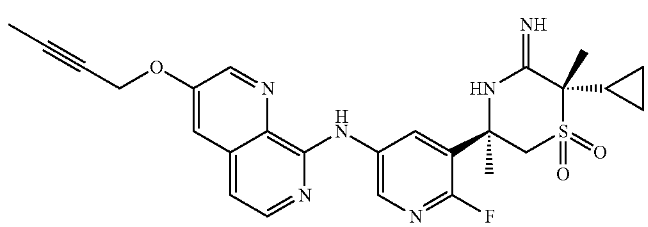 | J-3 | 2F-5 | 524 |
| 31 | 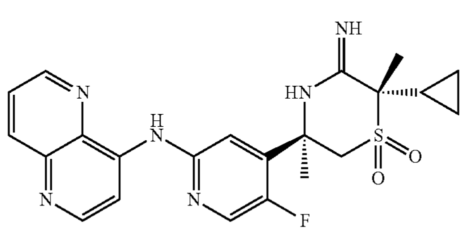 [SMILES: C[C@@]1(c2cc(Nc3ccnc4cccnc34)ncc2F)CS(=O)(=O)[C@@](C)(C2CC2)C(=N)N1] | 4-chloro-1,5-naphthyridine | B-9 | 524 |

-continued

| Ex # | Structure | SM 1 | SM 2 | me (M + H) |
|---|---|---|---|---|
| 32 | 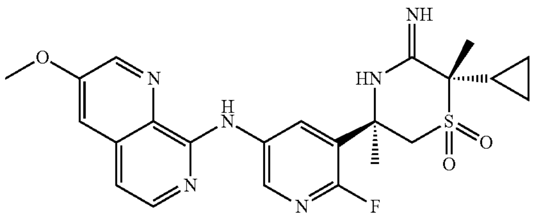 [SMILES: COc1cnc2c(Nc3cnc(F)c([C@]4(C)CS(=O)(=O)[C@@](C)(C5CC5)C(=N)N4)c3)nccc2c1] | G-6 | 2F-5 | 485 |
| 33 | 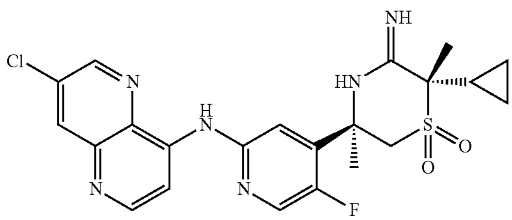 [SMILES: C[C@@]1(c2cc(Nc3ccnc4cc(Cl)cnc34)ncc2F)CS(=O)(=O)[C@@](C)(C2CC2)C(=N)N1] | 3,8-dichloro-1,5-naphthyridine | B-9 | 485 |
| 34 | 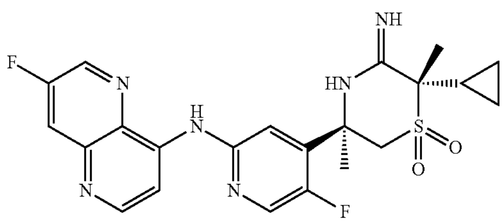 [SMILES: C[C@@]1(c2cc(Nc3ccnc4cc(F)cnc34)ncc2F)CS(=O)(=O)[C@@](C)(C2CC2)C(=N)N1] | 3-chloro-8-fluoro-1,5-naphthyridine | B-9 | 474 |
| 35 | 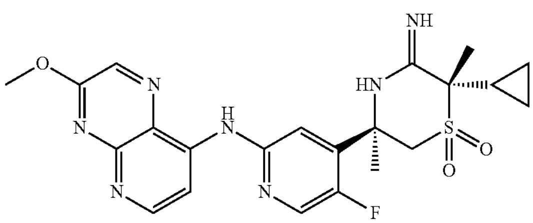 | 3K-4 | B-9 | 487 |
| 36 | 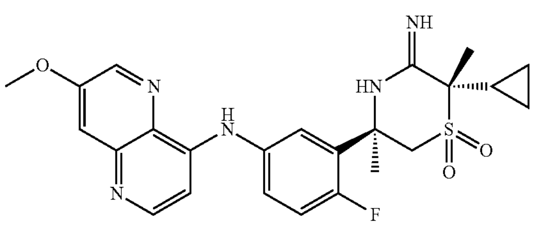 [SMILES: COc1cnc2c(Nc3ccc(F)c([C@]4(C)CS(=O)(=O)[C@@](C)(C5CC5)C(=N)N4)c3)ccnc2c1] | 8-chloro-3-methoxy-1,5-naphthyridine | A-10 | 485 |
| 37 | 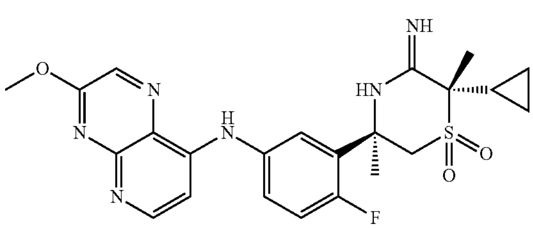 | 3K-4 | A-10 | 486 |
| 38 | 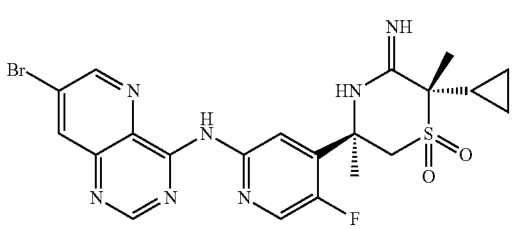 | 4,7-dibromopyrido[3,2-d]pyrimidine | B-9 | 535 |

| Ex # | Structure | SM 1 | SM 2 | me (M + H) |
|---|---|---|---|---|
| 39 | 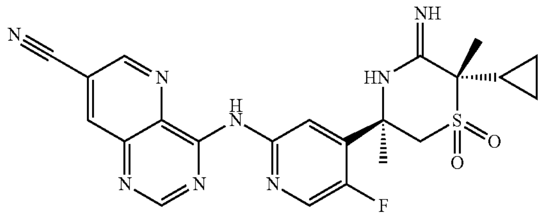 [SMILES: C[C@@]1(c2cc(Nc3ncnc4cc(C#N)cnc34)ncc2F)CS(=O)(=O)[C@@](C)(C2CC2)C(=N)N1] | Ex. 38 | — | 481 |

In another embodiment, the compounds of the invention comprise the example compounds shown in the table below, or a tautomer thereof, or a pharmaceutically acceptable salt of said compound or said tautomer. These example compounds of the invention were prepared from the methods described herein. The free base form, as well as the hydrochloride salt, the tosylate salt, the citrate salt, and the oxalate salt are each specifically contemplated as alternative embodiments of each of the compounds of the invention shown in the table below. BACE-1 and BACE-2 values reported in this table were measured using Assay 1 and Assay 2, respectively.

TABLE 1

| Ex | Structure / IUPAC Name | LCMS m/z | BACE-1 $K_i$ (nM) | BACE2 $K_i$ (nM) |
|---|---|---|---|---|
| 1 | 8-({3-[(3R,6S)-6-cyclopropyl-6-(fluoromethyl)-5-imino-3-methyl-1,1-dioxidothiomorpholin-3-yl]-4-fluorophenyl}amino)-1,7-naphthyridine-carbonitrile | 497 | 1.3 | 0.6 |
| 2 | 8-({6-[(3R,6S)-6-cyclopropyl-6-(fluoromethyl)-5-imino-3-methyl-1,1-dioxidothiomoipholin-3-yl]-5-fluoropyridin-2-yl}amino)-1,7-naphthyridine-3-carbonitrile | 498 | 15.0 | 6.9 |
| 3 | 3-bromo-N-{4-[(3R,6S)-6-cyclopropyl-5-imino-3,6-dimethyl-1,1-dioxidothiomorpholin-3-yl]-5-fluoropyridin-2-yl}-1,7-naphthyridin-8-amine | 535 | 1.5 | 0.35 |

TABLE 1-continued

| Ex | Structure / IUPAC Name | LCMS m/z | BACE-1 $K_i$ (nM) | BACE2 $K_i$ (nM) |
|---|---|---|---|---|
| 4 | 8-({4-[(3R,6S)-6-cyclopropyl-5-imino-3,6-dimethyl-1,1-dioxidothiomorpholin-3-yl]-5-fluoropyridin-2-yl}amino)-1,7-naphthyridine-3-carbonitrile | 480 | 3.8 | 1.5 |
| 5 | 8-({4-[(3R,6S)-6-cyclopropyl-5-imino-3,6-dimethyl-1,1-dioxidothiomorpholin-3-yl]-5-fluoropyrimidin-2-yl}amino)-1,7-naphthyridine-3-carbonitrile | 481 | 8.7 | 7.8 |
| 6 | N-{4-[(3R,6S)-6-cyclopropyl-5-imino-3,6-dimethyl-1,1-dioxidothiomorpholin-3-yl]-5-fluoropyridin-2-yl}-3-methoxy-1,7-naphthyridin-8-amine | 485 | 2.6 | 0.57 |
| 7 | N-{3-[(3R,6S)-6-cyclopropyl-6-(fluoromethyl)-5-imino-3-methyl-1,1-dioxidothiomorpholin-3-yl]-4-fluorophenyl}-3-methoxy-1,7-naphthyridin-8-amine | 502 | 7.1 | 3.6 |
| 8 | N-{3-[(3R,6S)-6-cyclopropyl-6-(fluoromethyl)-5-imino-3-methyl-1,1-dioxidothiomorpholin-3-yl]-4-fluorophenyl}-2-methoxypyrido[3,4-b]pyrazin-5-amine | 503 | 4.5 | 4.2 |

TABLE 1-continued

| Ex | Structure / IUPAC Name | LCMS m/z | BACE-1 $K_i$ (nM) | BACE2 $K_i$ (nM) |
|---|---|---|---|---|
| 9 | N-{4-[(3R,6S)-6-cyclopropyl-5-imino-3,6-dimethyl-1,1-dioxidothiomorpholin-3-yl]-5-fluoropyridin-2-yl}-2-methoxypyrido[3,4-b]pyrazin-5-amine | 486 | 13.6 | 1.3 |
| 10 | 3-(but-2-yn-1-yloxy)-N-{4-[(3R,6S)-6-cyclopropyl-5-imino-3,6-dimethyl-1,1-dioxidothiomorpholin-3-yl]-5-fluoropyridin-2-yl}-1,7-naphthyridin-8-amine | 523 | 0.79 | 0.64 |
| 11 | 3-(but-2-yn-1-yloxy)-N-{5-[(3R,6S)-6-cyclopropyl-6-(fluoromethyl)-5-imino-3-methyl-1,1-dioxidothiomorpholin-3-yl]-6-fluoropyridin-3-yl}-1,7-naphthyridin-8-amine | 541 | 0.91 | 7.5 |
| 12 | N-{5-[(3R,6S)-6-cyclopropyl-6-(fluoromethyl)-5-imino-3-methyl-1,1-dioxidothiomorpholin-3-yl]-6-fluoropyridin-3-yl}-3-methoxy-1,7-naphthyridin-8-amine | 503 | 6.1 | 3.3 |
| 13 | 2-(but-2-yn-1-yloxy)-N-{5-[(3R,6S)-6-cyclopropyl-6-(fluoromethyl)-5-imino-3-methyl-1,1-dioxidothiomorpholin-3-yl]-6-fluoropyridin-3-yl}pyrido[3,4-b]pyrazin-5-amine | 542 | 0.65 | 1.1 |

TABLE 1-continued

| Ex | Structure / IUPAC Name | LCMS m/z | BACE-1 $K_i$ (nM) | BACE2 $K_i$ (nM) |
|---|---|---|---|---|
| 14 | 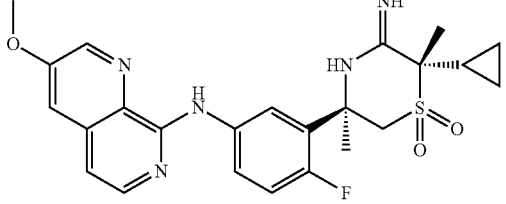<br>N-{3-[(3R,6S)-6-cyclopropyl-5-imino-3,6-dimethyl-1,1-dioxidothiomorpholin-3-yl]-4-fluorophenyl}-3-methoxy-1,7-naphthyridin-8-amine | 484 | 9.3 | 2.8 |
| 15 | 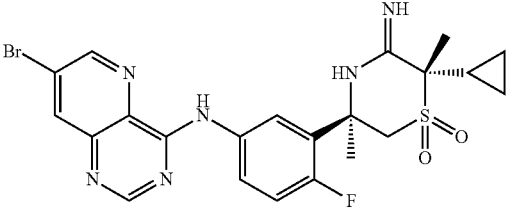<br>7-bromo-N-{3-[(3R,6S)-6-cyclopropyl-5-imino-3,6-dimethyl-1,1-dioxidothiomorpholin-3-yl]-4-fluorophenyl}pyrido[3,2-d]pyrimidin-4-amine | 533 | 1.8 | 0.73 |
| 16 | 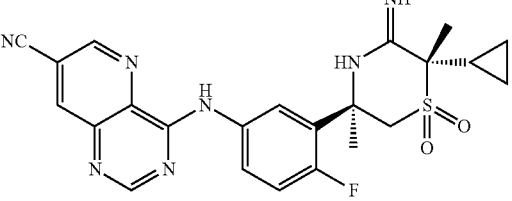<br>4-({3-[(3R,6S)-6-cyclopropyl-5-imino-3,6-dimethyl-1,1-dioxidothiomorpholin-3-yl]-4-fluorophenyl}amino)pyrido[3,2-d]pyrimidine-7-carbonitrile | 480 | 2.2 | 1.4 |
| 17 | 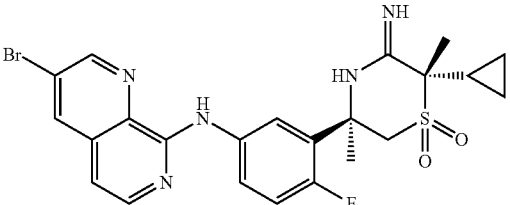<br>3-bromo-N-{3-[(3R,6S)-6-cyclopropyl-5-imino-3,6-dimethyl-1,1-dioxidothiomorpholin-3-yl]-4-fluorophenyl}-1,7-naphthyridin-8-amine | 532 | 1.4 | 0.41 |
| 18 | 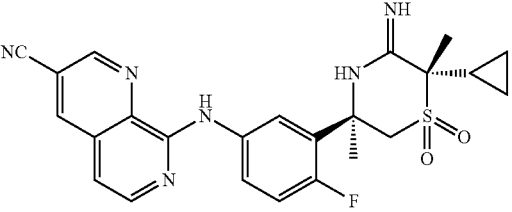 [SMILES: C[C@@]1(c2cc(Nc3nccc4cc(C#N)cnc34)ccc2F)CS(=O)(=O)[C@@](C)(C2CC2)C(=N)N1]<br>8-({3-[(3R,6S)-6-cyclopropyl-5-imino-3,6-dimethyl-1,1-dioxidothiomorpholin-3-yl]-4-fluorophenyl}amino)-1,7-naphthyridine-3-carbonitrile | 479 | 1.6 | 0.64 |

TABLE 1-continued

| Ex | Structure IUPAC Name | LCMS m/z | BACE-1 $K_i$ (nM) | BACE2 $K_i$ (nM) |
|---|---|---|---|---|
| 19 | N-{4-[(3R,6S)-6-cyclopropyl-5-imino-3,6-dimethyl-1,1-dioxidothiomorpholin-3-yl]-5-fluoropyridin-2-yl}-7-methoxypyrido[3,2-d]pyrimidin-4-amine | 486 | 67 | 21 |
| 20 | (2S,5R)-2-cyclopropyl-5-(2-fluoro-5-((7-methoxypyrido[3,2-d]pyrimidin-4-yl)amino)phenyl)-3-imino-2,5-dimethylthiomorpholine 1,1-dioxide | 485 | 3.7 | 2.4 |
| 21 | (2S,5R)-2-cyclopropyl-5-(5-fluoro-2-((7-methoxy-1,5-naphthyridin-4-yl)amino)pyridin-4-yl)-3-imino-2,5-dimethylthiomorpholine 1,1-dioxide | 485 | 5.3 | 1.9 |
| 22 | (2S,5R)-2-cyclopropyl-5-(2-fluoro-5-((7-methoxypteridin-4-yl)amino)phenyl)-3-imino-2,5-dimethylthiomorpholine 1,1-dioxide | 486 | 14 | 11 |
| 23 | (2S,5R)-2-cyclopropyl-5-(5-fluoro-2-((7-methoxypteridin-4-yl)amino)pyridin-4-yl)-3-imino-2,5-dimethylthiomorpholine 1,1-dioxide | 487 | 271 | 129 |

TABLE 1-continued

| Ex | Structure / IUPAC Name | LCMS m/z | BACE-1 $K_i$ (nM) | BACE2 $K_i$ (nM) |
|---|---|---|---|---|
| 24 | (2S,5R)-2-cyclopropyl-5-(5-fluoro-2-((2-methoxypyrido[3,4-b]pyrazin-5-yl)amino)pyridin-4-yl)-3-imino-2,5-dimethylthiomorpholine 1,1-dioxide | 485 | 4.8 | 3.5 |
| 25 | (3R,6S)-5-amino-6-cyclopropyl-3-(5-fluoro-2-((3-hydroxy-1,7-naphthyridin-8-yl)amino)pyridin-4-yl)-3,6-dimethyl-3,6-dihydro-2H-1,4-thiazine 1,1-dioxide | 471 | 0.89 | 0.59 |
| 26 | (3R,6S)-5-amino-6-cyclopropyl-3-(5-fluoro-2-((3-fluoro-1,7-naphthyridin-8-yl)amino)pyridin-4-yl)-3,6-dimethyl-3,6-dihydro-2H-1,4-thiazine 1,1-dioxide | 474 | 12 | 1.0 |
| 27 | (3R,6S)-5-amino-3-(2-((3-chloro-1,7-naphthyridin-8-yl)amino)-5-fluoropyridin-4-yl)-6-cyclopropyl-3,6-dimethyl-3,6-dihydro-2H-1,4-thiazine 1,1-dioxide | 490 | 10 | 2.9 |
| 28 | (3R,6S)-5-amino-3-(2-((2-(but-2-yn-1-yloxy)pyrido[3,4-b]pyrazin-5-yl)amino)-5-fluoropyridin-4-yl)-6-cyclopropyl-3,6-dimethyl-3,6-dihydro-2H-1,4-thiazine 1,1-dioxide | 525 | 1.5 | 1.2 |

TABLE 1-continued

| Ex | Structure IUPAC Name | LCMS m/z | BACE-1 $K_i$ (nM) | BACE2 $K_i$ (nM) |
|---|---|---|---|---|
| 29 | (3R,6S)-5-amino-3-(5-((2-(but-2-yn-1-yloxy)pyrido[3,4-b]pyrazin-5-yl)amino)-2-fluoropyridin-3-yl)-6-cyclopropyl-3,6-dimethyl-3,6-dihydro-2H-1,4-thiazine 1,1-dioxide | 525 | 1.8 | 24 |
| 30 | (3R,6S)-5-amino-3-(5-((3-(but-2-yn-1-yloxy)-1,7-naphthyridin-8-yl)amino)-2-fluoropyridin-3-yl)-6-cyclopropyl-3,6-dimethyl-3,6-dihydro-2H-1,4-thiazine 1,1-dioxide | 524 | 2.8 | 120 |
| 31 | (3R,6S)-3-(2-((1,5-naphthyridin-4-yl)amino)-5-fluoropyridin-4-yl)-5-amino-6-cyclopropyl-3,6-dimethyl-3,6-dihydro-2H-1,4-thiazine 1,1-dioxide | 456 | 59 | 3.6 |
| 32 | (3R,6S)-5-amino-6-cyclopropyl-3-(2-fluoro-5-((3-methoxy-1,7-naphthyridin-8-yl)amino)pyridin-3-yl)-3,6-dimethyl-3,6-dihydro-2H-1,4-thiazine 1,1-dioxide | 485 | 6.9 | 2.6 |
| 33 | (3R,6S)-5-amino-3-(2-((7-chloro-1,5-naphthyridin-4-yl)amino)-5-fluoropyridin-4-yl)-6-cyclopropyl-3,6-dimethyl-3,6-dihydro-2H-1,4-thiazine 1,1-dioxide | 490 | 6.2 | 0.82 |

TABLE 1-continued

| Ex | Structure IUPAC Name | LCMS m/z | BACE-1 $K_i$ (nM) | BACE2 $K_i$ (nM) |
|---|---|---|---|---|
| 34 | (3R,6S)-5-amino-6-cyclopropyl-3-(5-fluoro-2-((7-fluoro-1,5-naphthyridin-4-yl)amino)pyridin-4-yl)-3,6-dimethyl-3,6-dihydro-2H-1,4-thiazine 1,1-dioxide | 474 | 8.5 | 1.7 |
| 35 | (3R,6S)-5-amino-6-cyclopropyl-3-(5-fluoro-2-((3-methoxypyrido[2,3-b]pyrazin-8-yl)amino)pyridin-4-yl)-3,6-dimethyl-3,6-dihydro-2H-1,4-thiazine 1,1-dioxide | 487 | 5.2 | 2.2 |
| 36 | (3R,6S)-5-amino-6-cyclopropyl-3-(2-fluoro-5-((7-methoxy-1,5-naphthyridin-4-yl)amino)phenyl)-3,6-dimethyl-3,6-dihydro-2H-1,4-thiazine 1,1-dioxide | 485 | 27 | 20 |
| 37 | (3R,6S)-5-amino-6-cyclopropyl-3-(2-fluoro-5-((3-methoxypyrido[2,3-b]pyrazin-8-yl)amino)phenyl)-3,6-dimethyl-3,6-dihydro-2H-1,4-thiazine 1,1-dioxide | 486 | 40 | 53 |
| 38 | (3R,6S)-5-amino-3-(2-((7-bromopyrido[3,2-d]pyrimidin-4-yl)amino)-5-fluoropyridin-4-yl)-6-cyclopropyl-3,6-dimethyl-3,6-dihydro-2H-1,4-thiazine 1,1-dioxide | 535 | 8.2 | 3.8 |

TABLE 1-continued

| Ex | Structure / IUPAC Name | LCMS m/z | BACE-1 $K_i$ (nM) | BACE2 $K_i$ (nM) |
|---|---|---|---|---|
| 39 | 4-((4-((3R,6S)-5-amino-6-cyclopropyl-3,6-dimethyl-1,1-dioxido-3,6-dihydro-2H-1,4-thiazin-3-yl)-5-fluoropyridin-2-yl)amino)pyrido[3,2-d]pyrimidine-7-carbonitrile | 482 | 13 | 19 |

Intermediates

In another embodiment, the present invention provides the compounds shown in the table below (including tautomers thereof) as intermediates useful in the preparation of the compounds of the invention according to the above described methods, including those compounds of the invention shown in the table immediately above.

| Structure | IUPAC Name |
|---|---|
| | (2S,5R)-5-(2-bromo-5-fluoropyridin-4-yl)-2-cyclopropyl-3-imino-2,5-dimethylthiomorpholine 1,1-dioxide |
| | tert-butyl ((2S,5R)-5-(2-bromo-5-fluoropyridin-4-yl)-2-cyclopropyl-2,5-dimethyl-1,1-dioxidothiomorpholin-3-ylidene)carbamate |
| | tert-butyl ((2S,5R)-5-(2-amino-5-fluoropyridin-4-yl)-2-cyclopropyl-2,5-dimethyl-1,1-dioxidothiomorpholin-3-ylidene)carbamate |
| 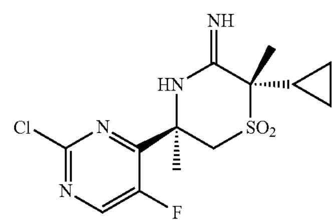 [SMILES: C[C@@]1(c2nc(Cl)ncc2F)CS(=O)(=O)[C@@](C)(C2CC2)C(=N)N1] | (2S,5R)-5-(2-chloro-5-fluoropyrimidin-4-yl)-2-cyclopropyl-3-imino-2,5-dimethylthiomorpholine 1,1-dioxide |
| 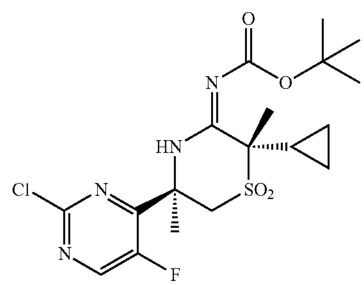 [SMILES: CC(C)(C)OC(=O)/N=C1/N[C@](C)(c2nc(Cl)ncc2F)CS(=O)(=O)[C@@]1(C)C1CC1] | tert-butyl ((2S,5R)-5-(2-chloro-5-fluoropyrimidin-4-yl)-2-cyclopropyl-2,5-dimethyl-1,1-dioxidothiomorpholin-3-ylidene)carbamate |
| 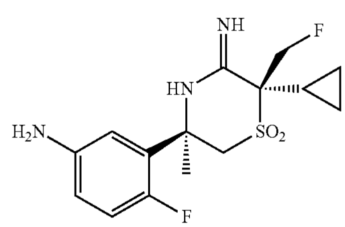 [SMILES: C[C@@]1(c2cc(N)ccc2F)CS(=O)(=O)[C@@](CF)(C2CC2)C(=N)N1] | (2S,5R)-5-(5-amino-2-fluorophenyl)-2-cyclopropyl-2-(fluoromethyl)-3-imino-5-methylthiomorpholine 1,1-dioxide |
| 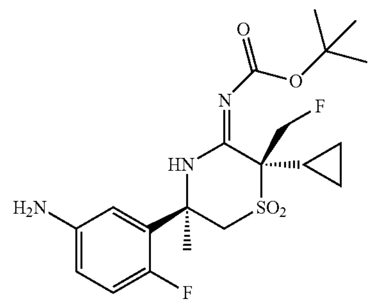 [SMILES: CC(C)(C)OC(=O)/N=C1/N[C@](C)(c2cc(N)ccc2F)CS(=O)(=O)[C@@]1(CF)C1CC1] | tert-butyl ((2S,5R)-5-(5-amino-2-fluorophenyl)-2-cyclopropyl-2-(fluoromethyl)-5-methyl-1,1-dioxidothiomorpholin-3-ylidene)carbamate |

| Structure | IUPAC Name |
|---|---|
| 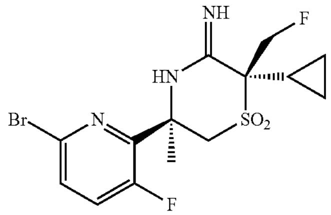 [SMILES: C[C@@]1(c2nc(Br)ccc2F)CS(=O)(=O)[C@@](CF)(C2CC2)C(=N)N1] | (2S,5R)-5-(6-bromo-3-fluoropyridin-2-yl)-2-cyclopropyl-2-(fluoromethyl)-3-imino-5-methylthiomorpholine 1,1-dioxide |
| 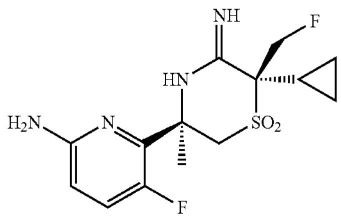 [SMILES: C[C@@]1(c2nc(N)ccc2F)CS(=O)(=O)[C@@](CF)(C2CC2)C(=N)N1] | (2S,5R)-5-(6-amino-3-fluoropyridin-2-yl)-2-cyclopropyl-2-(fluoromethyl)-3-imino-5-methylthiomorpholine 1,1-dioxide |
| 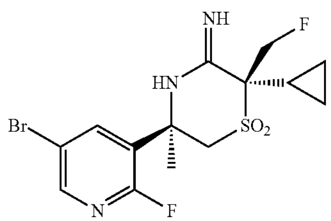 [SMILES: C[C@@]1(c2cc(Br)cnc2F)CS(=O)(=O)[C@@](CF)(C2CC2)C(=N)N1] | (2S,5R)-5-(5-bromo-2-fluoropyridin-3-yl)-2-cyclopropyl-2-(fluoromethyl)-3-imino-5-methylthiomorpholine 1,1-dioxide |
| 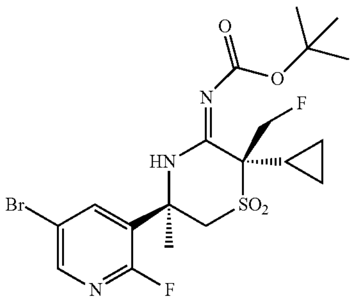 [SMILES: CC(C)(C)OC(=O)/N=C1/N[C@](C)(c2cc(Br)cnc2F)CS(=O)(=O)[C@@]1(CF)C1CC1] | tert-butyl ((2S,5R)-5-(5-bromo-2-fluoropyridin-3-yl)-2-cyclopropyl-2-(fluoromethyl)-5-methyl-1,1-dioxidothiomorpholin-3-ylidene)carbamate |
| 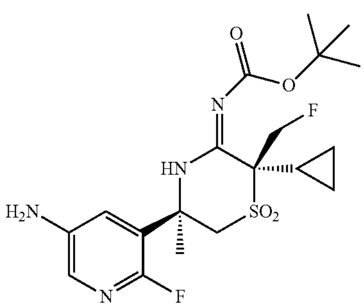 [SMILES: CC(C)(C)OC(=O)/N=C1/N[C@](C)(c2cc(N)cnc2F)CS(=O)(=O)[C@@]1(CF)C1CC1] | tert-butyl ((2S,5R)-5-(5-amino-2-fluoropyridin-3-yl)-2-cyclopropyl-2-(fluoromethyl)-5-methyl-1,1-dioxidothiomorpholin-3-ylidene)carbamate |
| 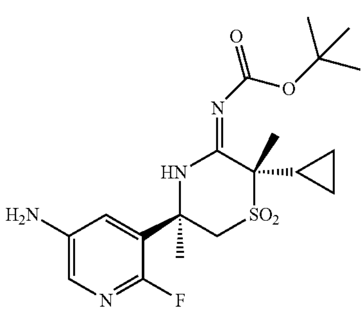 [SMILES: CC(C)(C)OC(=O)/N=C1/N[C@](C)(c2cc(N)cnc2F)CS(=O)(=O)[C@@]1(C)C1CC1] | tert-butyl ((2S,5R)-5-(5-amino-2-fluoropyridin-3-yl)-2-cyclopropyl-2,5-dimethyl-1,1-dioxidothiomorpholin-3-ylidene)carbamate |

| Structure | IUPAC Name |
|---|---|
| 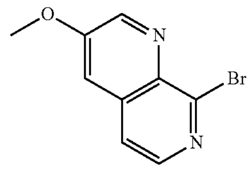 | 8-bromo-3-methoxy-1,7-naphthyridine |
| 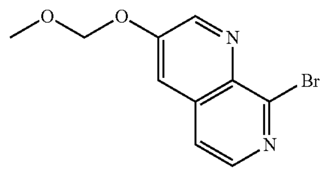 | 8-bromo-3-(methoxymethoxy)-1,7-naphthyridine |
| 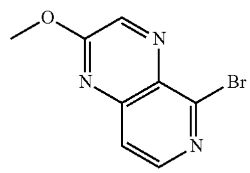 | 5-bromo-2-methoxypyrido[3,4-b]pyrazine |
| 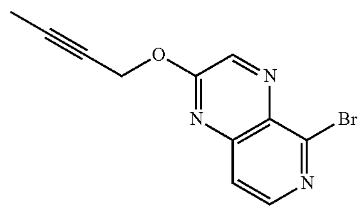 [SMILES: CC#CCOc1cnc2c(Br)nccc2n1] | 5-bromo-2-(but-2-yn-1-yloxy)pyrido[3,4-b]pyrazine |
| 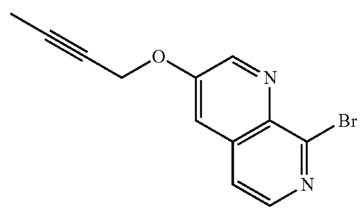 [SMILES: CC#CCOc1cnc2c(Br)nccc2c1] | 8-bromo-3-(but-2-yn-1-yloxy)-1,7-naphthyridine |
| 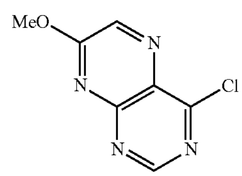 [SMILES: COc1cnc2c(Cl)ncnc2n1] | 4-chloro-7-methoxypteridine |
| 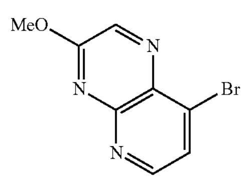 [SMILES: COc1cnc2c(Br)ccnc2n1] | 8-bromo-3-methoxypyrido[2,3-b]pyrazine |

Biological Assays

Protocols that may be used to determine the recited biological properties for the compounds of the invention are described below.

Assay 1: BACE-1 Ki Assay (BACE-1 HTRF FRET Assay)

The compounds of the invention were determined to be potent inhibitors of BACE-1 using the following assay.

The following reagents were used in this assay. Na$^+$-Acetate pH 5.0; 1% Brij-35; Glycerol; Dimethyl Sulfoxide (DMSO); Recombinant human soluble BACE-1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC$_{50}$ values for inhibitors of the soluble human BACE-1 catalytic domain. This assay monitors the increase of 620 nm fluorescence that resulted from BACE-1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE-1 enzyme. Inhibition of BACE-1 cleavage of the QSY7-APP$^{swe}$-Eu substrate by inhibitors is manifested as a suppression of 620 nm fluorescence.

Varying concentrations of inhibitors at 3× the final desired concentration in a volume of 1 µl are preincubated with purified human BACE-1 catalytic domain (3 nM in 10 µl) for 30 minutes at 30° C. in reaction buffer containing 20 mM Na-Acetate pH 5.0, 10% glycerol, 0.1% Brij-35 and 7.5% DSMO. Reactions are initiated by addition of 10 µl of 600 nM QSY7-APP$^{swe}$-Eu substrate (200 nM final) to give a final reaction volume of 30 µl in a 384 well Nunc HTRF plate. The reactions are incubated at 30° C. for 1.5 hours. The 620 nm fluorescence is then read on a Rubystar HTRF plate reader (BMG Labtechnologies) using a 50 milisecond delay followed by a 400 millisecond acquisition time window. Inhibitor IC$_{50}$ values are derived from non-linear regression analysis of concentration response curves. K$_i$ values are then calculated from IC$_{50}$ values using the Cheng-Prusoff equation using a previously determined µm value of 8 µM for the QSY7-APP$^{swe}$-Eu substrate at BACE-1. The example compounds of the invention were measured in this assay. Their measured Ki values are reported in the table above.

Assay 2: BACE-2 Assay

The compounds of the invention were determined to be potent inhibitors of BACE-2 using the following assay. Inhibitor IC$_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, K$_m$=8 µM for 4 µM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 µs delay on a RUBYstar HTRF plate reader (BMG Labtechnologies). Raw RFU data is normalized to maximum (1.0 nM BACE/DMSO) and minimum (no enzyme/DMSO) RFU values. IC$_{50}$ values are determined by nonlinear regression analysis (sigmoidal dose response, variable slope) of percent inhibition data with minimum and maximum values set to 0 and 100 percent respectively. Similar IC$_{50s}$ are obtained when using raw RFU data. The K$_i$ values are calculated from the IC$_{50}$ using the Cheng-Prusoff equation.

Assay 3: BACE-1 Cellular Assay

Certain compounds of the invention, identified in the tables herein, were determined to be potent inhibitors of BACE-1 in the following cellular assay. HEK293 cells are obtained from the American Type Culture Collection (ATCC) and stably transfected with the human amyloid precursor protein cDNA containing the FAD Swedish (enhances β-secretase processing) and London (enhances Aβ42 cleavage) mutations. A HEK293 stable clone with Aβ expression (HEK293-APP$^{swe/lon}$) is identified and maintained at 37° C., 5% CO$_2$ in the ATCC-recommended growth media supplemented with hygromycin. Determination of compound IC$_{50}$ values for inhibition of APP processing (reduction of Aβ1-40, Aβ1-42 and sAPPβ levels) in HEK293-APP$^{swe/lon}$ cells is accomplished by treatment of cells with various concentrations of compounds diluted in fresh complete growth media for 4 hours at 37° C., 5% CO$_2$. Aβ40 or Aβ42 are measured in 15 µl of media using a mesoscale based ELISA assay. Full length Aβ40 and Aβ42 peptides are captured with the N-terminal specific biotinylated-WO2 monoclonal antibody and detected using either the ruthenylated Aβ40 C-terminal specific monoclonal antibody, G2-10 or the ruthenylated Aβ42 C-terminal specific monoclonal antibody G2-11 respectively. Raw electrochemiluminescnce values are measured using a Mesoscale Sector Imager plate reader and are plotted as a function of compound concentration. IC$_{50}$ values are interpolated from the data using nonlinear regression analysis (Sigmoidal dose response fit with variable slope) of the data using GraphPad Prism software.

Assay 4: Cathepsin-D Assay

The following reagents were used in this assay: Na$^+$-Acetate pH 5.0; 1% Brij-35; Dimethyl Sulfoxide (DMSO); Purified human Cathepsin-D (>95% pure); Aspartyl protease peptide substrate AC-Cys(Eu_Chelate)-Gly-Lys-Pro_ile_leu_phe-Phe-Arg-Leu-Lys(QSY7)-ASP-ASP-NH2.

As noted above, certain compounds of the invention exhibit good selectivity of BACE-1 over Cathepsin-D. A homogeneous time-resolved FRET assay was used to determine IC$_{50}$ values of the compounds of the invention as inhibitors of purified human Cathepsin-D. This assay monitors the increase of 620 nm fluorescence that resulted from Cathepsin-D cleavage of an aspartyl protease peptide FRET substrate (AC-Cys(Eu_Chelate)-Gly-Lys-Pro_ile_leu_phe-Phe-Arg-Leu-Lys(QSY7)-ASP-ASP-NH2). This substrate contains an C-terminal QSY7 moiety that serves as a quencher of the N-terminal Europium fluorophore (620 nm Em). In the absence of enzyme activity, 620 nm fluorescence is low in the assay and increased linearly over 1 hour in the presence of uninhibited Cathepsin-D enzyme. Inhibition of Cathespin D cleavage of the Eu-Aspartyl Protease-QSY7 substrate by inhibitors is manifested as a suppression of 620 nm fluorescence.

Varying concentrations of inhibitors in a volume of 100 nl are preincubated with purified human Cathepsin-D (0.1 nM in 10 µl) for 30 minutes at 30° C. in reaction buffer containing 100 mM Na-Acetate pH 5.0, and 0.02% Brij-35. Reactions are initiated by addition of 10 µl of 100 nM Eu-Aspartyl Protease-QSY7 substrate (50 nM final) to give a final reaction volume of 20 µl in a 384 well Nunc HTRF plate. The reactions are incubated at 30° C. for 30 minutes. The 620 nm fluorescence is then read on a Envision Multilabel plate reader (Perkin-Elmer) using a 200 microsecond delay followed by a 400 microsecond acquisition time window. Inhibitor $IC_{50}$ values are derived from non-linear regression analysis of concentration response curves. $K_i$ values are then calculated from $IC_{50}$ values using the Cheng-Prusoff equation using a previously determined μm value of 4 μM for the Eu-Aspartyl Protease-QSY7 substrate at Cathepsin-D.

The following example compounds of the invention, indicated by the corresponding example number, were measured in the above described BACE-1 Cellular Assay and Cathepsin-D Assay. The measured values are listed in the table below.

| Example number | BACE-1 Cellular Assay ($IC_{50}$ (nM)) | Cathepsin-D Assay (Ki (nM)) |
|---|---|---|
| 1 | 24 | 563 |
| 2 | 52 | 159 |
| 3 | 25 | 5530 |
| 4 | 19 | 6650 |
| 5 | 10 | 710 |
| 6 | 3 | >9400 |
| 7 | 132 | 1123 |
| 8 | 91 | 4011 |
| 9 | 111 | >9400 |
| 10 | 0.25 | >9400 |
| 11 | 4.1 | 857 |
| 12 | 99 | 629 |
| 13 | 6.6 | 3378 |
| 14 | 21 | 1653 |
| 15 | 3.4 | 321 |
| 16 | 2.6 | 2447 |
| 17 | 16 | 146 |
| 18 | 4.8 | 651 |
| 19 | 192 | 9300 |
| 20 | 5.3 | 2158 |
| 22 | 15 | >9400 |
| 23 | — | >9400 |
| 24 | 34 | 7400 |
| 25 | 4.9 | >9400 |
| 26 | 250 | >9400 |
| 27 | 180 | >9400 |
| 28 | 6.3 | >9400 |
| 29 | 30 | >9400 |
| 30 | 28 | >9400 |
| 31 | 180 | >9400 |
| 32 | 24 | 650 |
| 33 | 27 | 820 |
| 34 | 32 | 4900 |
| 35 | 10 | >9400 |
| 36 | 3.5 | >9400 |
| 37 | 23 | >9400 |
| 38 | 110 | 3200 |
| 39 | 130 | >9400 |

Assay 5: Aβ Reduction In Vivo

As noted above, certain compounds of the invention were determined to exhibit unexpectedly improved reduction of amyloid beta peptide (Aβ) levels in vivo. The in vivo efficacy and/or potency of BACE inhibitors (test compounds) can be evaluated using a variety of animal models, including mouse, rat, dog, and monkey, and these animals can be wild type, transgenic, or gene knockout animals.

Generally, animals are administered (by oral gavage, intravenous injection, or by other suitable route) a test compound in doses ranging from, for example, 0.1 mg/kg (mg of compound per kg of animal body weight) to 100 mg/kg formulated in vehicles, such as cyclodextrin, phosphate buffer, hydroxypropyl methylcellulose or other suitable vehicles. One to twenty-four hours following the administration of compound, animals are sacrificed, and tissues (for example, brain, cerebrospinal fluid (CSF), and/or plasma) are collected for analysis of Aβ levels and/or test compound concentrations (Dovey et al., 2001, *Journal of Neurochemistry*, 76, 173-181). Tissue samples are processed appropriately and then analyzed for the presence of Aβ by specific sandwich ELISA assays based on electrochemiluminescence (ECL) technology. Changes in Aβ levels are then reported as percent change relative to levels in comparable animals treated only with vehicle but otherwise processed as described above for test compound-treated animals.

For example, in the following assay for which data are reported below, male CD IGS rats (body weight approximately 120 g, Charles River Laboratories, Kingston, N.Y.) were used to assess lowering of CSF levels of $Aβ_{1-40}$ ($Aβ_{40}$) in the presence of compounds of the invention. At time 0, animals were administered by oral gavage a test compound at a dose of 10 mg/kg in 20% hydroxypropyl-β-cyclodextrin (dosing volume 5 mL/kg). A separate group of animals received 20% hydroxypropyl-β-cyclodextrin alone to serve as the vehicle control group. Three hours after administration, the rats were euthanized with excess $CO_2$. Immediately following euthanasia, CSF was collected from the cisterna magna and quickly frozen on dry ice. Samples were stored at −80° C. until quantification of $Aβ_{40}$ levels.

The measurement of endogenous rat $Aβ_{40}$ in CSF relied on the 585 antibody (Ab585, BioSource, NONO585), which specifically recognizes the N-terminal sequence of rodent $Aβ_{40}$, and on the monoclonal antibody, G2-10, which specifically recognizes the free C-terminus of $Aβ_{40}$. Ab585 was labeled with biotin (b-Ab585) by first dialyzing the antibody sample extensively versus PBS (pH 7.8) to remove impurities, followed by dilution to between 1 and 2 mg/mL protein concentration. EZ-Link Sulfo-NHS-LC-Biotin (Pierce) was dissolved in PBS (pH 7.8) at a concentration of 1 mg/mL immediately prior to use. Ab585 was labeled with EZ-Link Sulfo-NHS-LC-biotin using a 10:1 biotin:antibody ratio by incubation at room temperature for 1 hour. The labeling reaction was quenched by addition of 1.0 M glycine to a final concentration of 0.1 M followed by 10 minute incubation at room temperature. Glycine was removed by extensive dialysis versus PBS.

For rat CSF $Aβ_{40}$ determinations, a calibration curve of various concentrations of synthetic rodent $Aβ_{40}$ was assayed in parallel with rat CSF samples in duplicate using an avidin-coated 96-well MSD plate (Mesoscale Diagnostics). Either 50 μL of rodent $Aβ_{40}$ standards diluted in PBS (pH 7.4) supplemented with 1% BSA and 1% Tween-20 (standard diluent buffer) or 40 μL of standard diluent buffer plus 10 μL rat CSF were added to each 96 well avidin-coated plate. To each well was added 50 μL of 0.1 M HEPES (pH 7.5), 2% BSA, 2% Tween-20, 0.3 M NaCl (2×$Aβ_{40}$ buffer) supplemented with the b-Ab585 capture and ruthenylated-G2-10 detection antibodies diluted to 1 μg/mL and 0.5 μg/mL, respectively. Plates were shaken for 1 min on a microplate shaker, covered to protect from light and incubated overnight (~16 h) at 4° C. For detection, plates were first washed twice with 100 μL of 1×CSF $Aβ_{40}$ buffer followed by addition of 160 μL of 1×MSD read buffer-T (Mesoscale Diagnostics) diluted in 1×CSF $Aβ_{40}$ buffer. Plates were read on a MSD Sector Imager 2400 model (Mesoscale Diagnosotics). Data were analyzed using GraphPad Prism and were either plotted as raw counts or absolute $Aβ_{40}$ calculated from the rodent $Aβ_{40}$ standard curve. Percent change values for each test compound were calculated by normalization of the average absolute CSF $Aβ_{40}$ levels in each test compound-treated cohort to the average absolute CSF $Aβ_{40}$ levels in the vehicle cohort (Δ % CSF $Aβ_{40}$ @ 10 mpk). Comparative results are shown in the table below.

Assay 6: P-Glycoprotein (P-Gp) Efflux Susceptibility Assay

As noted above, certain compounds of the invention were determined to exhibit unexpectedly reduced susceptibility to efflux by P-Glycoprotein (P-gp). As P-gp is expressed at the blood-brain-barrier, among other tissues, lower P-gp efflux ratio values are associated with a better ability to cross the blood-brain-barrier to reach the site of BACE-1 expression in the central nervous system. P-gp efflux ratios are measured in cellular assays using cell lines that express P-gp from a number of species including rat, monkey, and human. The following assay was used to measure the rat P-gp efflux ratios, which are believed to be the most sensitive measure of P-gp susceptibility, for the compounds of the invention (test compounds) reported in the tables below.

The bidirectional transport of test compounds was conducted across pig kidney epithelial (LLC-PK1) cell monolayers. Native LLC-PK1 cells were obtained from The Netherlands Cancer Institute (Amsterdam, The Netherlands), and used under a license agreement. LLC-PK1 cells expressing a cDNA encoding rat Mdr1a (rat LLC-Mdr1a) were made in-house by stable transfection of LLC-PK1 cells with a rat MDR1 cDNA. LLC-PK1 and rat LLC-Mdr1a cell lines were cultured in 96-well transwell culture plates. Test compound (final concentration 0.1 µM) was prepared in Hank's Balanced Salt Solution (HBSS), 10 mM HEPES, pH 7.4. Substrate solution (150 µL) was added to either the apical (A) or the basolateral (B) compartment of the culture plate, and buffer (150 µL; HBSS, 10 mM HEPES, pH 7.4) was added to the compartment opposite to that containing the compound. At t=3 h, 50 µL samples were removed from both sides of monolayers dosed with test compound and placed in 96 well plates, internal standard (50 µL 1 µM labetolol) was added to the samples. Samples were analyzed by LC/MS/MS using an Applied Biosystems SCIEX API 5000 triple quadruple mass spectrometry (Concord, ON, Canada) with a TurboIonSpray ion source in the positive ion mode. A Thermo Scientific Transcend LX-2 system (Franklin, Mass.) was coupled to the API 5000 with a flow rate of 800 µL/min to direct sample into the mass spectrometer. A Waters ACQUITY UPLC T3 (2×30 mm, 1.7 µm; Milford, Mass.) column was used for sample analysis. Mobile phase A consisted of 0.1% formic acid in water. Mobile phase B was acetonitrile with 0.1% formic acid. A gradient elution program was utilized where the solvent composition was held at 5% B for 0.25 min, changed from 5% B to 95% B at 0.25 min, and followed by holding at 95% B for 0.5 min, then, went back to 5% B at 0.75 min. The column was then re-equilibrated at the original solvent composition for 0.5 min. Mass spectrometric detection was accomplished by multiple reaction monitoring (MRM) of transitions unique to each compound. Sample concentration was obtained by extrapolation from the standard curve. Verapamil (1 µM) was used as the positive control to assess the functional activity of Pgp. The experiment was performed in triplicate.

The $P_{app}$ was calculated by the following formula for samples taken at t=3 h:

$$P_{app} = \frac{\text{Volume of Receptor Chamber(mL)}}{[\text{Area of membrane(cm}^2)][\text{Initial Concentration}(\mu M)]} \times \frac{\Delta \text{ in Concentration}(\mu M)}{\Delta \text{ in Time}(s)}$$

where "Volume of Receptor Chamber" is 0.15 mL, "Area of membrane" is 0.11 cm², the "Initial Concentration" is the sum of the concentration measured in the donor compartment plus the concentration measured in the receiver compartment at t=3 h, "Δ in Concentration" is the concentration in the receiver compartment at 3 h, and "Δ in Time" is the incubation time (3×60×60=10800 s). $P_{app}$ was expressed as $10^{-6}$ cm/s.

The $P_{app}$ reported in the table below is the average of the $P_{app}$ for transport from A to B and $P_{app}$ for transport from B to A at t=3 hr.

$$P_{app}(LLC\text{-}PK1 \text{ Cells}) = \frac{P_{app}(A \to B) + P_{app}(B \to A)}{2}$$

The B-A/A-B ratio (BAAB) was calculated by dividing the $P_{app}$ from B to A by the $P_{app}$ from A to B at t=3 h:

$$B - A/A - B \text{ Ratio} = \frac{P_{app}(B \text{ to } A)}{P_{app}(A \text{ to } B)}$$

Assay 7: In Vitro Phospholipidosis Assay

Drug-induced phospholipidosis (PL) is characterized by intracellular accumulation of phospholipids with lamellular bodies, and may result from impaired phospholipid metabolism in the lysosome (Anderson et al., 2006, *FEBS Letter*, 580, 5533-5540), and many compounds known to cause drug-induced PL are also associated with adverse drug reactions. Using a method described in the literature (Bhandari et al., 2008, *Assay and Drug Dev. Tech.*, 6(3), 407-419), an in vitro cellular assay can provide data that can determine the PL potential of test compounds. In this assay, compounds that lower values for mean inclusion count of a fluorescent phospholipid (described below) versus control are associated with reduced potential for PL. Certain compounds of the invention surprisingly exhibit reduction in PL potential as determined by the assay reported herein.

HepG2 cells were dispensed into 96-well collagen I coated plates at an initial density of $2.0 \times 10^5$ cells in 200 µL complete culturing medium (MEM Media w/Earle's Balanced Salt Solution supplemented with 10 IU penicillin, 10 µg/mL streptomycin, and 10% heat inactivated fetal bovine serum). Cells were incubated overnight at 37° C. with 5% $CO_2$, 89% humidity prior to treatment.

A solution of fluorescently labeled phospholipid N-(7-nitrobenz-2-oxa-1,3-diazol-4-yl)-1,2-dihexadecanoyl-sn-glycero-3-phosphoethanolamine (NBD-PE) was prepared at a concentration of 10 mM in absolute ethanol. Dissolution of the NBD-PE was facilitated by sonication in a room temperature water bath for 30 minutes. NBD-PE medium was prepared by diluting NBD-PE stock to a final concentration of 50 µM in complete culturing medium, filtering (pore size, 0.22 µm) prior to use.

Compound treatment stocks were prepared in dimethyl sulfoxide at 500× final concentrations. Working treatment solutions were prepared by diluting compound stocks into NBD-PE medium with DMSO serving as the vehicle control. Treatment concentration was 20 µM. Amiodarone ((2-{4-[(2-butyl-1-benzofuran-3-yl)carbonyl]-2,6-diiodophenoxy}ethyl)diethylamine) served as the assay positive control at the same concentration. All treatments were tested in triplicate for 24 hours.

Following treatment, cultures were rinsed once with Hank's Balanced Salt Solution (HBSS) containing no phenol red. Cultures were then incubated for 30 minutes at 37° C. with 1 mM Hoechst 33342 nuclear stain and 1 mM cell tracker orange cytoplasm stain. After incubation, cells were rinsed once with HBSS and then fixed in 2% formalin solution.

Cultures were imaged using the IN Cell Analyzer 2000 imaging system. One set of images were acquired with the 4× objective using the appropriate Hoechst filter settings to acquire a full-well cell count. Another set of images were acquired to evaluate treatment-related phospholipidosis with the 20× objective.

Images were analyzed using custom algorithms created in the IN Cell Workstation software using NBD-PE inclusion count in the cell cytoplasm as and endpoint associated with phospholipidosis. Data were expressed as fold over control, normalized to the DMSO vehicle control response.

As noted above, certain example compounds of the invention exhibit an unexpected and beneficial combination of BACE-1 potency in a binding assay, BACE-1 potency in a cellular assay, ability to lower Aβ levels in vivo, reduced susceptibility to efflux by p-glycoprotein, a low propensity to cause phospholipidosis in a cellular phospholipidosis assay and/or high selectivity for BACE-1 over Cathepsin-D. The following example compounds of the invention were measured in the above described assays. The measured values are listed in the table below. (The "-" indicates the value was not measured.)

| Example number (from Table 1) | Aβ reduction in vivo in rat (Δ% CSF Aβ40 @ 10 mpk) (Assay 5) | P-gp efflux assay (rMDR1a BAAB, 1 μM) (Assay 6) | In Vitro Phospholipidosis Assay: Mean NBD-PE Inclusion Count (Fold over control) (Assay 7) |
|---|---|---|---|
| 1 | −58 | 6.1 | — |
| 5 | — | 31 | 1.3 |
| 6 | −92 | 1.5 | 3.1 |
| 7 | — | — | 1.9 |
| 14 | — | 2.9 | — |
| 16 | −85 | 31 | — |
| 18 | −87 | 11 | — |
| 22 | −70 | 26 | 0.9 |
| 35 | −75 | — | — |
| 36 | −67 | — | — |

Comparison Table 1 below provides data showing that the compounds of the invention, each of which contain a C2 carbocyclic moiety, have significantly higher BACE-1 potency (Assay 1), BACE-2 (Assay 2) potency and in vivo Aβ reduction (Assay 5) as measured in the above-described assays relative to certain comparator compounds described in WO2012139425 (WO'426).

| Ex. No in WO'426 | Structure | BACE-1 Ki (nM) (Assay 1) | BACE-2 Ki (nM) (Assay 2) | BACE-1 Cellular IC$_{50}$ (nM) (Assay 3) | Aβ reduction in vivo in rat (Δ% CSF Aβ40 @ 10 mpk) (Assay 5) |
|---|---|---|---|---|---|
| 30 | 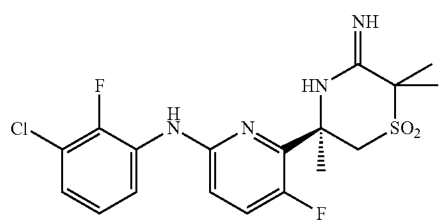 [SMILES: CC1(C)C(=N)N[C@](C)(c2nc(Nc3cccc(Cl)c3F)ccc2F)CS1(=O)=O] | 3198 | 862 | — | — |
| 30a | 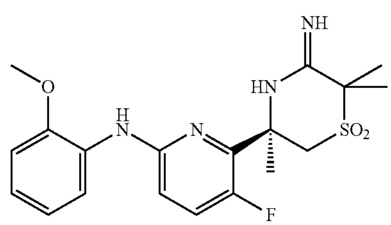 [SMILES: COc1ccccc1Nc1ccc(F)c([C@]2(C)CS(=O)(=O)C(C)(C)C(=N)N2)n1] | 5277 | 517 | — | — |
| 30b | 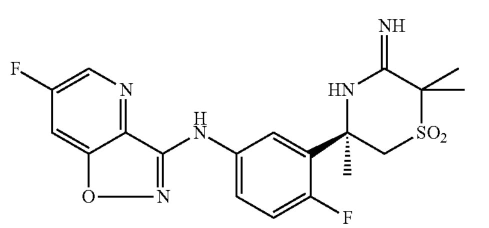 [SMILES: CC1(C)C(=N)N[C@](C)(c2cc(Nc3noc4cc(F)cnc34)ccc2F)CS1(=O)=O] | 19.2 | 6.1 | 82 | +6 |

Comparison Table 2 below provides data showing that the compounds of the invention, each of which contains a carbocyclic moiety at the position corresponding to $R^{1A}$ (or $R^{1B}$) in formula (I) above, show high potency as a BACE inhibitor, reduced susceptibility to P-gp efflux and to phospholipidosis (PL) relative to a comparator compound (example 47 of WO2014059185).

Comparison Table 2

| Ex 47 of WO2014059185 | BACE-1 Ki (nM) (i) Data from Assay 1 (ii) Data reported in US'109 | Aβ reduction in vivo in rat (Δ% CSF Aβ40 @ 10 mpk) (i) Data from Assay 5 (ii) Data reported in US'109 | P-gp efflux assay (rMDR1a BAAB, 1 μM) (Assay 6) | In Vitro PL: Mean NBD-PE Inclusion Count (Fold over control) (Assay 7) |
|---|---|---|---|---|
| (structure) | (i) 3.3 (ii) 2.9 | (i) −88 (ii) −82 | 7.9 | 13 |

While the present invention has been described in view of the specific embodiments set forth above, many alternatives, modifications and other variations thereof will be apparent to those of ordinary skill in the art. All such alternatives, modifications and variations are intended to fall within the spirit and scope of the present invention.

We claim:
1. A compound, or a pharmaceutically acceptable salt thereof, said compound having the structural Formula (I):

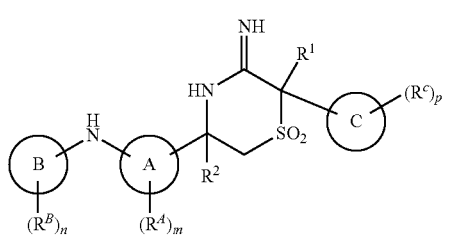

(I)

or a tautomer thereof having the structural Formula (I'):

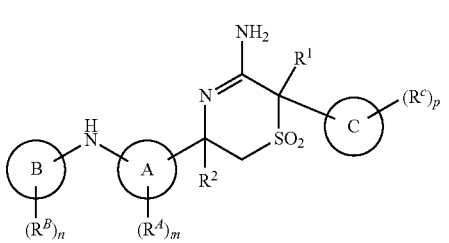

(I')

or pharmaceutically acceptable salt thereof, wherein:
$R^1$ is selected from the group consisting of H, halogen, lower alkyl, and lower heteroalkyl, wherein said lower alkyl and said lower heteroalkyl is optionally substituted with one or more halogen;
$R^2$ is selected from the group consisting of H, lower alkyl, lower cycloalkyl, and lower heteroalkyl, wherein said lower alkyl, lower cycloalkyl, and said lower heteroalkyl are optionally substituted with one or more halogen;
ring A is selected from the group consisting of phenyl, pyridinyl, pyridazinyl, pyrimidinyl, and pyrazinyl;
m is 0, 1, 2, or 3;
each $R^A$ (when present) is independently selected from the group consisting of halogen, —CN, —CH$_3$, —CH$_2$CH$_3$, —CH(CH$_3$)$_2$, cyclopropyl, —CH$_2$OCH$_3$, —CF$_3$, —CHF$_2$, —CH$_2$F, —OCH$_3$, —O-cyclopropyl, —O—CH$_2$-cyclopropyl, —OCF$_3$, —OCHF$_2$, and —OCH$_2$F;
ring B is heteroaryl;
n is 0, 1, 2, or 3;
each $R^B$ (when present) is independently selected from the group consisting of halogen, —CN, —OH, —CH$_3$, —CH$_2$CH$_3$, —CH(CH$_3$)$_2$, cyclopropyl, —CH$_2$-cyclopropyl, —CH$_2$OCH$_3$, —C≡CH, —C≡C—CH$_3$, —CF$_3$, —CHF$_2$, —CH$_2$F, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, —OCF$_3$, —OCHF$_2$, —OCH$_2$F, and —OCH$_2$CH$_2$F;
ring C is selected from the group consisting of cyclopropyl and cyclobutyl;
p is 0, 1, or 2; and
each $R^C$ (when present) is independently selected from the group consisting of: halogen, —OH, —CN, lower alkyl, and lower alkoxy, where said lower alkyl and said lower alkoxy are each optionally substituted with 1 to 3 fluorine.

2. A compound of claim 1, or a tautomer thereof, or a pharmaceutically acceptable salt of said compound or said tautomer, wherein:
$R^1$ is selected from the group consisting of —CH$_3$ and —CH$_2$F;
ring C is cyclopropyl;
p is 0; and
$R^2$ is —CH$_3$.

3. A compound of claim 2, or a tautomer thereof, or a pharmaceutically acceptable salt of said compound or said tautomer, wherein:

ring A is selected from the group consisting of phenyl, pyridinyl, and pyrimidinyl;

m is 1; and each $R^A$ is independently selected from the group consisting of fluoro.

4. A compound of claim 3, or a tautomer thereof, or a pharmaceutically acceptable salt of said compound or said tautomer, wherein:

n is 0 or 1;

ring B, $R^B$, and n form a moiety selected from the group consisting of:

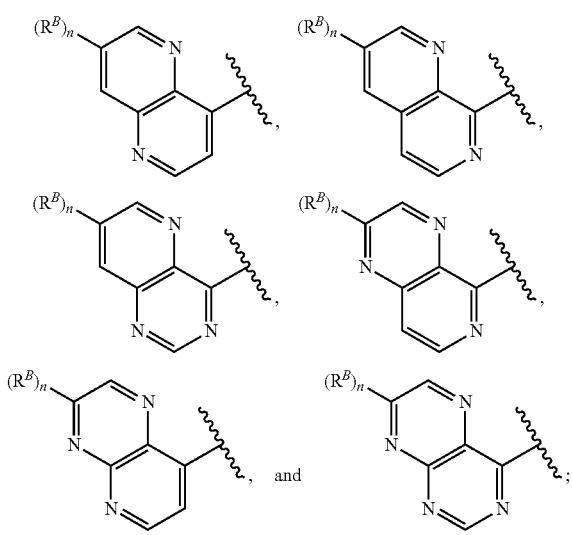

and $R^B$ (when present) is selected from the group consisting of fluoro, chloro, bromo, —OH, —CN, —OCH$_3$, and —OCH$_2$—C≡C—CH$_3$.

5. A compound of claim 1, or a tautomer thereof, or a pharmaceutically acceptable salt of said compound or said tautomer, said compound selected from the group consisting of:

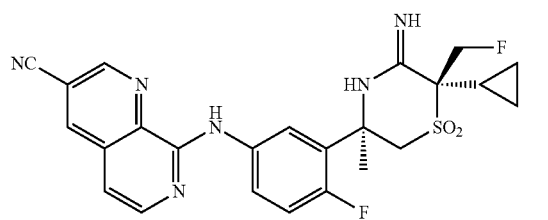

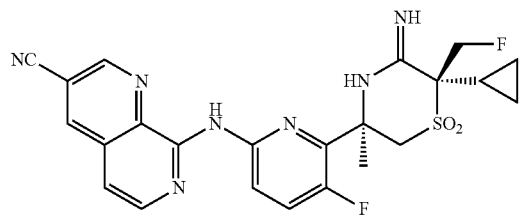

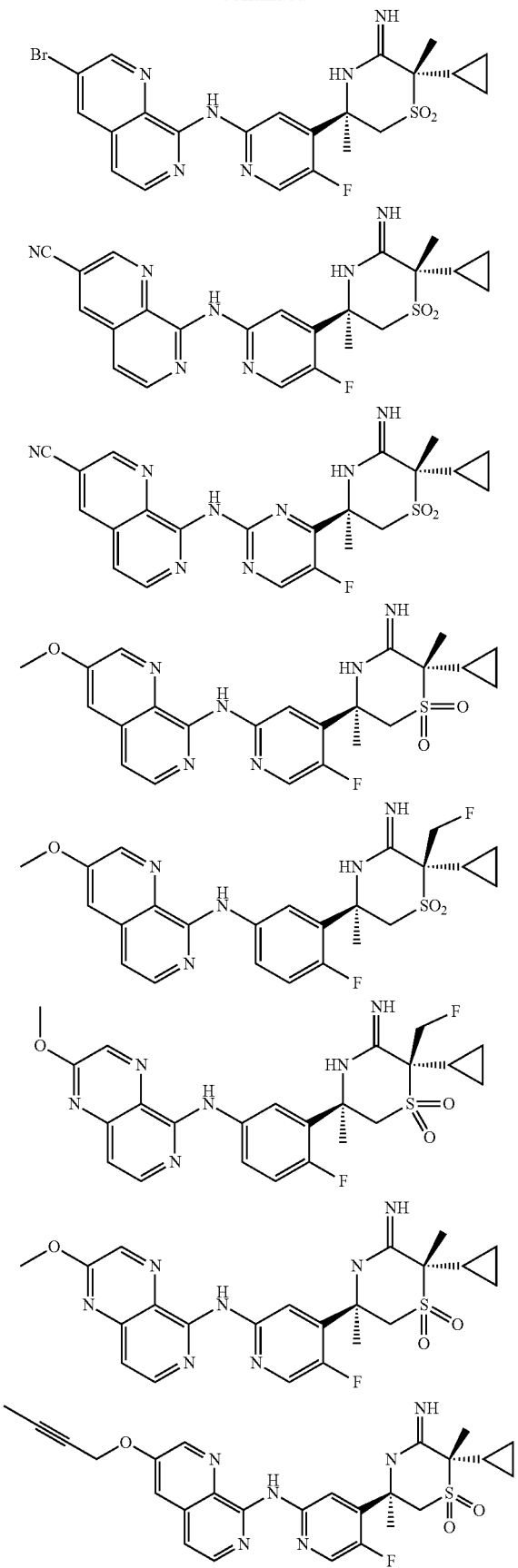

123
-continued
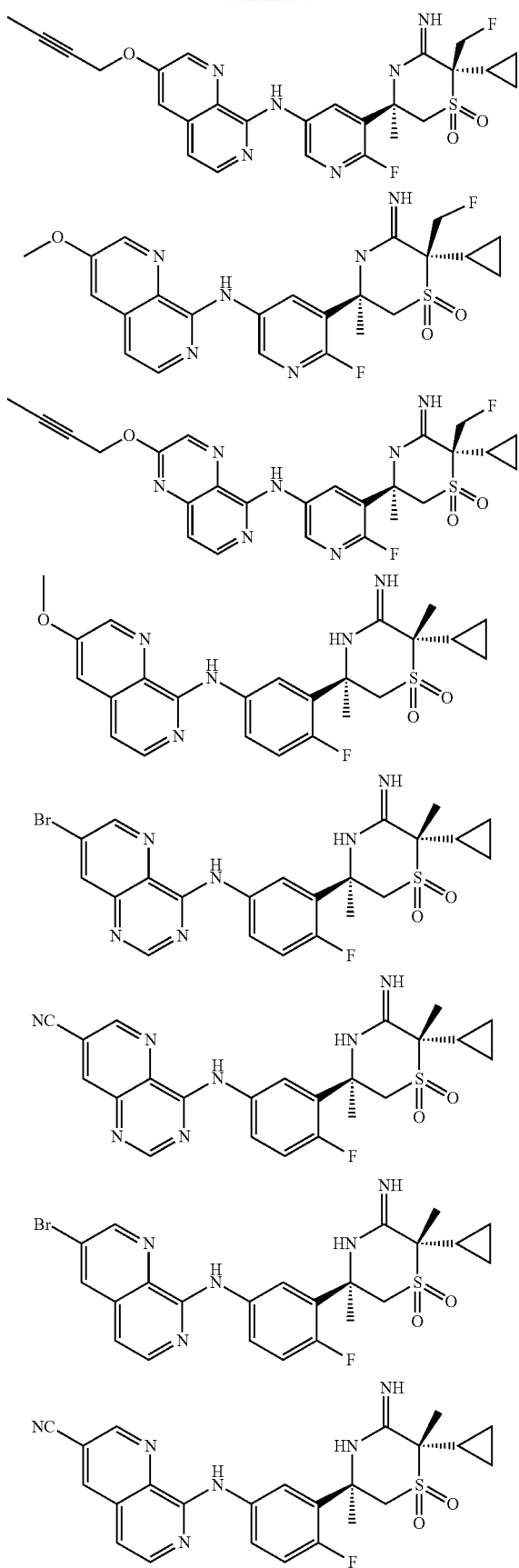
124
-continued
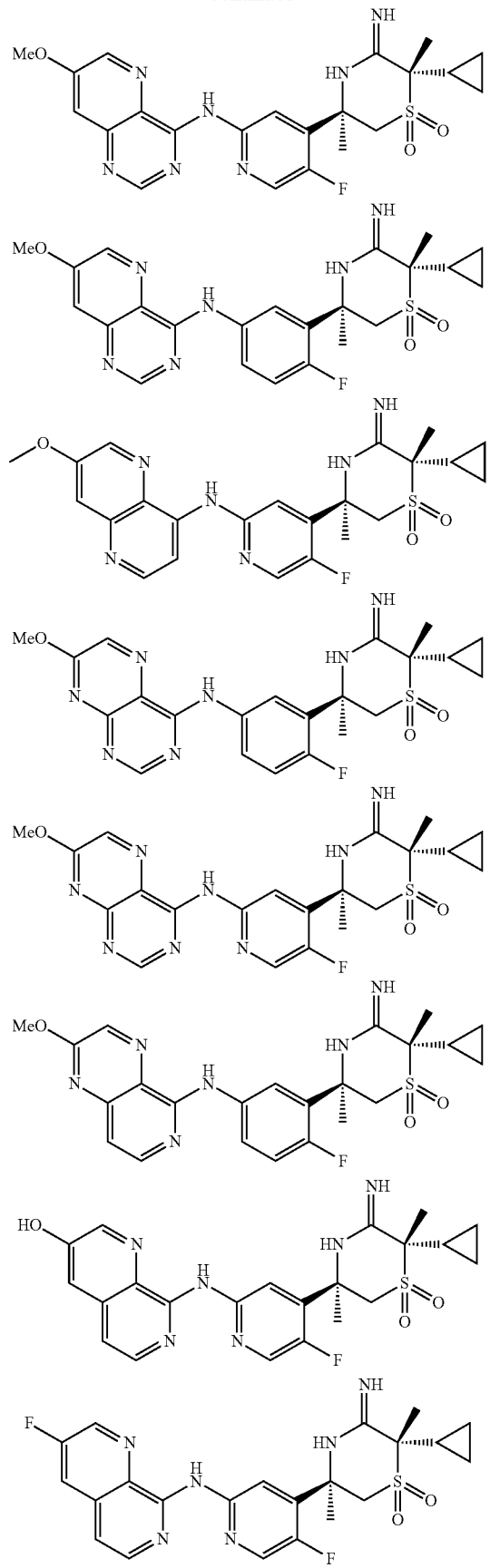

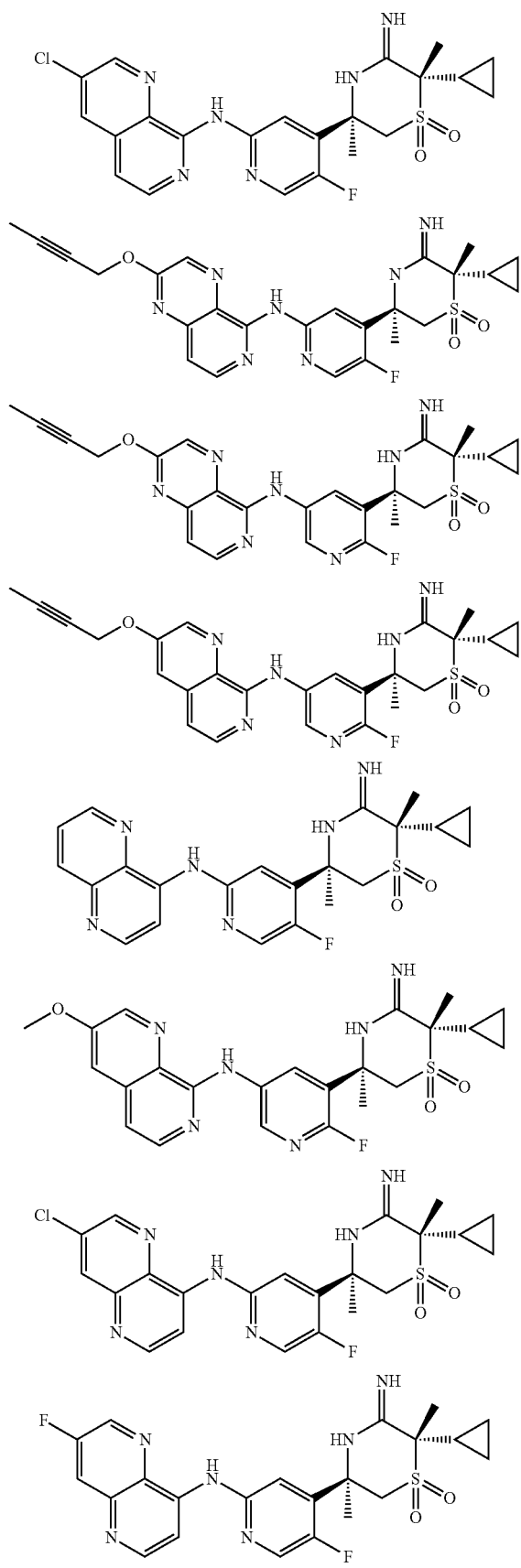
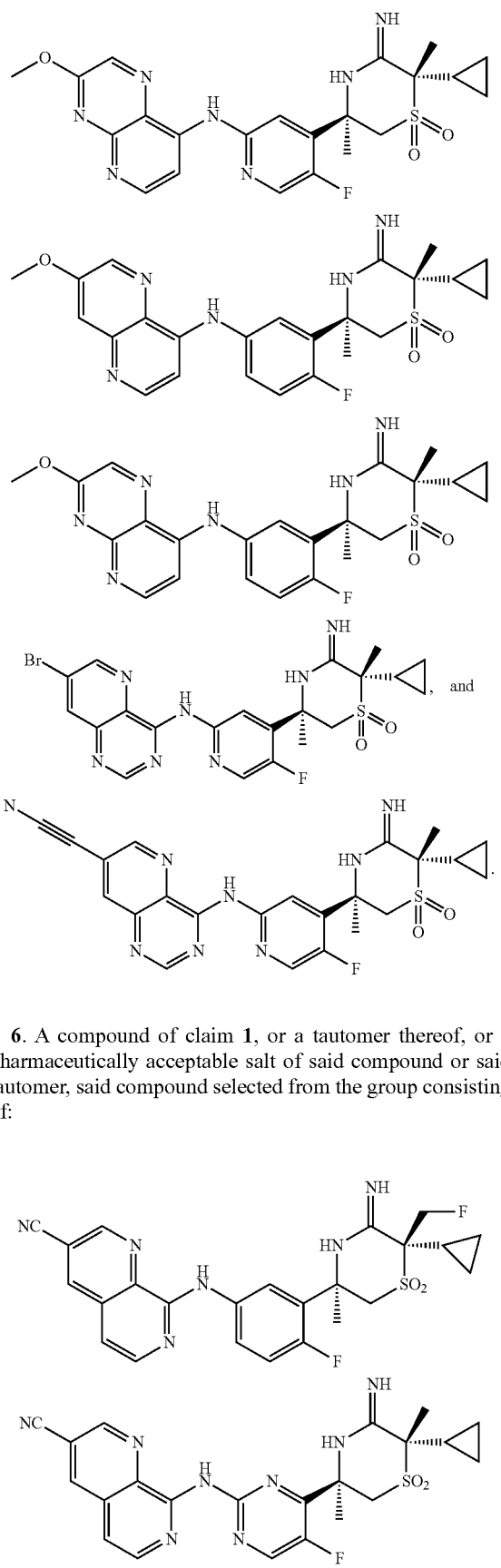
6. A compound of claim 1, or a tautomer thereof, or a pharmaceutically acceptable salt of said compound or said tautomer, said compound selected from the group consisting of:
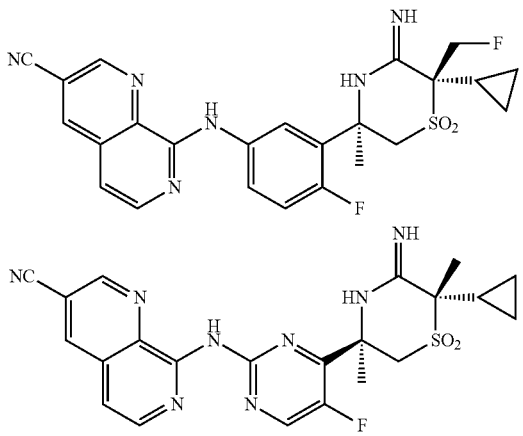

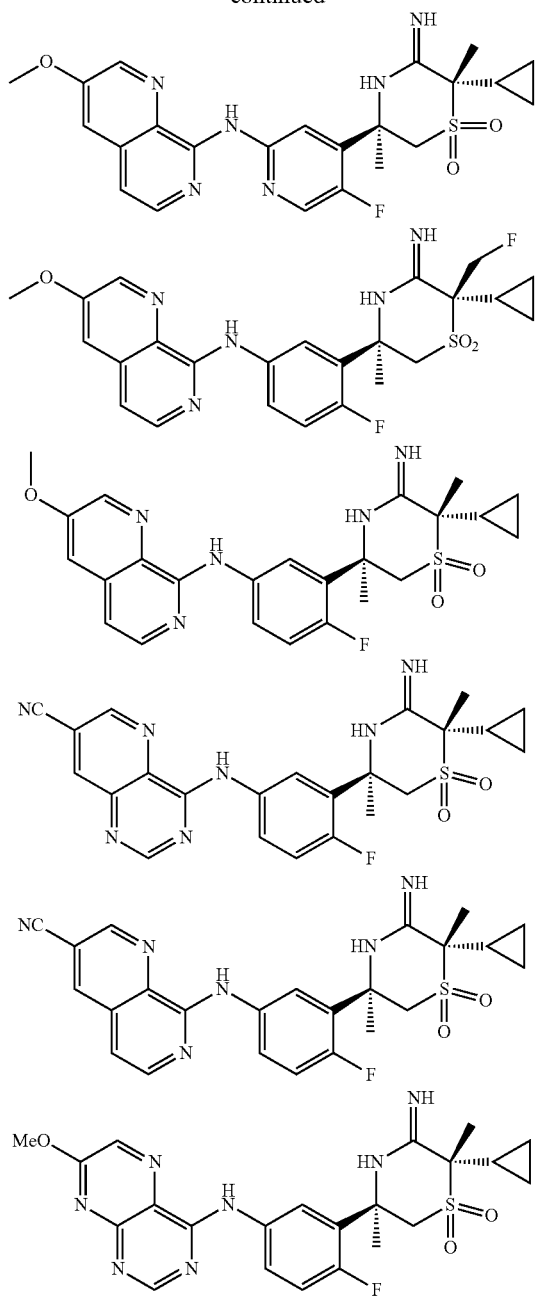

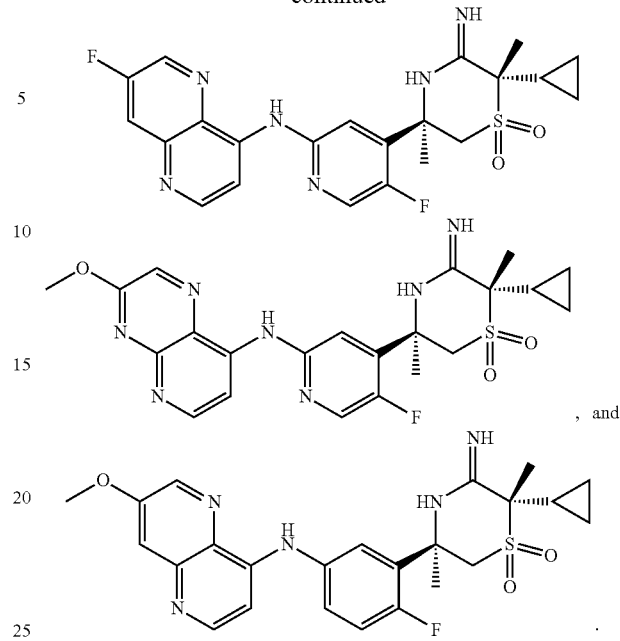

, and

7. A pharmaceutical composition comprising a compound according to claim 1, or a tautomer thereof, or a pharmaceutically acceptable salt of said compound or said tautomer, and a pharmaceutically acceptable carrier or diluent.

8. A method of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound according to claim 1, or a tautomer thereof, or a pharmaceutically acceptable salt of said compound or said tautomer, to a patient in need thereof in an amount effective to treat said disease or pathology.

9. The method of claim 8, wherein disease or pathology is Alzheimer's disease.

* * * * *